United States Patent
Steward et al.

(10) Patent No.: US 7,514,088 B2
(45) Date of Patent: Apr. 7, 2009

(54) MULTIVALENT CLOSTRIDIAL TOXIN DERIVATIVES AND METHODS OF THEIR USE

(75) Inventors: Lance E. Steward, Irvine, CA (US); Fernandez-Salas Ester, Fullerton, CA (US); Joseph Francis, Aliso Viejo, CA (US); Shengwin Li, Irvine, CA (US); Marcella A. Gilmore, Santa Ana, CA (US); Kei Roger Aoki, Coto de Caza, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 11/376,696

(22) Filed: Mar. 15, 2006

(65) Prior Publication Data

US 2006/0211619 A1 Sep. 21, 2006

Related U.S. Application Data

(60) Provisional application No. 60/662,151, filed on Mar. 15, 2005, provisional application No. 60/661,953, filed on Mar. 15, 2005.

(51) Int. Cl.
*A61K 39/08* (2006.01)
*A61K 39/00* (2006.01)
*A61K 39/02* (2006.01)
*C07K 2/00* (2006.01)
*C07K 1/00* (2006.01)

(52) U.S. Cl. .............. 424/239.1; 424/184.1; 424/185.1; 424/192.1; 424/234.1; 424/247.1; 530/300; 530/350

(58) Field of Classification Search .............. 424/184.1, 424/185.1, 192.1, 234.1, 239.1, 247.1; 530/300, 530/350
See application file for complete search history.

(56) References Cited

U.S. PATENT DOCUMENTS

| | | | |
|---|---|---|---|
| 5,437,291 A | 8/1995 | Pasricha et al. |
| 5,670,484 A | 9/1997 | Binder |
| 5,714,469 A | 2/1998 | DeMarsh |
| 5,989,545 A | 11/1999 | Foster et al. |
| 6,063,768 A | 5/2000 | First |
| 6,113,915 A | 9/2000 | Aoki et al. |
| 6,139,845 A | 10/2000 | Donovan |
| 6,143,306 A | 11/2000 | Donovan |
| 6,203,794 B1 | 3/2001 | Dolly et al. |
| 6,261,572 B1 | 7/2001 | Donovan |
| 6,265,379 B1 | 7/2001 | Donovan |
| 6,299,893 B1 | 10/2001 | Schwartz et al. |
| 6,306,403 B1 | 10/2001 | Donovan |
| 6,319,505 B1 | 11/2001 | Aoki et al. |
| 6,337,075 B1 | 1/2002 | Donovan |
| 6,358,917 B1 | 3/2002 | Carruthers et al. |
| 6,358,926 B2 | 3/2002 | Donovan |
| 6,368,605 B1 | 4/2002 | Donovan |
| 6,395,513 B1 | 5/2002 | Foster et al. |
| 6,416,765 B1 | 7/2002 | Donovan |
| 6,423,319 B1 | 7/2002 | Brooks |
| 6,458,365 B1 | 10/2002 | Aoki |
| 6,464,986 B1 | 10/2002 | Aoki et al. |
| 6,565,870 B1 | 5/2003 | Donovan |
| 6,620,415 B2 | 9/2003 | Donovan |
| 6,623,742 B2 | 9/2003 | Voet |
| 6,641,820 B1 | 11/2003 | Donovan |
| 6,683,049 B1 | 1/2004 | Aoki et al. |
| 6,740,321 B1 | 5/2004 | Donovan |
| 6,767,544 B2 | 7/2004 | Brooks et al. |
| 6,776,992 B2 | 8/2004 | Aoki et al. |
| 6,827,931 B1 | 12/2004 | Donovan |
| 6,831,059 B2 | 12/2004 | Donovan |
| 6,838,434 B2 | 1/2005 | Voet |
| 6,843,998 B1 | 1/2005 | Steward et al. |
| 6,869,610 B2 | 3/2005 | Aoki et al. |
| 6,872,397 B2 | 3/2005 | Aoki et al. |
| 6,989,545 B1 | 1/2006 | Rathmell et al. |
| 2002/0010138 A1 | 1/2002 | Aoki et al. |

(Continued)

FOREIGN PATENT DOCUMENTS

WO WO 95/32738 12/1995

(Continued)

OTHER PUBLICATIONS

Johnson et al., "Clostridial botulinum and its Neurotoxins: A Metabolic and Cellular Perspective", *39 Toxicon*, 1703-1722 (2001).

Raffestin et al., "Organization and Regulation of the Neurotoxin Genes in *Clostridium botulinum* and *Clostridium telani*", 10 *Anaerobe*, 93-100 (2004).

Inoue et al., "Structural Analysis by X-Ray Crystallography and Calorimetry of Haemagglutinin Component (HA1) of the Progenitor Toxin from *Clostridium botulinum*", 149 *Microbiol.*, 3361-3370 (2003).

Arndt et al., "The Structure of the Neurotoxin-Associated Protein HA33/A from Clostridial botulinum Suggests a Reoccurring β-trefoil Fold in the Progenitor Toxin Complex", *346 J. Mol. Biol.*, 1083-1093 (2005).

(Continued)

*Primary Examiner*—Rodney P. Swartz
(74) *Attorney, Agent, or Firm*—Dean G. Stathakis; Joel B. German; Martin A. Voet

(57) ABSTRACT

The present invention is directed to multivalent *Clostridial* neurotoxin derivatives having more than one binding domain directed to a cell surface feature of a target cell. Such modified neurotoxins are useful as therapeutic compositions to prevent exocytosis and secretion by the target cell. Conditions in which such compositions man be useful include, without limitation, disorders of the sensory or motor nervous system, acute or chronic pain, cancer, pancreatitis, hyperhydrosis, glandular disorders, viral infections, cystic fibrosis and the like. The invention is also directed to methods of using and administering such a composition, and methods of treating a given condition using such a composition.

27 Claims, 2 Drawing Sheets

U.S. PATENT DOCUMENTS

| | | |
|---|---|---|
| 2002/0169942 A1 | 11/2002 | Sugimoto |
| 2003/0166238 A1 | 9/2003 | Shone et al. |
| 2003/0211121 A1 | 11/2003 | Donovan |
| 2004/0013692 A1 | 1/2004 | Aoki et al. |
| 2004/0037852 A1 | 2/2004 | Aoki et al. |
| 2004/0062776 A1 | 4/2004 | Voet |
| 2004/0086531 A1 | 5/2004 | Barron |
| 2004/0115139 A1 | 6/2004 | Katz et al. |
| 2004/0126396 A1 | 7/2004 | Aoki et al. |
| 2004/0126397 A1 | 7/2004 | Aoki et al. |
| 2004/0151740 A1 | 8/2004 | Aoki et al. |
| 2004/0175399 A1 | 9/2004 | Schiffman |
| 2004/0176299 A1 | 9/2004 | Sachs et al. |
| 2004/0180061 A1 | 9/2004 | Donovan |
| 2004/0234532 A1 | 11/2004 | First |
| 2004/0253274 A1 | 12/2004 | Voet |
| 2005/0031648 A1 | 2/2005 | Brin et al. |
| 2006/0024331 A1 | 2/2006 | Fernandez-Salas |
| 2006/0211619 A1 | 9/2006 | Steward et al. |

FOREIGN PATENT DOCUMENTS

| | | |
|---|---|---|
| WO | WO 96/33273 | 10/1996 |
| WO | WO 98/07864 | 2/1998 |
| WO | WO 99/17806 | 4/1999 |
| WO | WO 99/29721 | 6/1999 |
| WO | WO 99/55359 | 11/1999 |
| WO | WO 01/14570 | 3/2001 |
| WO | WO 02/40506 | 5/2002 |
| WO | WO 02/44199 | 6/2002 |
| WO | WO 2005/035730 | 4/2005 |
| WO | WO 2005/068494 | 7/2005 |
| WO | WO 2005/077416 | 8/2005 |
| WO | WO 2006/011966 | 2/2006 |
| WO | WO 2006/017749 | 2/2006 |
| WO | WO 2006/026780 | 3/2006 |
| WO | WO2006/099590 | 9/2006 |
| WO | WO 2006/101809 | 9/2006 |

OTHER PUBLICATIONS

Zhou et al., "Haemagglutinin-33 of Type Q Botulinum Neurotoxin Complex Binds with Synaptotagmin II", *272 Febs Lett.*, 2717-2726 (2005).

Bonifacino et al., *J Cell Biol.* 145: 923 (1999).

Drapkin et al., *J. Clin. Invest.* 105: 589-596 (2000).

Duman & Forte, *Am. J. Physiol. Cell Physiol.* 285: C237-C249 (2003).

Morris M.C., et al., *Nature Biotechnology*, 19:1173-1176 (2001).

Embury et al., *Diabetes*, 50:1706-1713 (2001).

Schwartz, J.J. et al., "Peptide-mediated cellular delivery", *Curr. Opin. Mol. Therapeutics*, 2:162-7 (2000).

Prochiantz, A., "Messenger proteins:homeoproteins, TAT and others", *Curr. Opin. Cell. Biol.*, 12:400-6 (2000).

Ho, A. et al., "Synthetic PTDs: enhanced transduction potential in vitro and in vivo", *Cancer Res.*, 61, 474-7 (2001).

Wender, P.A. et al., "The Design, Synthesis, And Evaluation of Molecules That Enable or Enhance Cellular Uptake: Peptoid Molecular Trasnporters", *Proc. Natl. Acad. Sci.*, 97:13003-13008 (2000).

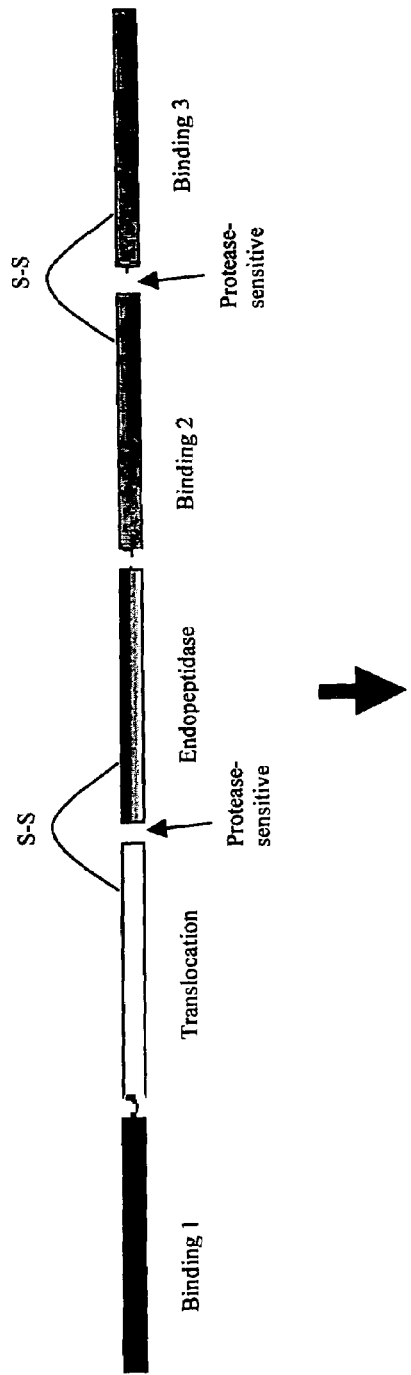
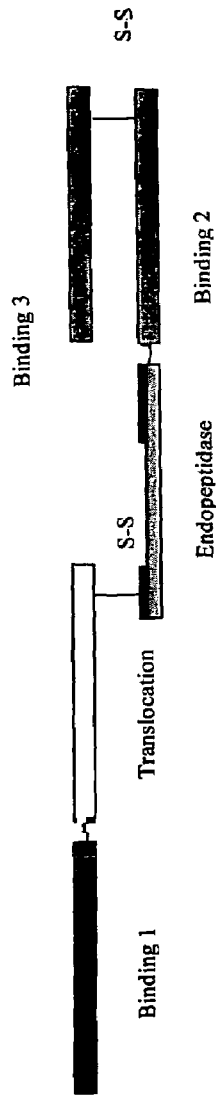
Figure 2 A
Figure 2 B

SEQUENCE LISTING

<160> NUMBER OF SEQ ID NOS: 56

<210> SEQ ID NO 1
<211> LENGTH: 1296
<212> TYPE: PRT
<213> ORGANISM: C. botulinum

<400> SEQUENCE: 1

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

```
Val Lys Ala Phe Lys Ile His Asn Lys Ile Trp Val Ile Pro Glu Arg
         35                  40                  45
Asp Thr Phe Thr Asn Pro Glu Glu Gly Asp Leu Asn Pro Pro Pro Glu
 50                  55                  60
Ala Lys Gln Val Pro Val Ser Tyr Tyr Asp Ser Thr Tyr Leu Ser Thr
 65                  70                  75                  80
Asp Asn Glu Lys Asp Asn Tyr Leu Lys Gly Val Thr Lys Leu Phe Glu
                 85                  90                  95
Arg Ile Tyr Ser Thr Asp Leu Gly Arg Met Leu Leu Thr Ser Ile Val
            100                 105                 110
Arg Gly Ile Pro Phe Trp Gly Gly Ser Thr Ile Asp Thr Glu Leu Lys
        115                 120                 125
Val Ile Asp Thr Asn Cys Ile Asn Val Ile Gln Pro Asp Gly Ser Tyr
        130                 135                 140
Arg Ser Glu Glu Leu Asn Leu Val Ile Ile Gly Pro Ser Ala Asp Ile
145                 150                 155                 160
Ile Gln Phe Glu Cys Lys Ser Phe Gly His Glu Val Leu Asn Leu Thr
                165                 170                 175
Arg Asn Gly Tyr Gly Ser Thr Gln Tyr Ile Arg Phe Ser Pro Asp Phe
            180                 185                 190
Thr Phe Gly Phe Glu Glu Ser Leu Glu Val Asp Thr Asn Pro Leu Leu
        195                 200                 205
Gly Ala Gly Lys Phe Ala Thr Asp Pro Ala Val Thr Leu Ala His Glu
        210                 215                 220
Leu Ile His Ala Gly His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
                245                 250                 255
Glu Val Ser Phe Glu Glu Leu Arg Thr Phe Gly Gly His Asp Ala Lys
            260                 265                 270
Phe Ile Asp Ser Leu Gln Glu Asn Glu Phe Arg Leu Tyr Tyr Tyr Asn
        275                 280                 285
Lys Phe Lys Asp Ile Ala Ser Thr Leu Asn Lys Ala Lys Ser Ile Val
        290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
            340                 345                 350
Asn Phe Val Lys Phe Phe Lys Val Leu Asn Arg Lys Thr Tyr Leu Asn
        355                 360                 365
Phe Asp Lys Ala Val Phe Lys Ile Asn Ile Val Pro Lys Val Asn Tyr
        370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
                405                 410                 415
Lys Asn Phe Thr Gly Leu Phe Glu Phe Tyr Lys Leu Leu Cys Val Arg
            420                 425                 430
Gly Ile Ile Thr Ser Lys Thr Lys Ser Leu Asp Lys Gly Tyr Asn Lys
        435                 440                 445
```

```
Ala Leu Asn Asp Leu Cys Ile Lys Val Asn Asn Trp Asp Leu Phe Phe
    450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Glu Glu Asn Ile Ser Leu
            485                 490                 495
Asp Leu Ile Gln Gln Tyr Tyr Leu Thr Phe Asn Phe Asp Asn Glu Pro
            500                 505                 510
Glu Asn Ile Ser Ile Glu Asn Leu Ser Ser Asp Ile Ile Gly Gln Leu
            515                 520                 525
Glu Leu Met Pro Asn Ile Glu Arg Phe Pro Asn Gly Lys Lys Tyr Glu
    530                 535                 540
Leu Asp Lys Tyr Thr Met Phe His Tyr Leu Arg Ala Gln Glu Phe Glu
545                 550                 555                 560
His Gly Lys Ser Arg Ile Ala Leu Thr Asn Ser Val Asn Glu Ala Leu
                565                 570                 575
Leu Asn Pro Ser Arg Val Tyr Thr Phe Phe Ser Ser Asp Tyr Val Lys
                580                 585                 590
Lys Val Asn Lys Ala Thr Glu Ala Ala Met Phe Leu Gly Trp Val Glu
            595                 600                 605
Gln Leu Val Tyr Asp Phe Thr Asp Glu Thr Ser Glu Val Ser Thr Thr
    610                 615                 620
Asp Lys Ile Ala Asp Ile Thr Ile Ile Pro Tyr Ile Gly Pro Ala
625                 630                 635                 640
Leu Asn Ile Gly Asn Met Leu Tyr Lys Asp Asp Phe Val Gly Ala Leu
                645                 650                 655
Ile Phe Ser Gly Ala Val Ile Leu Leu Glu Phe Ile Pro Glu Ile Ala
                660                 665                 670
Ile Pro Val Leu Gly Thr Phe Ala Leu Val Ser Tyr Ile Ala Asn Lys
            675                 680                 685
Val Leu Thr Val Gln Thr Ile Asp Asn Ala Leu Ser Lys Arg Asn Glu
    690                 695                 700
Lys Trp Asp Glu Val Tyr Lys Tyr Ile Val Thr Asn Trp Leu Ala Lys
705                 710                 715                 720
Val Asn Thr Gln Ile Asp Leu Ile Arg Lys Lys Met Lys Glu Ala Leu
            725                 730                 735
Glu Asn Gln Ala Glu Ala Thr Lys Ala Ile Ile Asn Tyr Gln Tyr Asn
            740                 745                 750
Gln Tyr Thr Glu Glu Glu Lys Asn Asn Ile Asn Phe Asn Ile Asp Asp
    755                 760                 765
Leu Ser Ser Lys Leu Asn Glu Ser Ile Asn Lys Ala Met Ile Asn Ile
    770                 775                 780
Asn Lys Phe Leu Asn Gln Cys Ser Val Ser Tyr Leu Met Asn Ser Met
785                 790                 795                 800
Ile Pro Tyr Gly Val Lys Arg Leu Glu Asp Phe Asp Ala Ser Leu Lys
            805                 810                 815
Asp Ala Leu Leu Lys Tyr Ile Tyr Asp Asn Arg Gly Thr Leu Ile Gly
            820                 825                 830
Gln Val Asp Arg Leu Lys Asp Lys Val Asn Asn Thr Leu Ser Thr Asp
            835                 840                 845
Ile Pro Phe Gln Leu Ser Lys Tyr Val Asp Asn Gln Arg Leu Leu Ser
    850                 855                 860
Thr Phe Thr Glu Tyr Ile Lys Asn Ile Ile Asn Thr Ser Ile Leu Asn
```

-continued

```
            865                 870                 875                 880
Leu Arg Tyr Glu Ser Asn His Leu Ile Asp Leu Ser Arg Tyr Ala Ser
                885                 890                 895
Lys Ile Asn Ile Gly Ser Lys Val Asn Phe Asp Pro Ile Asp Lys Asn
            900                 905                 910
Gln Ile Gln Leu Phe Asn Leu Glu Ser Ser Lys Ile Glu Val Ile Leu
            915                 920                 925
Lys Asn Ala Ile Val Tyr Asn Ser Met Tyr Glu Asn Phe Ser Thr Ser
        930                 935                 940
Phe Trp Ile Arg Ile Pro Lys Tyr Phe Asn Ser Ile Ser Leu Asn Asn
945                 950                 955                 960
Glu Tyr Thr Ile Ile Asn Cys Met Glu Asn Asn Ser Gly Trp Lys Val
                965                 970                 975
Ser Leu Asn Tyr Gly Glu Ile Ile Trp Thr Leu Gln Asp Thr Gln Glu
                980                 985                 990
Ile Lys Gln Arg Val Val Phe Lys  Tyr Ser Gln Met Ile  Asn Ile Ser
            995                 1000                1005
Asp Tyr  Ile Asn Arg Trp Ile  Phe Val Thr Ile Thr  Asn Asn Arg
    1010                1015                1020
Leu Asn  Asn Ser Lys Ile Tyr  Ile Asn Gly Arg Leu  Ile Asp Gln
    1025                1030                1035
Lys Pro  Ile Ser Asn Leu Gly  Asn Ile His Ala Ser  Asn Asn Ile
    1040                1045                1050
Met Phe  Lys Leu Asp Gly Cys  Arg Asp Thr His Arg  Tyr Ile Trp
    1055                1060                1065
Ile Lys  Tyr Phe Asn Leu Phe  Asp Lys Glu Leu Asn  Glu Lys Glu
    1070                1075                1080
Ile Lys  Asp Leu Tyr Asp Asn  Gln Ser Asn Ser Gly  Ile Leu Lys
    1085                1090                1095
Asp Phe  Trp Gly Asp Tyr Leu  Gln Tyr Asp Lys Pro  Tyr Tyr Met
    1100                1105                1110
Leu Asn  Leu Tyr Asp Pro Asn  Lys Tyr Val Asp Val  Asn Asn Val
    1115                1120                1125
Gly Ile  Arg Gly Tyr Met Tyr  Leu Lys Gly Pro Arg  Gly Ser Val
    1130                1135                1140
Met Thr  Thr Asn Ile Tyr Leu  Asn Ser Ser Leu Tyr  Arg Gly Thr
    1145                1150                1155
Lys Phe  Ile Ile Lys Lys Tyr  Ala Ser Gly Asn Lys  Asp Asn Ile
    1160                1165                1170
Val Arg  Asn Asn Asp Arg Val  Tyr Ile Asn Val Val  Val Lys Asn
    1175                1180                1185
Lys Glu  Tyr Arg Leu Ala Thr  Asn Ala Ser Gln Ala  Gly Val Glu
    1190                1195                1200
Lys Ile  Leu Ser Ala Leu Glu  Ile Pro Asp Val Gly  Asn Leu Ser
    1205                1210                1215
Gln Val  Val Val Met Lys Ser  Lys Asn Asp Gln Gly  Ile Thr Asn
    1220                1225                1230
Lys Cys  Lys Met Asn Leu Gln  Asp Asn Asn Gly Asn  Asp Ile Gly
    1235                1240                1245
Phe Ile  Gly Phe His Gln Phe  Asn Asn Ile Ala Lys  Leu Val Ala
    1250                1255                1260
Ser Asn  Trp Tyr Asn Arg Gln  Ile Glu Arg Ser Ser  Arg Thr Leu
    1265                1270                1275
```

```
Gly Cys Ser Trp Glu Phe Ile Pro Val Asp Asp Gly Trp Gly Glu
    1280            1285                1290

Arg Pro Leu
    1295

<210> SEQ ID NO 2
<211> LENGTH: 1291
<212> TYPE: PRT
<213> ORGANISM: C. botulinum

<400> SEQUENCE: 2

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
                20                  25                  30

Tyr Tyr Lys Ala Phe Lys Ile Thr Asp Arg Ile Trp Ile Ile Pro Glu
            35                  40                  45

Arg Tyr Thr Phe Gly Tyr Lys Pro Glu Asp Phe Asn Lys Ser Ser Gly
        50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
```

-continued

```
               340                 345                 350
Met Phe Gly Phe Thr Glu Thr Asn Ile Ala Glu Asn Tyr Lys Ile Lys
            355                 360                 365

Thr Arg Ala Ser Tyr Phe Ser Asp Ser Leu Pro Pro Val Lys Ile Lys
        370                 375                 380

Asn Leu Leu Asp Asn Glu Ile Tyr Thr Ile Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
            435                 440                 445

Val Asp Asn Glu Asp Leu Phe Phe Ile Ala Asp Lys Asn Ser Phe Ser
    450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
            515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
            595                 600                 605

Asn Thr Met Asp Lys Ile Ala Asp Ile Ser Leu Ile Val Pro Tyr Ile
    610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
            675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
            755                 760                 765
```

-continued

```
Asp Asn Ile Asn Asn Phe Ile Asn Gly Cys Ser Val Ser Tyr Leu Met
770                 775                 780
Lys Lys Met Ile Pro Leu Ala Val Glu Lys Leu Leu Asp Phe Asp Asn
785                 790                 795                 800
Thr Leu Lys Lys Asn Leu Leu Asn Tyr Ile Asp Glu Asn Lys Leu Tyr
                805                 810                 815
Leu Ile Gly Ser Ala Glu Tyr Glu Lys Ser Lys Val Asn Lys Tyr Leu
            820                 825                 830
Lys Thr Ile Met Pro Phe Asp Leu Ser Ile Tyr Thr Asn Asp Thr Ile
        835                 840                 845
Leu Ile Glu Met Phe Asn Lys Tyr Asn Ser Glu Ile Leu Asn Asn Ile
    850                 855                 860
Ile Leu Asn Leu Arg Tyr Lys Asp Asn Asn Leu Ile Asp Leu Ser Gly
865                 870                 875                 880
Tyr Gly Ala Lys Val Glu Val Tyr Asp Gly Val Glu Leu Asn Asp Lys
                885                 890                 895
Asn Gln Phe Lys Leu Thr Ser Ser Ala Asn Ser Lys Ile Arg Val Thr
            900                 905                 910
Gln Asn Gln Asn Ile Ile Phe Asn Ser Val Phe Leu Asp Phe Ser Val
        915                 920                 925
Ser Phe Trp Ile Arg Ile Pro Lys Tyr Lys Asn Asp Gly Ile Gln Asn
    930                 935                 940
Tyr Ile His Asn Glu Tyr Thr Ile Ile Asn Cys Met Lys Asn Asn Ser
945                 950                 955                 960
Gly Trp Lys Ile Ser Ile Arg Gly Asn Arg Ile Ile Trp Thr Leu Ile
                965                 970                 975
Asp Ile Asn Gly Lys Thr Lys Ser Val Phe Phe Glu Tyr Asn Ile Arg
            980                 985                 990
Glu Asp Ile Ser Glu Tyr Ile Asn Arg Trp Phe Phe Val Thr Ile Thr
        995                 1000                1005
Asn Asn Leu Asn Asn Ala Lys Ile Tyr Ile Asn Gly Lys Leu Glu
    1010                1015                1020
Ser Asn Thr Asp Ile Lys Asp Ile Arg Glu Val Ile Ala Asn Gly
    1025                1030                1035
Glu Ile Ile Phe Lys Leu Asp Gly Asp Ile Asp Arg Thr Gln Phe
    1040                1045                1050
Ile Trp Met Lys Tyr Phe Ser Ile Phe Asn Thr Glu Leu Ser Gln
    1055                1060                1065
Ser Asn Ile Glu Glu Arg Tyr Lys Ile Gln Ser Tyr Ser Glu Tyr
    1070                1075                1080
Leu Lys Asp Phe Trp Gly Asn Pro Leu Met Tyr Asn Lys Glu Tyr
    1085                1090                1095
Tyr Met Phe Asn Ala Gly Asn Lys Asn Ser Tyr Ile Lys Leu Lys
    1100                1105                1110
Lys Asp Ser Pro Val Gly Glu Ile Leu Thr Arg Ser Lys Tyr Asn
    1115                1120                1125
Gln Asn Ser Lys Tyr Ile Asn Tyr Arg Asp Leu Tyr Ile Gly Glu
    1130                1135                1140
Lys Phe Ile Ile Arg Arg Lys Ser Asn Ser Gln Ser Ile Asn Asp
    1145                1150                1155
Asp Ile Val Arg Lys Glu Asp Tyr Ile Tyr Leu Asp Phe Phe Asn
    1160                1165                1170
```

```
Leu Asn Gln Glu Trp Arg Val Tyr Thr Tyr Lys Tyr Phe Lys Lys
    1175            1180                1185

Glu Glu Glu Lys Leu Phe Leu Ala Pro Ile Ser Asp Ser Asp Glu
    1190            1195                1200

Phe Tyr Asn Thr Ile Gln Ile Lys Glu Tyr Asp Glu Gln Pro Thr
    1205            1210                1215

Tyr Ser Cys Gln Leu Leu Phe Lys Lys Asp Glu Glu Ser Thr Asp
    1220            1225                1230

Glu Ile Gly Leu Ile Gly Ile His Arg Phe Tyr Glu Ser Gly Ile
    1235            1240                1245

Val Phe Glu Glu Tyr Lys Asp Tyr Phe Cys Ile Ser Lys Trp Tyr
    1250            1255                1260

Leu Lys Glu Val Lys Arg Lys Pro Tyr Asn Leu Lys Leu Gly Cys
    1265            1270                1275

Asn Trp Gln Phe Ile Pro Lys Asp Glu Gly Trp Thr Glu
    1280            1285                1290

<210> SEQ ID NO 3
<211> LENGTH: 1291
<212> TYPE: PRT
<213> ORGANISM: C. botulinum

<400> SEQUENCE: 3

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
                20                  25                  30

Pro Glu Lys Ala Phe Arg Ile Thr Gly Asn Ile Trp Val Ile Pro Asp
            35                  40                  45

Arg Phe Ser Arg Asn Ser Asn Pro Asn Leu Asn Lys Pro Pro Arg Val
        50                  55                  60

Thr Ser Pro Lys Ser Gly Tyr Tyr Asp Pro Asn Tyr Leu Ser Thr Asp
65                  70                  75                  80

Ser Asp Lys Asp Pro Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255
```

```
Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
            275                 280                 285

Phe Glu Glu Lys Ala Leu Asp Tyr Tyr Arg Ser Ile Ala Lys Arg Leu
            290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
            325                 330                 335

Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
            355                 360                 365

Val Gln Asn Arg Lys Ile Tyr Leu Ser Asn Val Tyr Thr Pro Val Thr
            370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
            405                 410                 415

Arg Asn Pro Ala Leu Arg Lys Val Asn Pro Glu Asn Met Leu Tyr Leu
            420                 425                 430

Phe Thr Lys Phe Cys His Lys Ala Ile Asp Gly Arg Ser Leu Tyr Asn
            435                 440                 445

Lys Thr Leu Asp Cys Arg Glu Leu Leu Val Lys Asn Thr Asp Leu Pro
450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
            485                 490                 495

Val Asp Gln Val Ile Leu Ser Lys Asn Thr Ser Glu His Gly Gln Leu
            500                 505                 510

Asp Leu Leu Tyr Pro Ser Ile Asp Ser Glu Ser Glu Ile Leu Pro Gly
            515                 520                 525

Glu Asn Gln Val Phe Tyr Asp Asn Arg Thr Gln Asn Val Asp Tyr Leu
            530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
            565                 570                 575

Lys Val Tyr Thr Tyr Phe Pro Thr Leu Ala Asn Lys Val Asn Ala Gly
            580                 585                 590

Val Gln Gly Gly Leu Phe Leu Met Trp Ala Asn Asp Val Val Glu Asp
            595                 600                 605

Phe Thr Thr Asn Ile Leu Arg Lys Asp Thr Leu Asp Lys Ile Ser Asp
            610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
            645                 650                 655

Thr Ile Leu Leu Glu Ala Phe Pro Glu Phe Thr Ile Pro Ala Leu Gly
            660                 665                 670
```

-continued

```
Ala Phe Val Ile Tyr Ser Lys Val Gln Glu Arg Asn Glu Ile Ile Lys
        675                 680                 685

Thr Ile Asp Asn Cys Leu Glu Gln Arg Ile Lys Arg Trp Lys Asp Ser
        690                 695                 700

Tyr Glu Trp Met Met Gly Thr Trp Leu Ser Arg Ile Ile Thr Gln Phe
705                 710                 715                 720

Asn Asn Ile Ser Tyr Gln Met Tyr Asp Ser Leu Asn Tyr Gln Ala Gly
                725                 730                 735

Ala Ile Lys Ala Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
        755                 760                 765

Asp Val Lys Ile Ser Glu Ala Met Asn Ile Asn Lys Phe Ile Arg
    770                 775                 780

Glu Cys Ser Val Thr Tyr Leu Phe Lys Asn Met Leu Pro Lys Val Ile
785                 790                 795                 800

Asp Glu Leu Asn Glu Phe Asp Arg Asn Thr Lys Ala Lys Leu Ile Asn
                805                 810                 815

Leu Ile Asp Ser His Asn Ile Ile Leu Val Gly Glu Val Asp Lys Leu
            820                 825                 830

Lys Ala Lys Val Asn Asn Ser Phe Gln Asn Thr Ile Pro Phe Asn Ile
        835                 840                 845

Phe Ser Tyr Thr Asn Asn Ser Leu Leu Lys Asp Ile Ile Asn Glu Tyr
    850                 855                 860

Phe Asn Asn Ile Asn Asp Ser Lys Ile Leu Ser Leu Gln Asn Arg Lys
865                 870                 875                 880

Asn Thr Leu Val Asp Thr Ser Gly Tyr Asn Ala Glu Val Ser Glu Glu
                885                 890                 895

Gly Asp Val Gln Leu Asn Pro Ile Phe Pro Phe Asp Phe Lys Leu Gly
            900                 905                 910

Ser Ser Gly Glu Asp Arg Gly Lys Val Ile Val Thr Gln Asn Glu Asn
        915                 920                 925

Ile Val Tyr Asn Ser Met Tyr Glu Ser Phe Ser Ile Ser Phe Trp Ile
    930                 935                 940

Arg Ile Asn Lys Trp Val Ser Asn Leu Pro Gly Tyr Thr Ile Ile Asp
945                 950                 955                 960

Ser Val Lys Asn Asn Ser Gly Trp Ser Ile Gly Ile Ile Ser Asn Phe
                965                 970                 975

Leu Val Phe Thr Leu Lys Gln Asn Glu Asp Ser Glu Gln Ser Ile Asn
            980                 985                 990

Phe Ser Tyr Asp Ile Ser Asn Asn Ala Pro Gly Tyr Asn Lys Trp Phe
        995                 1000                1005

Phe Val Thr Val Thr Asn Asn Met Met Gly Asn Met Lys Ile Tyr
    1010                1015                1020

Ile Asn Gly Lys Leu Ile Asp Thr Ile Lys Val Lys Glu Leu Thr
    1025                1030                1035

Gly Ile Asn Phe Ser Lys Thr Ile Thr Phe Glu Ile Asn Lys Ile
    1040                1045                1050

Pro Asp Thr Gly Leu Ile Thr Ser Asp Ser Asp Asn Ile Asn Met
    1055                1060                1065

Trp Ile Arg Asp Phe Tyr Ile Phe Ala Lys Glu Leu Asp Gly Lys
    1070                1075                1080

Asp Ile Asn Ile Leu Phe Asn Ser Leu Gln Tyr Thr Asn Val Val
```

-continued

```
                   1085                1090                1095

Lys Asp Tyr Trp Gly Asn Asp Leu Arg Tyr Asn Lys Glu Tyr Tyr
        1100                1105                1110

Met Val Asn Ile Asp Tyr Leu Asn Arg Tyr Met Tyr Ala Asn Ser
        1115                1120                1125

Arg Gln Ile Val Phe Asn Thr Arg Arg Asn Asn Asn Asp Phe Asn
        1130                1135                1140

Glu Gly Tyr Lys Ile Ile Ile Lys Arg Ile Arg Gly Asn Thr Asn
        1145                1150                1155

Asp Thr Arg Val Arg Gly Gly Asp Ile Leu Tyr Phe Asp Met Thr
        1160                1165                1170

Ile Asn Asn Lys Ala Tyr Asn Leu Phe Met Lys Asn Glu Thr Met
        1175                1180                1185

Tyr Ala Asp Asn His Ser Thr Glu Asp Ile Tyr Ala Ile Gly Leu
        1190                1195                1200

Arg Glu Gln Thr Lys Asp Ile Asn Asp Asn Ile Ile Phe Gln Ile
        1205                1210                1215

Gln Pro Met Asn Asn Thr Tyr Tyr Tyr Ala Ser Gln Ile Phe Lys
        1220                1225                1230

Ser Asn Phe Asn Gly Glu Asn Ile Ser Gly Ile Cys Ser Ile Gly
        1235                1240                1245

Thr Tyr Arg Phe Arg Leu Gly Gly Asp Trp Tyr Arg His Asn Tyr
        1250                1255                1260

Leu Val Pro Thr Val Lys Gln Gly Asn Tyr Ala Ser Leu Leu Glu
        1265                1270                1275

Ser Thr Ser Thr His Trp Gly Phe Val Pro Val Ser Glu
        1280                1285                1290

<210> SEQ ID NO 4
<211> LENGTH: 1276
<212> TYPE: PRT
<213> ORGANISM: C. botulinum

<400> SEQUENCE: 4

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
                20                  25                  30

Pro Val Lys Ala Phe Met Ile Thr Gln Asn Ile Trp Val Ile Pro Glu
            35                  40                  45

Arg Phe Ser Ser Asp Thr Asn Pro Ser Leu Ser Lys Pro Pro Arg Pro
        50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
                100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
        130                 135                 140

Ser Trp Lys Val Thr Asn Ile Ile Thr Pro Ser Val Leu Ile Phe Gly
145                 150                 155                 160
```

-continued

```
Pro Leu Pro Asn Ile Leu Asp Tyr Thr Ala Ser Leu Thr Leu Gln Gly
            165                 170                 175

Gln Gln Ser Asn Pro Ser Phe Glu Gly Phe Gly Thr Leu Ser Ile Leu
        180                 185                 190

Lys Val Ala Pro Glu Phe Leu Leu Thr Phe Ser Asp Val Thr Ser Asn
    195                 200                 205

Gln Ser Ser Ala Val Leu Gly Lys Ser Ile Phe Cys Met Asp Pro Val
210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
        355                 360                 365

Val Lys Asn Arg Thr His Tyr Phe Ser Arg His Tyr Leu Pro Val Phe
    370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Leu Arg Leu Thr Lys Asn Ser Arg Asp Asp Ser
        435                 440                 445

Thr Cys Ile Lys Val Lys Asn Asn Arg Leu Pro Tyr Val Ala Asp Lys
    450                 455                 460

Asp Ser Ile Ser Gln Glu Ile Phe Glu Asn Lys Ile Ile Thr Asp Glu
465                 470                 475                 480

Thr Asn Val Gln Asn Tyr Ser Asp Lys Phe Ser Leu Asp Glu Ser Ile
                485                 490                 495

Leu Asp Gly Gln Val Pro Ile Asn Pro Glu Ile Val Asp Pro Leu Leu
            500                 505                 510

Pro Asn Val Asn Met Glu Pro Leu Asn Leu Pro Gly Glu Glu Ile Val
        515                 520                 525

Phe Tyr Asp Asp Ile Thr Lys Tyr Val Asp Tyr Leu Asn Ser Tyr Tyr
    530                 535                 540

Tyr Leu Glu Ser Gln Lys Leu Ser Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
```

-continued

```
                580                 585                 590
Leu Phe Leu Asn Trp Ala Asn Glu Val Val Glu Asp Phe Thr Thr Asn
        595                 600                 605
Ile Met Lys Lys Asp Thr Leu Asp Lys Ile Ser Asp Val Ser Val Ile
610                 615                 620
Ile Pro Tyr Ile Gly Pro Ala Leu Asn Ile Gly Asn Ser Ala Leu Arg
625                 630                 635                 640
Gly Asn Phe Asn Gln Ala Phe Ala Thr Ala Gly Val Ala Phe Leu Leu
                645                 650                 655
Glu Gly Phe Pro Glu Phe Thr Ile Pro Ala Leu Gly Val Phe Thr Phe
            660                 665                 670
Tyr Ser Ser Ile Gln Glu Arg Glu Lys Ile Ile Lys Thr Ile Glu Asn
        675                 680                 685
Cys Leu Glu Gln Arg Val Lys Arg Trp Lys Asp Ser Tyr Gln Trp Met
    690                 695                 700
Val Ser Asn Trp Leu Ser Arg Ile Thr Thr Gln Phe Asn His Ile Asn
705                 710                 715                 720
Tyr Gln Met Tyr Asp Ser Leu Ser Tyr Gln Ala Asp Ala Ile Lys Ala
                725                 730                 735
Lys Ile Asp Leu Glu Tyr Lys Lys Tyr Ser Gly Ser Asp Lys Glu Asn
            740                 745                 750
Ile Lys Ser Gln Val Glu Asn Leu Lys Asn Ser Leu Asp Val Lys Ile
        755                 760                 765
Ser Glu Ala Met Asn Asn Ile Asn Lys Phe Ile Arg Glu Cys Ser Val
    770                 775                 780
Thr Tyr Leu Phe Lys Asn Met Leu Pro Lys Val Ile Asp Glu Leu Asn
785                 790                 795                 800
Lys Phe Asp Leu Arg Thr Lys Thr Glu Leu Ile Asn Leu Ile Asp Ser
                805                 810                 815
His Asn Ile Ile Leu Val Gly Glu Val Asp Arg Leu Lys Ala Lys Val
            820                 825                 830
Asn Glu Ser Phe Glu Asn Thr Met Pro Phe Asn Ile Phe Ser Tyr Thr
        835                 840                 845
Asn Asn Ser Leu Leu Lys Asp Ile Ile Asn Glu Tyr Phe Asn Ser Ile
    850                 855                 860
Asn Asp Ser Lys Ile Leu Ser Leu Gln Asn Lys Lys Asn Ala Leu Val
865                 870                 875                 880
Asp Thr Ser Gly Tyr Asn Ala Glu Val Arg Val Gly Asp Asn Val Gln
                885                 890                 895
Leu Asn Thr Ile Tyr Thr Asn Asp Phe Lys Leu Ser Ser Ser Gly Asp
            900                 905                 910
Lys Ile Ile Val Asn Leu Asn Asn Ile Leu Tyr Ser Ala Ile Tyr
        915                 920                 925
Glu Asn Ser Ser Val Ser Phe Trp Ile Lys Ile Ser Lys Asp Leu Thr
    930                 935                 940
Asn Ser His Asn Glu Tyr Thr Ile Ile Asn Ser Ile Glu Gln Asn Ser
945                 950                 955                 960
Gly Trp Lys Leu Cys Ile Arg Asn Gly Asn Ile Glu Trp Ile Leu Gln
                965                 970                 975
Asp Val Asn Arg Lys Tyr Lys Ser Leu Ile Phe Asp Tyr Ser Glu Ser
            980                 985                 990
Leu Ser His Thr Gly Tyr Thr Asn  Lys Trp Phe Phe Val  Thr Ile Thr
        995                 1000                1005
```

```
Asn Asn Ile Met Gly Tyr Met Lys Leu Tyr Ile Asn Gly Glu Leu
    1010                1015                1020

Lys Gln Ser Gln Lys Ile Glu Asp Leu Asp Glu Val Lys Leu Asp
    1025                1030                1035

Lys Thr Ile Val Phe Gly Ile Asp Glu Asn Ile Asp Glu Asn Gln
    1040                1045                1050

Met Leu Trp Ile Arg Asp Phe Asn Ile Phe Ser Lys Glu Leu Ser
    1055                1060                1065

Asn Glu Asp Ile Asn Ile Val Tyr Glu Gly Gln Ile Leu Arg Asn
    1070                1075                1080

Val Ile Lys Asp Tyr Trp Gly Asn Pro Leu Lys Phe Asp Thr Glu
    1085                1090                1095

Tyr Tyr Ile Ile Asn Asp Asn Tyr Ile Asp Arg Tyr Ile Ala Pro
    1100                1105                1110

Glu Ser Asn Val Leu Val Leu Val Gln Tyr Pro Asp Arg Ser Lys
    1115                1120                1125

Leu Tyr Thr Gly Asn Pro Ile Thr Ile Lys Ser Val Ser Asp Lys
    1130                1135                1140

Asn Pro Tyr Ser Arg Ile Leu Asn Gly Asp Asn Ile Ile Leu His
    1145                1150                1155

Met Leu Tyr Asn Ser Arg Lys Tyr Met Ile Ile Arg Asp Thr Asp
    1160                1165                1170

Thr Ile Tyr Ala Thr Gln Gly Gly Glu Cys Ser Gln Asn Cys Val
    1175                1180                1185

Tyr Ala Leu Lys Leu Gln Ser Asn Leu Gly Asn Tyr Gly Ile Gly
    1190                1195                1200

Ile Phe Ser Ile Lys Asn Ile Val Ser Lys Asn Lys Tyr Cys Ser
    1205                1210                1215

Gln Ile Phe Ser Ser Phe Arg Glu Asn Thr Met Leu Leu Ala Asp
    1220                1225                1230

Ile Tyr Lys Pro Trp Arg Phe Ser Phe Lys Asn Ala Tyr Thr Pro
    1235                1240                1245

Val Ala Val Thr Asn Tyr Glu Thr Lys Leu Leu Ser Thr Ser Ser
    1250                1255                1260

Phe Trp Lys Phe Ile Ser Arg Asp Pro Gly Trp Val Glu
    1265                1270                1275

<210> SEQ ID NO 5
<211> LENGTH: 1252
<212> TYPE: PRT
<213> ORGANISM: C. botuilnum

<400> SEQUENCE: 5

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
```

-continued

```
                85                  90                  95
Asn Leu Ser Gly Gly Ile Leu Leu Glu Glu Leu Ser Lys Ala Asn Pro
            100                 105                 110
Tyr Leu Gly Asn Asp Asn Thr Pro Asp Asn Gln Phe His Ile Gly Asp
        115                 120                 125
Ala Ser Ala Val Glu Ile Lys Phe Ser Asn Gly Ser Gln Asp Ile Leu
    130                 135                 140
Leu Pro Asn Val Ile Ile Met Gly Ala Glu Pro Asp Leu Phe Glu Thr
145                 150                 155                 160
Asn Ser Ser Asn Ile Ser Leu Arg Asn Asn Tyr Met Pro Ser Asn His
                165                 170                 175
Gly Phe Gly Ser Ile Ala Ile Val Thr Phe Ser Pro Glu Tyr Ser Phe
            180                 185                 190
Arg Phe Asn Asp Asn Ser Met Asn Glu Phe Ile Gln Asp Pro Ala Leu
        195                 200                 205
Thr Leu Met His Glu Leu Ile His Ser Leu His Gly Leu Tyr Gly Ala
    210                 215                 220
Lys Gly Ile Thr Thr Lys Tyr Thr Ile Thr Gln Lys Gln Asn Pro Leu
225                 230                 235                 240
Ile Thr Asn Ile Arg Gly Thr Asn Ile Glu Glu Phe Leu Thr Phe Gly
                245                 250                 255
Gly Thr Asp Leu Asn Ile Ile Thr Ser Ala Gln Ser Asn Asp Ile Tyr
            260                 265                 270
Thr Asn Leu Leu Ala Asp Tyr Lys Lys Ile Ala Ser Lys Leu Ser Lys
        275                 280                 285
Val Gln Val Ser Asn Pro Leu Leu Asn Pro Tyr Lys Asp Val Phe Glu
    290                 295                 300
Ala Lys Tyr Gly Leu Asp Lys Asp Ala Ser Gly Ile Tyr Ser Val Asn
305                 310                 315                 320
Ile Asn Lys Phe Asn Asp Ile Phe Lys Lys Leu Tyr Ser Phe Thr Glu
                325                 330                 335
Phe Asp Leu Ala Thr Lys Phe Gln Val Lys Cys Arg Gln Thr Tyr Ile
            340                 345                 350
Gly Gln Tyr Lys Tyr Phe Lys Leu Ser Asn Leu Leu Asn Asp Ser Ile
        355                 360                 365
Tyr Asn Ile Ser Glu Gly Tyr Asn Ile Asn Asn Leu Lys Val Asn Phe
    370                 375                 380
Arg Gly Gln Asn Ala Asn Leu Asn Pro Arg Ile Ile Thr Pro Ile Thr
385                 390                 395                 400
Gly Arg Gly Leu Val Lys Lys Ile Ile Arg Phe Cys Lys Asn Ile Val
                405                 410                 415
Ser Val Lys Gly Ile Arg Lys Ser Ile Cys Ile Glu Ile Asn Asn Gly
            420                 425                 430
Glu Leu Phe Phe Val Ala Ser Glu Asn Ser Tyr Asn Asp Asp Asn Ile
        435                 440                 445
Asn Thr Pro Lys Glu Ile Asp Asp Thr Val Thr Ser Asn Asn Asn Tyr
    450                 455                 460
Glu Asn Asp Leu Asp Gln Val Ile Leu Asn Phe Asn Ser Glu Ser Ala
465                 470                 475                 480
Pro Gly Leu Ser Asp Glu Lys Leu Asn Leu Thr Ile Gln Asn Asp Ala
                485                 490                 495
Tyr Ile Pro Lys Tyr Asp Ser Asn Gly Thr Ser Asp Ile Glu Gln His
            500                 505                 510
```

-continued

```
Asp Val Asn Glu Leu Asn Val Phe Phe Tyr Leu Asp Ala Gln Lys Val
            515                 520                 525
Pro Glu Gly Glu Asn Asn Val Asn Leu Thr Ser Ser Ile Asp Thr Ala
        530                 535                 540
Leu Leu Glu Gln Pro Lys Ile Tyr Thr Phe Phe Ser Ser Glu Phe Ile
545                 550                 555                 560
Asn Asn Val Asn Lys Pro Val Gln Ala Ala Leu Phe Val Ser Trp Ile
                565                 570                 575
Gln Gln Val Leu Val Asp Phe Thr Thr Glu Ala Asn Gln Lys Ser Thr
            580                 585                 590
Val Asp Lys Ile Ala Asp Ile Ser Ile Val Val Pro Tyr Ile Gly Leu
        595                 600                 605
Ala Leu Asn Ile Gly Asn Glu Ala Gln Lys Gly Asn Phe Lys Asp Ala
    610                 615                 620
Leu Glu Leu Leu Gly Ala Gly Ile Leu Leu Glu Phe Glu Pro Glu Leu
625                 630                 635                 640
Leu Ile Pro Thr Ile Leu Val Phe Thr Ile Lys Ser Phe Leu Gly Ser
                645                 650                 655
Ser Asp Asn Lys Asn Lys Val Ile Lys Ala Ile Asn Asn Ala Leu Lys
            660                 665                 670
Glu Arg Asp Glu Lys Trp Lys Glu Val Tyr Ser Phe Ile Val Ser Asn
        675                 680                 685
Trp Met Thr Lys Ile Asn Thr Gln Phe Asn Lys Arg Lys Glu Gln Met
    690                 695                 700
Tyr Gln Ala Leu Gln Asn Gln Val Asn Ala Ile Lys Thr Ile Ile Glu
705                 710                 715                 720
Ser Lys Tyr Asn Ser Tyr Thr Leu Glu Glu Lys Asn Glu Leu Thr Asn
                725                 730                 735
Lys Tyr Asp Ile Lys Gln Ile Glu Asn Glu Leu Asn Gln Lys Val Ser
            740                 745                 750
Ile Ala Met Asn Asn Ile Asp Arg Phe Leu Thr Glu Ser Ser Ile Ser
        755                 760                 765
Tyr Leu Met Lys Leu Ile Asn Glu Val Lys Ile Asn Lys Leu Arg Glu
    770                 775                 780
Tyr Asp Glu Asn Val Lys Thr Tyr Leu Leu Asn Tyr Ile Ile Gln His
785                 790                 795                 800
Gly Ser Ile Leu Gly Glu Ser Gln Gln Glu Leu Asn Ser Met Val Thr
                805                 810                 815
Asp Thr Leu Asn Asn Ser Ile Pro Phe Lys Leu Ser Ser Tyr Thr Asp
            820                 825                 830
Asp Lys Ile Leu Ile Ser Tyr Phe Asn Lys Phe Phe Lys Arg Ile Lys
        835                 840                 845
Ser Ser Ser Val Leu Asn Met Arg Tyr Lys Asn Asp Lys Tyr Val Asp
    850                 855                 860
Thr Ser Gly Tyr Asp Ser Asn Ile Asn Ile Asn Gly Asp Val Tyr Lys
865                 870                 875                 880
Tyr Pro Thr Asn Lys Asn Gln Phe Gly Ile Tyr Asn Asp Lys Leu Ser
                885                 890                 895
Glu Val Asn Ile Ser Gln Asn Asp Tyr Ile Ile Tyr Asp Asn Lys Tyr
            900                 905                 910
Lys Asn Phe Ser Ile Ser Phe Trp Val Arg Ile Pro Asn Tyr Asp Asn
        915                 920                 925
```

Lys Ile Val Asn Val Asn Glu Tyr Thr Ile Ile Asn Cys Met Arg
           930                 935                 940

Asp Asn Asn Ser Gly Trp Lys Val Ser Leu Asn His Asn Glu Ile Ile
945                 950                 955                 960

Trp Thr Leu Gln Asp Asn Ala Gly Ile Asn Gln Lys Leu Ala Phe Asn
                965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu Gly Asp Ser Lys Leu Tyr Ile Asn
        995                 1000                1005

Gly Asn Leu Ile Asp Gln Lys Ser Ile Leu Asn Leu Gly Asn Ile
    1010                1015                1020

His Val Ser Asp Asn Ile Leu Phe Lys Ile Val Asn Cys Ser Tyr
    1025                1030                1035

Thr Arg Tyr Ile Gly Ile Arg Tyr Phe Asn Ile Phe Asp Lys Glu
    1040                1045                1050

Leu Asp Glu Thr Glu Ile Gln Thr Leu Tyr Ser Asn Glu Pro Asn
    1055                1060                1065

Thr Asn Ile Leu Lys Asp Phe Trp Gly Asn Tyr Leu Leu Tyr Asp
    1070                1075                1080

Lys Glu Tyr Tyr Leu Leu Asn Val Leu Lys Pro Asn Asn Phe Ile
    1085                1090                1095

Asp Arg Arg Lys Asp Ser Thr Leu Ser Ile Asn Asn Ile Arg Ser
    1100                1105                1110

Thr Ile Leu Leu Ala Asn Arg Leu Tyr Ser Gly Ile Lys Val Lys
    1115                1120                1125

Ile Gln Arg Val Asn Asn Ser Ser Thr Asn Asp Asn Leu Val Arg
    1130                1135                1140

Lys Asn Asp Gln Val Tyr Ile Asn Phe Val Ala Ser Lys Thr His
    1145                1150                1155

Leu Phe Pro Leu Tyr Ala Asp Thr Ala Thr Thr Asn Lys Glu Lys
    1160                1165                1170

Thr Ile Lys Ile Ser Ser Ser Gly Asn Arg Phe Asn Gln Val Val
    1175                1180                1185

Val Met Asn Ser Val Gly Asn Asn Cys Thr Met Asn Phe Lys Asn
    1190                1195                1200

Asn Asn Gly Asn Asn Ile Gly Leu Leu Gly Phe Lys Ala Asp Thr
    1205                1210                1215

Val Val Ala Ser Thr Trp Tyr Tyr Thr His Met Arg Asp His Thr
    1220                1225                1230

Asn Ser Asn Gly Cys Phe Trp Asn Phe Ile Ser Glu Glu His Gly
    1235                1240                1245

Trp Gln Glu Lys
    1250

<210> SEQ ID NO 6
<211> LENGTH: 1274
<212> TYPE: PRT
<213> ORGANISM: C. botulinum

<400> SEQUENCE: 6

Met Pro Val Ala Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

```
Tyr Tyr Lys Ala Phe Glu Ile Met Arg Asn Val Trp Ile Ile Pro Glu
         35                  40                  45

Arg Asn Thr Ile Gly Thr Asn Pro Ser Asp Phe Asp Pro Pro Ala Ser
 50                  55                  60

Leu Lys Asn Gly Ser Ser Ala Tyr Tyr Asp Pro Asn Tyr Leu Thr Thr
 65                  70                  75                  80

Asp Ala Glu Lys Asp Arg Tyr Leu Lys Thr Thr Ile Lys Leu Phe Lys
                 85                  90                  95

Arg Ile Asn Ser Asn Pro Ala Gly Lys Val Leu Leu Gln Glu Ile Ser
            100                 105                 110

Tyr Ala Lys Pro Tyr Leu Gly Asn Asp His Thr Pro Ile Asp Glu Phe
        115                 120                 125

Ser Pro Val Thr Arg Thr Ser Val Asn Ile Lys Leu Ser Thr Asn
    130                 135                 140

Val Glu Ser Ser Met Leu Leu Asn Leu Val Leu Gly Ala Gly Pro
145                 150                 155                 160

Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Glu Glu Thr Ile Glu Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Glu Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ser Asp Leu Ala Asn Lys Phe Lys Val Lys Cys Arg Asn Thr Tyr
        355                 360                 365

Phe Ile Lys Tyr Glu Phe Leu Lys Val Pro Asn Leu Leu Asp Asp
    370                 375                 380

Ile Tyr Thr Val Ser Glu Gly Phe Asn Ile Gly Asn Leu Ala Val Asn
385                 390                 395                 400

Asn Arg Gly Gln Ser Ile Lys Leu Asn Pro Lys Ile Ile Asp Ser Ile
                405                 410                 415

Pro Asp Lys Gly Leu Val Glu Lys Ile Val Lys Phe Cys Lys Ser Val
            420                 425                 430

Ile Pro Arg Lys Gly Thr Lys Ala Pro Pro Arg Leu Cys Ile Arg Val
        435                 440                 445
```

```
Asn Asn Ser Glu Leu Phe Phe Val Ala Ser Glu Ser Ser Tyr Asn Glu
    450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Gln Thr Ile Pro Gln Ile Ser Asn Arg Thr Leu Asn Thr Leu Val Gln
                500                 505                 510

Asp Asn Ser Tyr Val Pro Arg Tyr Asp Ser Asn Gly Thr Ser Glu Ile
            515                 520                 525

Glu Glu Tyr Asp Val Val Asp Phe Asn Val Phe Phe Tyr Leu His Ala
    530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Asp Ile Phe Phe Ser Ser Glu
                565                 570                 575

Phe Ile Asp Thr Ile Asn Lys Pro Val Asn Ala Ala Leu Phe Ile Asp
                580                 585                 590

Trp Ile Ser Lys Val Ile Arg Asp Phe Thr Thr Glu Ala Thr Gln Lys
            595                 600                 605

Ser Thr Val Asp Lys Ile Ala Asp Ile Ser Leu Ile Val Pro Tyr Val
    610                 615                 620

Gly Leu Ala Leu Asn Ile Ile Glu Ala Glu Lys Gly Asn Phe Glu
625                 630                 635                 640

Glu Ala Phe Glu Leu Leu Gly Val Gly Ile Leu Leu Glu Phe Val Pro
                645                 650                 655

Glu Leu Thr Ile Pro Val Ile Leu Val Phe Thr Ile Lys Ser Tyr Ile
                660                 665                 670

Asp Ser Tyr Glu Asn Lys Asn Lys Ala Ile Lys Ala Ile Asn Asn Ser
            675                 680                 685

Leu Ile Glu Arg Glu Ala Lys Trp Lys Glu Ile Tyr Ser Trp Ile Val
    690                 695                 700

Ser Asn Trp Leu Thr Arg Ile Asn Thr Gln Phe Asn Lys Arg Lys Glu
705                 710                 715                 720

Gln Met Tyr Gln Ala Leu Gln Asn Gln Val Asp Ala Ile Lys Thr Ala
                725                 730                 735

Ile Glu Tyr Lys Tyr Asn Asn Tyr Thr Ser Asp Glu Lys Asn Arg Leu
                740                 745                 750

Glu Ser Glu Tyr Asn Ile Asn Asn Ile Glu Glu Glu Leu Asn Lys Lys
            755                 760                 765

Val Ser Leu Ala Met Lys Asn Ile Glu Arg Phe Met Thr Glu Ser Ser
    770                 775                 780

Ile Ser Tyr Leu Met Lys Leu Ile Asn Glu Ala Lys Val Gly Lys Leu
785                 790                 795                 800

Lys Lys Tyr Asp Asn His Val Lys Ser Asp Leu Leu Asn Tyr Ile Leu
                805                 810                 815

Asp His Arg Ser Ile Leu Gly Glu Gln Thr Asn Glu Leu Ser Asp Leu
                820                 825                 830

Val Thr Ser Thr Leu Asn Ser Ser Ile Pro Phe Glu Leu Ser Ser Tyr
            835                 840                 845

Thr Asn Asp Lys Ile Leu Ile Ile Tyr Phe Asn Arg Leu Tyr Lys Lys
    850                 855                 860

Ile Lys Asp Ser Ser Ile Leu Asp Met Arg Tyr Glu Asn Asn Lys Phe
```

-continued

```
            865                 870                 875                 880
        Ile Asp Ile Ser Gly Tyr Gly Ser Asn Ile Ser Ile Asn Gly Asn Val
                        885                 890                 895
        Tyr Ile Tyr Ser Thr Asn Arg Asn Gln Phe Gly Ile Tyr Asn Ser Arg
                        900                 905                 910
        Leu Ser Glu Val Asn Ile Ala Gln Asn Asn Asp Ile Ile Tyr Asn Ser
                        915                 920                 925
        Arg Tyr Gln Asn Phe Ser Ile Ser Phe Trp Val Arg Ile Pro Lys His
            930                 935                 940
        Tyr Lys Pro Met Asn His Asn Arg Glu Tyr Thr Ile Ile Asn Cys Met
        945                 950                 955                 960
        Gly Asn Asn Asn Ser Gly Trp Lys Ile Ser Leu Arg Thr Val Arg Asp
                        965                 970                 975
        Cys Glu Ile Ile Trp Thr Leu Gln Asp Thr Ser Gly Asn Lys Glu Asn
                        980                 985                 990
        Leu Ile Phe Arg Tyr Glu Glu Leu Asn Arg Ile Ser Asn Tyr Ile Asn
                        995                1000                1005
        Lys Trp Ile Phe Val Thr Ile Thr Asn Asn Arg Leu Gly Asn Ser
            1010                1015                1020
        Arg Ile Tyr Ile Asn Gly Asn Leu Ile Val Glu Lys Ser Ile Ser
            1025                1030                1035
        Asn Leu Gly Asp Ile His Val Ser Asp Asn Ile Leu Phe Lys Ile
            1040                1045                1050
        Val Gly Cys Asp Asp Glu Thr Tyr Val Gly Ile Arg Tyr Phe Lys
            1055                1060                1065
        Val Phe Asn Thr Glu Leu Asp Lys Thr Glu Ile Glu Thr Leu Tyr
            1070                1075                1080
        Ser Asn Glu Pro Asp Pro Ser Ile Leu Lys Asn Tyr Trp Gly Asn
            1085                1090                1095
        Tyr Leu Leu Tyr Asn Lys Lys Tyr Tyr Leu Phe Asn Leu Leu Arg
            1100                1105                1110
        Lys Asp Lys Tyr Ile Thr Leu Asn Ser Gly Ile Leu Asn Ile Asn
            1115                1120                1125
        Gln Gln Arg Gly Val Thr Glu Gly Ser Val Phe Leu Asn Tyr Lys
            1130                1135                1140
        Leu Tyr Glu Gly Val Glu Val Ile Ile Arg Lys Asn Gly Pro Ile
            1145                1150                1155
        Asp Ile Ser Asn Thr Asp Asn Phe Val Arg Lys Asn Asp Leu Ala
            1160                1165                1170
        Tyr Ile Asn Val Val Asp Arg Gly Val Glu Tyr Arg Leu Tyr Ala
            1175                1180                1185
        Asp Thr Lys Ser Glu Lys Glu Lys Ile Ile Arg Thr Ser Asn Leu
            1190                1195                1200
        Asn Asp Ser Leu Gly Gln Ile Ile Val Met Asp Ser Ile Gly Asn
            1205                1210                1215
        Asn Cys Thr Met Asn Phe Gln Asn Asn Asn Gly Ser Asn Ile Gly
            1220                1225                1230
        Leu Leu Gly Phe His Ser Asn Asn Leu Val Ala Ser Ser Trp Tyr
            1235                1240                1245
        Tyr Asn Asn Ile Arg Arg Asn Thr Ser Ser Asn Gly Cys Phe Trp
            1250                1255                1260
        Ser Ser Ile Ser Lys Glu Asn Gly Trp Lys Glu
            1265                1270
```

<210> SEQ ID NO 7
<211> LENGTH: 1297
<212> TYPE: PRT
<213> ORGANISM: C. botulinum

<400> SEQUENCE: 7

```
Met Pro Val Asn Ile Lys Asn Phe Asn Tyr Asn Asp Pro Ile Asn Asn
1               5                   10                  15

Asp Asp Ile Ile Met Met Glu Pro Phe Asn Asp Pro Gly Pro Gly Thr
            20                  25                  30

Tyr Tyr Lys Ala Phe Arg Ile Ile Asp Arg Ile Trp Ile Val Pro Glu
        35                  40                  45

Arg Phe Thr Tyr Gly Phe Gln Pro Asp Gln Phe Asn Ala Ser Thr Gly
50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
        275                 280                 285

Tyr Asn Lys Ala Leu Gln Asn Phe Gln Asp Ile Ala Asn Arg Leu Asn
290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
        355                 360                 365

Arg Tyr Ser Tyr Phe Ser Glu Tyr Leu Pro Pro Ile Lys Thr Glu Lys
```

```
              370                 375                 380
Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
                420                 425                 430

Ile Ala Met Cys Lys Pro Val Met Tyr Lys Asn Thr Gly Lys Ser Glu
                435                 440                 445

Gln Cys Ile Ile Val Asn Asn Glu Asp Leu Phe Phe Ile Ala Asn Lys
                450                 455                 460

Asp Ser Phe Ser Lys Asp Leu Ala Lys Ala Glu Thr Ile Ala Tyr Asn
465                 470                 475                 480

Thr Gln Asn Asn Thr Ile Glu Asn Asn Phe Ser Ile Asp Gln Leu Ile
                485                 490                 495

Leu Asp Asn Asp Leu Ser Ser Gly Ile Asp Leu Pro Asn Glu Asn Thr
                500                 505                 510

Glu Pro Phe Thr Asn Phe Asp Asp Ile Asp Ile Pro Val Tyr Ile Lys
                515                 520                 525

Gln Ser Ala Leu Lys Lys Ile Phe Val Asp Gly Asp Ser Leu Phe Glu
                530                 535                 540

Tyr Leu His Ala Gln Thr Phe Pro Ser Asn Ile Glu Asn Leu Gln Leu
545                 550                 555                 560

Thr Asn Ser Leu Asn Asp Ala Leu Arg Asn Asn Asn Lys Val Tyr Thr
                565                 570                 575

Phe Phe Ser Thr Asn Leu Val Glu Lys Ala Asn Thr Val Val Gly Ala
                580                 585                 590

Ser Leu Phe Val Asn Trp Val Lys Gly Val Ile Asp Asp Phe Thr Ser
                595                 600                 605

Glu Ser Thr Gln Lys Ser Thr Ile Asp Lys Val Ser Asp Val Ser Ile
                610                 615                 620

Ile Ile Pro Tyr Ile Gly Pro Ala Leu Asn Val Gly Asn Glu Thr Ala
625                 630                 635                 640

Lys Glu Asn Phe Lys Asn Ala Phe Glu Ile Gly Gly Ala Ala Ile Leu
                645                 650                 655

Met Glu Phe Ile Pro Glu Leu Ile Val Pro Ile Val Gly Phe Phe Thr
                660                 665                 670

Leu Glu Ser Tyr Val Gly Asn Lys Gly His Ile Ile Met Thr Ile Ser
                675                 680                 685

Asn Ala Leu Lys Lys Arg Asp Gln Lys Trp Thr Asp Met Tyr Gly Leu
                690                 695                 700

Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
                725                 730                 735

Lys Ile Ile Glu Asp Gln Tyr Asn Arg Tyr Ser Glu Glu Asp Lys Met
                740                 745                 750

Asn Ile Asn Ile Asp Phe Asn Asp Ile Asp Phe Lys Leu Asn Gln Ser
                755                 760                 765

Ile Asn Leu Ala Ile Asn Asn Ile Asp Asp Phe Ile Asn Gln Cys Ser
                770                 775                 780

Ile Ser Tyr Leu Met Asn Arg Met Ile Pro Leu Ala Val Lys Lys Leu
785                 790                 795                 800
```

-continued

```
Lys Asp Phe Asp Asp Asn Leu Lys Arg Asp Leu Leu Glu Tyr Ile Asp
                805                 810                 815

Thr Asn Glu Leu Tyr Leu Leu Asp Glu Val Asn Ile Leu Lys Ser Lys
            820                 825                 830

Val Asn Arg His Leu Lys Asp Ser Ile Pro Phe Asp Leu Ser Leu Tyr
            835                 840                 845

Thr Lys Asp Thr Ile Leu Ile Gln Val Phe Asn Asn Tyr Ile Ser Asn
    850                 855                 860

Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
                885                 890                 895

Ile Phe Asn Asp Ile Gly Asn Gly Gln Phe Lys Leu Asn Asn Ser Glu
                900                 905                 910

Asn Ser Asn Ile Thr Ala His Gln Ser Lys Phe Val Val Tyr Asp Ser
                915                 920                 925

Met Phe Asp Asn Phe Ser Ile Asn Phe Trp Val Arg Thr Pro Lys Tyr
    930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
                965                 970                 975

Arg Ile Ile Trp Thr Leu Ile Asp Val Asn Ala Lys Ser Lys Ser Ile
                980                 985                 990

Phe Phe Glu Tyr Ser Ile Lys Asp Asn Ile Ser Asp Tyr Ile Asn Lys
                995                1000                1005

Trp Phe Ser Ile Thr Ile Thr Asn Asp Arg Leu Gly Asn Ala Asn
    1010                1015                1020

Ile Tyr Ile Asn Gly Ser Leu Lys Lys Ser Glu Lys Ile Leu Asn
    1025                1030                1035

Leu Asp Arg Ile Asn Ser Ser Asn Asp Ile Asp Phe Lys Leu Ile
    1040                1045                1050

Asn Cys Thr Asp Thr Thr Lys Phe Val Trp Ile Lys Asp Phe Asn
    1055                1060                1065

Ile Phe Gly Arg Glu Leu Asn Ala Thr Glu Val Ser Ser Leu Tyr
    1070                1075                1080

Trp Ile Gln Ser Ser Thr Asn Thr Leu Lys Asp Phe Trp Gly Asn
    1085                1090                1095

Pro Leu Arg Tyr Asp Thr Gln Tyr Tyr Leu Phe Asn Gln Gly Met
    1100                1105                1110

Gln Asn Ile Tyr Ile Lys Tyr Phe Ser Lys Ala Ser Met Gly Glu
    1115                1120                1125

Thr Ala Pro Arg Thr Asn Phe Asn Asn Ala Ala Ile Asn Tyr Gln
    1130                1135                1140

Asn Leu Tyr Leu Gly Leu Arg Phe Ile Ile Lys Lys Ala Ser Asn
    1145                1150                1155

Ser Arg Asn Ile Asn Asn Asp Asn Ile Val Arg Glu Gly Asp Tyr
    1160                1165                1170

Ile Tyr Leu Asn Ile Asp Asn Ile Ser Asp Glu Ser Tyr Arg Val
    1175                1180                1185

Tyr Val Leu Val Asn Ser Lys Glu Ile Gln Thr Gln Leu Phe Leu
    1190                1195                1200
```

-continued

Ala Pro Ile Asn Asp Asp Pro Thr Phe Tyr Asp Val Leu Gln Ile
1205                1210                1215

Lys Lys Tyr Tyr Glu Lys Thr Thr Tyr Asn Cys Gln Ile Leu Cys
    1220                1225                1230

Glu Lys Asp Thr Lys Thr Phe Gly Leu Phe Gly Ile Gly Lys Phe
    1235                1240                1245

Val Lys Asp Tyr Gly Tyr Val Trp Asp Thr Tyr Asp Asn Tyr Phe
    1250                1255                1260

Cys Ile Ser Gln Trp Tyr Leu Arg Arg Ile Ser Glu Asn Ile Asn
    1265                1270                1275

Lys Leu Arg Leu Gly Cys Asn Trp Gln Phe Ile Pro Val Asp Glu
    1280                1285                1290

Gly Trp Thr Glu
    1295

<210> SEQ ID NO 8
<211> LENGTH: 1315
<212> TYPE: PRT
<213> ORGANISM: C. botulinum

<400> SEQUENCE: 8

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
                20                  25                  30

Tyr Tyr Lys Ala Phe Lys Ile Thr Asp Arg Ile Trp Ile Val Pro Glu
            35                  40                  45

Arg Tyr Glu Phe Gly Thr Lys Pro Glu Asp Phe Asn Pro Pro Ser Ser
        50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
                100                 105                 110

Asn Ala Ile Pro Tyr Leu Gly Asn Ser Tyr Ser Leu Leu Asp Lys Phe
            115                 120                 125

Asp Thr Asn Ser Asn Ser Val Ser Phe Asn Leu Leu Glu Gln Asp Pro
        130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
                180                 185                 190

Ile Met Gln Met Ala Phe Cys Pro Glu Tyr Val Pro Thr Phe Asp Asn
            195                 200                 205

Val Ile Glu Asn Ile Thr Ser Leu Thr Ile Gly Lys Ser Lys Tyr Phe
        210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

```
Phe Thr Phe Gly Gly Gln Asp Ala Asn Leu Ile Ser Ile Asp Ile Lys
            275                 280                 285
Asn Asp Leu Tyr Glu Lys Thr Leu Asn Asp Tyr Lys Ala Ile Ala Asn
        290                 295                 300
Lys Leu Ser Gln Val Thr Ser Cys Asn Asp Pro Asn Ile Asp Ile Asp
305                 310                 315                 320
Ser Tyr Lys Gln Ile Tyr Gln Gln Lys Tyr Gln Phe Asp Lys Asp Ser
                    325                 330                 335
Asn Gly Gln Tyr Ile Val Asn Glu Asp Lys Phe Gln Ile Leu Tyr Asn
                340                 345                 350
Ser Ile Met Tyr Gly Phe Thr Glu Ile Glu Leu Gly Lys Lys Phe Asn
            355                 360                 365
Ile Lys Thr Arg Leu Ser Tyr Phe Ser Met Asn His Asp Pro Val Lys
        370                 375                 380
Ile Pro Asn Leu Leu Asp Asp Thr Ile Tyr Asn Asp Thr Glu Gly Phe
385                 390                 395                 400
Asn Ile Glu Ser Lys Asp Leu Lys Ser Glu Tyr Lys Gly Gln Asn Met
                    405                 410                 415
Arg Val Asn Thr Asn Ala Phe Arg Asn Val Asp Gly Ser Gly Leu Val
                420                 425                 430
Ser Lys Leu Ile Gly Leu Cys Lys Lys Ile Ile Pro Pro Thr Asn Ile
            435                 440                 445
Arg Glu Asn Leu Tyr Asn Arg Thr Ala Ser Leu Thr Asp Leu Gly Gly
        450                 455                 460
Glu Leu Cys Ile Lys Ile Lys Asn Glu Asp Leu Thr Phe Ile Ala Glu
465                 470                 475                 480
Lys Asn Ser Phe Ser Glu Glu Pro Phe Gln Asp Glu Ile Val Ser Tyr
                    485                 490                 495
Asn Thr Lys Asn Lys Pro Leu Asn Phe Asn Tyr Ser Leu Asp Lys Ile
                500                 505                 510
Ile Val Asp Tyr Asn Leu Gln Ser Lys Ile Thr Leu Pro Asn Asp Arg
            515                 520                 525
Thr Thr Pro Val Thr Lys Gly Ile Pro Tyr Ala Pro Glu Tyr Lys Ser
        530                 535                 540
Asn Ala Ala Ser Thr Ile Glu Ile His Asn Ile Asp Asp Asn Thr Ile
545                 550                 555                 560
Tyr Gln Tyr Leu Tyr Ala Gln Lys Ser Pro Thr Thr Leu Gln Arg Ile
                    565                 570                 575
Thr Met Thr Asn Ser Val Asp Asp Ala Leu Ile Asn Ser Thr Lys Ile
                580                 585                 590
Tyr Ser Tyr Phe Pro Ser Val Ile Ser Lys Val Asn Gln Gly Ala Gln
            595                 600                 605
Gly Ile Leu Phe Leu Gln Trp Val Arg Asp Ile Asp Asp Phe Thr
        610                 615                 620
Asn Glu Ser Ser Gln Lys Thr Thr Ile Asp Lys Ile Ser Asp Val Ser
625                 630                 635                 640
Thr Ile Val Pro Tyr Ile Gly Pro Ala Leu Asn Ile Val Lys Gln Gly
                    645                 650                 655
Tyr Glu Gly Asn Phe Ile Gly Ala Leu Glu Thr Gly Val Val Leu
                660                 665                 670
Leu Leu Glu Tyr Ile Pro Glu Ile Thr Leu Pro Val Ile Ala Ala Leu
            675                 680                 685
```

-continued

```
Ser Ile Ala Glu Ser Ser Thr Gln Lys Glu Lys Ile Ile Lys Thr Ile
    690             695                 700
Asp Asn Phe Leu Glu Lys Arg Tyr Glu Lys Trp Ile Glu Val Tyr Lys
705                 710                 715                 720
Leu Val Lys Ala Lys Trp Leu Gly Thr Val Asn Thr Gln Phe Gln Lys
                725                 730                 735
Arg Ser Tyr Gln Met Tyr Arg Ser Leu Glu Tyr Gln Val Asp Ala Ile
                740                 745                 750
Lys Lys Ile Ile Asp Tyr Glu Tyr Lys Ile Tyr Ser Gly Pro Asp Lys
            755                 760                 765
Glu Gln Ile Ala Asp Glu Ile Asn Asn Leu Lys Asn Lys Leu Glu Glu
            770                 775                 780
Lys Ala Asn Lys Ala Met Ile Asn Ile Asn Ile Phe Met Arg Glu Ser
785                 790                 795                 800
Ser Arg Ser Phe Leu Val Asn Gln Met Ile Asn Glu Ala Lys Lys Gln
                805                 810                 815
Leu Leu Glu Phe Asp Thr Gln Ser Lys Asn Ile Leu Met Gln Tyr Ile
                820                 825                 830
Lys Ala Asn Ser Lys Phe Ile Gly Ile Thr Glu Leu Lys Lys Leu Glu
            835                 840                 845
Ser Lys Ile Asn Lys Val Phe Ser Thr Pro Ile Pro Phe Ser Tyr Ser
    850                 855                 860
Lys Asn Leu Asp Cys Trp Val Asp Asn Glu Glu Asp Ile Asp Val Ile
865                 870                 875                 880
Leu Lys Lys Ser Thr Ile Leu Asn Leu Asp Ile Asn Asn Asp Ile Ile
                885                 890                 895
Ser Asp Ile Ser Gly Phe Asn Ser Ser Val Ile Thr Tyr Pro Asp Ala
            900                 905                 910
Gln Leu Val Pro Gly Ile Asn Gly Lys Ala Ile His Leu Val Asn Asn
            915                 920                 925
Glu Ser Ser Glu Val Ile Val His Lys Ala Met Asp Ile Glu Tyr Asn
    930                 935                 940
Asp Met Phe Asn Asn Phe Thr Val Ser Phe Trp Leu Arg Val Pro Lys
945                 950                 955                 960
Val Ser Ala Ser His Leu Glu Gln Tyr Gly Thr Asn Glu Tyr Ser Ile
                965                 970                 975
Ile Ser Ser Met Lys Lys His Ser Leu Ser Ile Gly Ser Gly Trp Ser
                980                 985                 990
Val Ser Leu Lys Gly Asn Asn Leu Ile Trp Thr Leu Lys Asp Ser Ala
            995                 1000                1005
Gly Glu Val Arg Gln Ile Thr Phe Arg Asp Leu Pro Asp Lys Phe
    1010                1015                1020
Asn Ala Tyr Leu Ala Asn Lys Trp Val Phe Ile Thr Ile Thr Asn
    1025                1030                1035
Asp Arg Leu Ser Ser Ala Asn Leu Tyr Ile Asn Gly Val Leu Met
    1040                1045                1050
Gly Ser Ala Glu Ile Thr Gly Leu Gly Ala Ile Arg Glu Asp Asn
    1055                1060                1065
Asn Ile Thr Leu Lys Leu Asp Arg Cys Asn Asn Asn Asn Gln Tyr
    1070                1075                1080
Val Ser Ile Asp Lys Phe Arg Ile Phe Cys Lys Ala Leu Asn Pro
    1085                1090                1095
Lys Glu Ile Glu Lys Leu Tyr Thr Ser Tyr Leu Ser Ile Thr Phe
```

```
                      1100                1105                 1110
Leu Arg Asp Phe Trp Gly Asn Pro Leu Arg Tyr Asp Thr Glu Tyr
    1115                1120                1125

Tyr Leu Ile Pro Val Ala Ser Ser Ser Lys Asp Val Gln Leu Lys
    1130                1135                1140

Asn Ile Thr Asp Tyr Met Tyr Leu Thr Asn Ala Pro Ser Tyr Thr
    1145                1150                1155

Asn Gly Lys Leu Asn Ile Tyr Tyr Arg Arg Leu Tyr Asn Gly Leu
    1160                1165                1170

Lys Phe Ile Ile Lys Arg Tyr Thr Pro Asn Asn Glu Ile Asp Ser
    1175                1180                1185

Phe Val Lys Ser Gly Asp Phe Ile Lys Leu Tyr Val Ser Tyr Asn
    1190                1195                1200

Asn Asn Glu His Ile Val Gly Tyr Pro Lys Asp Gly Asn Ala Phe
    1205                1210                1215

Asn Asn Leu Asp Arg Ile Leu Arg Val Gly Tyr Asn Ala Pro Gly
    1220                1225                1230

Ile Pro Leu Tyr Lys Lys Met Glu Ala Val Lys Leu Arg Asp Leu
    1235                1240                1245

Lys Thr Tyr Ser Val Gln Leu Lys Leu Tyr Asp Asp Lys Asn Ala
    1250                1255                1260

Ser Leu Gly Leu Val Gly Thr His Asn Gly Gln Ile Gly Asn Asp
    1265                1270                1275

Pro Asn Arg Asp Ile Leu Ile Ala Ser Asn Trp Tyr Phe Asn His
    1280                1285                1290

Leu Lys Asp Lys Ile Leu Gly Cys Asp Trp Tyr Phe Val Pro Thr
    1295                1300                1305

Asp Glu Gly Trp Thr Asn Asp
    1310                1315

<210> SEQ ID NO 9
<211> LENGTH: 293
<212> TYPE: PRT
<213> ORGANISM: C. botulinum

<400> SEQUENCE: 9

Met Glu His Tyr Ser Val Ile Gln Asn Ser Leu Asn Asp Lys Ile Val
1               5                   10                  15

Thr Ile Ser Cys Lys Ala Asp Thr Asn Leu Phe Phe Tyr Gln Val Ala
                20                  25                  30

Gly Asn Val Ser Leu Phe Gln Gln Thr Arg Asn Tyr Leu Glu Arg Trp
            35                  40                  45

Arg Leu Ile Tyr Asp Ser Asn Lys Ala Ala Tyr Lys Ile Lys Ser Met
        50                  55                  60

Asp Ile His Asn Thr Asn Leu Val Leu Thr Trp Asn Ala Pro Thr His
65                  70                  75                  80

Asn Ile Ser Thr Gln Gln Asp Ser Asn Ala Asp Asn Gln Tyr Trp Leu
                85                  90                  95

Leu Leu Lys Asp Ile Gly Asn Asn Ser Phe Ile Ile Ala Ser Tyr Lys
            100                 105                 110

Asn Pro Asn Leu Val Leu Tyr Ala Asp Thr Val Ala Arg Asn Leu Lys
        115                 120                 125

Leu Ser Thr Leu Asn Asn Ser Asn Tyr Ile Lys Phe Ile Ile Glu Asp
    130                 135                 140
```

```
Tyr Ile Ile Ser Asp Leu Asn Asn Phe Thr Cys Lys Ile Ser Pro Ile
145                 150                 155                 160

Leu Asp Leu Asn Lys Val Val Gln Gln Val Asp Val Thr Asn Leu Asn
                165                 170                 175

Val Asn Leu Tyr Thr Trp Asp Tyr Gly Arg Asn Gln Lys Trp Thr Ile
            180                 185                 190

Arg Tyr Asn Glu Glu Lys Ala Ala Tyr Gln Phe Phe Asn Thr Ile Leu
        195                 200                 205

Ser Asn Gly Val Leu Thr Trp Ile Phe Ser Asn Gly Asn Thr Val Arg
    210                 215                 220

Val Ser Ser Ser Asn Asp Gln Asn Asn Asp Ala Gln Tyr Trp Leu Ile
225                 230                 235                 240

Asn Pro Val Ser Asp Thr Asp Glu Thr Tyr Thr Ile Thr Asn Leu Arg
                245                 250                 255

Asp Thr Thr Lys Ala Leu Asp Leu Tyr Gly Gly Gln Thr Ala Asn Gly
            260                 265                 270

Thr Ala Ile Gln Val Phe Asn Tyr His Gly Asp Asp Asn Gln Lys Trp
        275                 280                 285

Asn Ile Arg Asn Pro
    290

<210> SEQ ID NO 10
<211> LENGTH: 293
<212> TYPE: PRT
<213> ORGANISM: C. botulinum

<400> SEQUENCE: 10

Met Glu His Tyr Ser Val Ile Gln Asn Ser Leu Asn Asp Lys Ile Val
1               5                   10                  15

Thr Ile Ser Cys Lys Ala Asp Thr Asn Leu Phe Phe Tyr Gln Val Ala
            20                  25                  30

Gly Asn Val Ser Leu Phe Gln Gln Thr Arg Asn Tyr Leu Glu Arg Trp
        35                  40                  45

Arg Leu Ile Tyr Asp Ser Asn Lys Ala Ala Tyr Lys Ile Lys Ser Met
    50                  55                  60

Asp Ile His Asn Thr Asn Leu Val Leu Thr Trp Asn Ala Pro Thr His
65                  70                  75                  80

Asn Ile Ser Thr Gln Gln Asp Ser Asn Ala Asp Asn Gln Tyr Trp Leu
                85                  90                  95

Leu Leu Lys Asp Ile Gly Asn Asn Ser Phe Ile Ile Ala Ser Tyr Lys
            100                 105                 110

Asn Pro Asn Leu Val Leu Tyr Ala Asp Thr Val Ala Arg Asn Leu Lys
        115                 120                 125

Leu Ser Thr Leu Asn Asn Ser Asn Tyr Ile Lys Phe Ile Ile Glu Asp
    130                 135                 140

Tyr Ile Ile Ser Asp Leu Asn Asn Phe Thr Cys Lys Ile Ser Pro Ile
145                 150                 155                 160

Leu Asp Arg Asn Lys Val Val Gln Gln Val Asp Met Thr Asn Leu Asn
                165                 170                 175

Val Asn Leu Tyr Thr Trp Asp Tyr Gly Arg Asn Gln Lys Trp Thr Ile
            180                 185                 190

Arg Tyr Asn Glu Glu Lys Ala Ala Tyr Gln Phe Phe Asn Thr Ile Leu
        195                 200                 205

Ser Asn Gly Val Leu Thr Trp Ile Phe Ser Asn Gly Asn Thr Val Arg
    210                 215                 220
```

```
Val Ser Ser Ser Asn Asp Gln Asn Asn Asp Ala Gln Tyr Trp Leu Ile
225                 230                 235                 240

Asn Pro Val Ser Asp Thr Asp Glu Thr Tyr Thr Ile Thr Asn Leu Arg
            245                 250                 255

Asp Thr Thr Lys Ala Leu Asp Leu Tyr Asn Ser Gln Thr Ala Asn Gly
            260                 265                 270

Thr Ala Ile Gln Val Phe Asn Tyr His Gly Asp Asp Asn Gln Lys Trp
            275                 280                 285

Asn Ile Arg Asn Pro
            290

<210> SEQ ID NO 11
<211> LENGTH: 293
<212> TYPE: PRT
<213> ORGANISM: C. botulinum

<400> SEQUENCE: 11

Met Glu His Tyr Ser Val Ile Gln Asn Ser Leu Asn Asp Lys Ile Val
1               5                   10                  15

Thr Ile Ser Cys Arg Ala Asp Thr Asn Leu Phe Phe Tyr Gln Val Ala
            20                  25                  30

Gly Asn Val Ser Leu Phe Gln Gln Thr Arg Asn Tyr Leu Glu Arg Trp
            35                  40                  45

Arg Ile Ile Tyr Asp Ser Asn Lys Ala Ala Tyr Lys Ile Lys Ser Met
50                  55                  60

Asp Ile His Asn Thr Asn Leu Val Leu Thr Trp Asn Ala Pro Thr His
65                  70                  75                  80

Asn Ile Ser Thr Gln Gln Asp Ser Asn Ala Asp Asn Gln Tyr Trp Leu
            85                  90                  95

Leu Leu Lys Asp Ile Gly Asn Asn Ser Phe Ile Ile Ala Ser Tyr Lys
            100                 105                 110

Asn Pro Asn Leu Val Leu Tyr Ala Asp Thr Val Ala Arg Asn Leu Lys
            115                 120                 125

Leu Ser Thr Leu Asn Asn Ser Asn Tyr Ile Lys Phe Ile Ile Glu Asp
            130                 135                 140

Tyr Ile Ile Ser Asp Phe Asn Asn Phe Thr Cys Lys Ile Ser Pro Ile
145                 150                 155                 160

Leu Asp Arg Asn Lys Val Val Gln Gln Val Ala Thr Thr Asn Leu Asn
            165                 170                 175

Val Asn Leu Tyr Thr Trp Asp Tyr Gly Arg Asn Gln Lys Trp Thr Ile
            180                 185                 190

Arg Tyr Asn Glu Glu Lys Ala Ala Tyr Gln Phe Phe Asn Thr Ile Leu
            195                 200                 205

Ser Asn Gly Val Leu Thr Trp Ile Phe Ser Asn Gly Asn Thr Val Arg
            210                 215                 220

Val Ser Ser Ser Asn Asp Gln Asn Asn Asp Ala Gln Tyr Trp Leu Ile
225                 230                 235                 240

Asn Pro Val Ser Asp Thr Asp Glu Thr Tyr Thr Ile Thr Asn Leu Arg
            245                 250                 255

Asp Thr Thr Lys Ala Leu Asp Leu Tyr Asn Ser Gln Thr Ala Asn Gly
            260                 265                 270

Thr Ala Ile Gln Val Phe Asn Ser Asn Gly Gly Asp Asn Gln Lys Trp
            275                 280                 285

Asn Ile Arg Asn Pro
```

-continued

```
                290

<210> SEQ ID NO 12
<211> LENGTH: 294
<212> TYPE: PRT
<213> ORGANISM: C. botulinum

<400> SEQUENCE: 12

Met Glu His Tyr Ser Thr Ile Gln Asn Ser Leu Asn Asp Lys Ile Val
1               5                   10                  15

Thr Ile Ser Cys Lys Ala Asn Thr Asp Leu Phe Phe Tyr Gln Val Pro
            20                  25                  30

Gly Asn Gly Asn Val Ser Leu Phe Gln Gln Thr Arg Asn Tyr Leu Glu
        35                  40                  45

Arg Trp Arg Ile Ile Tyr Asp Ser Asn Lys Ala Ala Tyr Lys Ile Lys
    50                  55                  60

Ser Met Asn Ile Tyr Asn Thr Asn Leu Val Leu Thr Trp Asn Ala Pro
65                  70                  75                  80

Thr His Asn Ile Ser Ala Gln Gln Asp Ser Asn Ala Asp Asn Gln Tyr
                85                  90                  95

Trp Leu Leu Leu Lys Asp Ile Gly Asn Asn Ser Phe Ile Ile Ala Ser
            100                 105                 110

Tyr Lys Asn Pro Asn Leu Val Leu Tyr Ala Asp Thr Val Ala Arg Asn
        115                 120                 125

Leu Lys Leu Ser Thr Leu Asn Asn Ser Ser Tyr Ile Lys Phe Ile Ile
    130                 135                 140

Glu Asp Tyr Val Ile Ser Asp Phe Lys Asn Phe Thr Cys Arg Ile Ser
145                 150                 155                 160

Pro Ile Leu Ala Gly Gly Lys Val Val Gln Gln Val Ser Met Thr Asn
                165                 170                 175

Leu Ala Val Asn Leu Tyr Ile Trp Asn Asn Asp Leu Asn Gln Lys Trp
            180                 185                 190

Thr Ile Ile Tyr Asn Glu Glu Lys Ala Ala Tyr Gln Phe Phe Asn Lys
        195                 200                 205

Ile Leu Ser Asn Gly Val Leu Thr Trp Ile Phe Ser Asp Gly Asn Thr
    210                 215                 220

Val Arg Val Ser Ser Ala Gln Asn Asn Asp Ala Gln Tyr Trp Leu
225                 230                 235                 240

Ile Asn Pro Val Ser Asp Asn Tyr Asp Arg Tyr Thr Ile Thr Asn Leu
                245                 250                 255

Arg Asp Lys Thr Lys Val Leu Asp Leu Tyr Gly Gly Gln Thr Ala Asp
            260                 265                 270

Gly Thr Thr Ile Gln Val Phe Asn Ser Asn Gly Gly Asp Asn Gln Ile
        275                 280                 285

Trp Thr Met Ser Asn Pro
    290

<210> SEQ ID NO 13
<211> LENGTH: 279
<212> TYPE: PRT
<213> ORGANISM: C. botulinum

<400> SEQUENCE: 13

Met Glu His Tyr Ser Val Ile Gln Asn Ser Leu Asn Asp Lys Ile Val
1               5                   10                  15

Thr Ile Ser Cys Lys Ala Asp Thr Asn Leu Phe Phe Tyr Gln Val Ala
```

```
                    20                  25                  30
Gly Asn Val Ser Leu Phe Gln Gln Thr Arg Asn Tyr Leu Glu Arg Trp
            35                  40                  45

Arg Leu Ile Tyr Asp Ser Asn Lys Ala Ala Tyr Lys Ile Lys Ser Met
        50                  55                  60

Asp Ile His Asn Thr Asn Leu Val Leu Thr Trp Asn Ala Pro Thr His
65                  70                  75                  80

Asn Ile Ser Thr Gln Gln Asp Ser Asn Ala Asp Asn Gln Tyr Trp Leu
                85                  90                  95

Leu Leu Lys Asp Ile Gly Asn Asn Ser Phe Ile Ile Ala Ser Tyr Lys
            100                 105                 110

Asn Pro Asn Leu Val Leu Tyr Ala Asp Thr Val Ala Arg Asn Leu Lys
        115                 120                 125

Leu Ser Thr Leu Asn Asn Ser Asn Tyr Ile Lys Phe Ile Glu Asp
    130                 135                 140

Tyr Ile Ile Ser Asp Leu Asn Asn Phe Thr Cys Lys Ile Ser Pro Ile
145                 150                 155                 160

Leu Asp Arg Asn Lys Val Val Gln Gln Val Asp Met Thr Asn Leu Asn
                165                 170                 175

Val Asn Leu Tyr Thr Trp Asp Tyr Gly Arg Asn Gln Lys Trp Thr Ile
            180                 185                 190

Arg Tyr Asn Glu Glu Lys Ala Ala Tyr Gln Phe Phe Asn Thr Ile Leu
        195                 200                 205

Ser Asn Gly Val Leu Thr Trp Ile Phe Ser Asn Gly Asn Thr Val Arg
    210                 215                 220

Val Ser Ser Asn Asp Gln Asn Asn Asp Ala Gln Tyr Trp Leu Ile
225                 230                 235                 240

Asn Pro Val Ser Asp Thr Asp Glu Thr Tyr Thr Ile Thr Asn Leu Arg
                245                 250                 255

Asp Thr Thr Lys Ala Leu Asp Leu Tyr Asn Ser Gln Thr Ala Asn Gly
            260                 265                 270

Thr Ala Ile Gln Val Phe Asn
        275

<210> SEQ ID NO 14
<211> LENGTH: 292
<212> TYPE: PRT
<213> ORGANISM: C. botulinum

<400> SEQUENCE: 14

Met Glu His Tyr Ser Val Ile Gln Asn Ser Leu Asn Asp Glu Ile Val
1               5                   10                  15

Thr Ile Ser Cys Lys Ala Asp Thr Asn Leu Phe Phe Tyr Gln Thr Val
            20                  25                  30

Gly Asn Val Ser Leu Phe Gln Gln Thr Arg Asn Tyr Leu Glu Arg Trp
        35                  40                  45

Arg Leu Ile Tyr Asp Ala Asn Lys Ala Ala Tyr Lys Ile Lys Ser Met
    50                  55                  60

Asp Ser His Asn Thr Asn Leu Val Leu Thr Trp Asn Ala Pro Thr His
65                  70                  75                  80

Asn Ile Ser Ala Gln Gln Asp Ser Asn Ala Asp Asn Gln Tyr Trp Leu
                85                  90                  95

Leu Leu Lys Asp Ile Gly Ser Asn Ser Phe Ile Ile Ala Ser Tyr Lys
            100                 105                 110
```

```
Asn Pro Asn Leu Val Leu Tyr Ala Asp Thr Val Ala Arg Asn Leu Lys
        115                 120                 125

Leu Ser Thr Leu Asn Asn Ser Ser Tyr Ile Lys Phe Ile Ile Glu Asp
130                 135                 140

Tyr Met Ile Ser Asp Phe Asn Asn Phe Thr Cys Lys Ile Ser Pro Ile
145                 150                 155                 160

Leu Asp Ser Ser Lys Val Val Gln Gln Val Ala Met Thr Asp Leu Ser
                165                 170                 175

Val Asn Leu Tyr Thr Trp Asp Tyr Gly Arg Asn Gln Lys Trp Thr Ile
            180                 185                 190

Lys Tyr Asn Lys Glu Lys Ser Ala Tyr Gln Phe Phe Asn Thr Ile Leu
        195                 200                 205

Ser Asn Gly Val Leu Thr Trp Ile Ser Ser Asn Gly Asn Thr Val Arg
    210                 215                 220

Val Ser Ser Ile Ala Gln Asn Asn Asp Ala Gln Tyr Trp Leu Ile Asn
225                 230                 235                 240

Pro Val Ser Asn Ala Tyr Glu Thr Tyr Thr Ile Thr Asn Leu His Asp
                245                 250                 255

Thr Thr Lys Ala Leu Asp Leu Tyr Asn Ser Gln Thr Ala Asn Gly Thr
            260                 265                 270

Thr Ile Gln Val Phe Asn Tyr His Gly Asp Asp Asn Gln Lys Trp Phe
        275                 280                 285

Ile Arg Asn Pro
    290

<210> SEQ ID NO 15
<211> LENGTH: 291
<212> TYPE: PRT
<213> ORGANISM: C. botulinum

<400> SEQUENCE: 15

Met Glu His Tyr Ser Thr Ile Gln Asn Ser Leu Asn Asp Lys Ile Val
1               5                   10                  15

Thr Ile Ser Cys Lys Ala Asn Thr Asp Leu Phe Phe Tyr Gln Val Pro
            20                  25                  30

Gly Asn Gly Asn Val Ser Leu Phe Gln Gln Thr Arg Asn Tyr Leu Glu
        35                  40                  45

Arg Trp Arg Ile Ile Tyr Asp Ser Asn Lys Ala Ala Tyr Lys Ile Lys
    50                  55                  60

Ser Met Asn Ile Tyr Asn Thr Asn Leu Val Leu Thr Trp Asn Ala Pro
65                  70                  75                  80

Thr His Asn Ile Ser Ala Leu Gln Asp Ser Asn Ala Asp Asn Gln Tyr
                85                  90                  95

Trp Leu Leu Leu Lys Asp Ile Gly Asn Asn Ser Phe Ile Ile Ala Ser
            100                 105                 110

Tyr Lys Asn Pro Asn Leu Val Leu Tyr Ala Asp Thr Val Ala Arg Asn
        115                 120                 125

Leu Lys Leu Ser Thr Leu Asn Asn Ser Ser Tyr Ile Lys Phe Ile Ile
    130                 135                 140

Glu Asp Tyr Val Ile Ser Asp Phe Lys Asn Phe Thr Cys Arg Ile Ser
145                 150                 155                 160

Pro Ile Leu Ala Gly Gly Lys Val Val Gln Gln Val Ser Met Thr Asn
                165                 170                 175

Leu Ala Val Asn Leu Tyr Ile Trp Asn Asn Asp Leu Asn Gln Lys Trp
            180                 185                 190
```

-continued

Thr Ile Ile Tyr Asn Glu Glu Lys Ala Ala Tyr Gln Phe Phe Asn Lys
            195                 200                 205

Ile Leu Ser Asn Gly Val Leu Thr Trp Ile Phe Ser Asp Gly Asn Thr
        210                 215                 220

Val Arg Val Ser Ser Ser Ala Gln Asn Asp Ala Gln Tyr Trp Leu Ile
225                 230                 235                 240

Asn Pro Val Ser Asp Asn Tyr Asp Arg Tyr Thr Ile Thr Asn Leu Arg
                245                 250                 255

Tyr Lys Thr Lys Val Leu Asp Leu Tyr Gly Gly Gln Thr Ala Asp Gly
            260                 265                 270

Thr Thr Ile Gln Val Phe Asn Ser Asn Gly Gly Asp Asn Gln Ile Trp
        275                 280                 285

Tyr Gly Leu
        290

<210> SEQ ID NO 16
<211> LENGTH: 286
<212> TYPE: PRT
<213> ORGANISM: C. botulinum

<400> SEQUENCE: 16

Met Ser Gln Thr Asn Ala Asn Asp Leu Arg Asn Asn Glu Val Phe Phe
1               5                   10                  15

Ile Ser Pro Ser Asn Asn Thr Asn Lys Val Leu Asp Lys Ile Ser Gln
            20                  25                  30

Ser Glu Val Lys Leu Trp Asn Lys Leu Ser Gly Ala Asn Gln Lys Trp
        35                  40                  45

Arg Leu Ile Tyr Asp Thr Asn Lys Gln Ala Tyr Lys Ile Lys Val Met
    50                  55                  60

Asp Asn Thr Ser Leu Ile Leu Thr Trp Asn Ala Pro Leu Ser Ser Val
65                  70                  75                  80

Ser Val Lys Thr Asp Thr Asn Gly Asp Asn Gln Tyr Trp Tyr Leu Leu
                85                  90                  95

Gln Asn Tyr Ile Ser Arg Asn Val Ile Ile Arg Asn Tyr Met Asn Pro
            100                 105                 110

Asn Leu Val Leu Gln Tyr Asn Ile Asp Asp Thr Leu Met Val Ser Thr
        115                 120                 125

Gln Thr Ser Ser Ser Asn Gln Phe Phe Lys Phe Ser Asn Cys Ile Tyr
    130                 135                 140

Glu Ala Leu Asn Asn Arg Asn Cys Lys Leu Gln Thr Gln Leu Asn Ser
145                 150                 155                 160

Asp Arg Phe Leu Ser Lys Asn Leu Asn Ser Gln Ile Ile Val Leu Trp
                165                 170                 175

Gln Trp Phe Asp Ser Ser Arg Leu Lys Trp Ile Ile Glu Tyr Asn Glu
            180                 185                 190

Thr Lys Ser Ala Tyr Thr Leu Lys Cys Gln Glu Asn Asn Arg Tyr Leu
        195                 200                 205

Thr Trp Ile Gln Asn Ser Asn Asn Tyr Val Glu Thr Tyr Gln Ser Thr
    210                 215                 220

Asp Ser Leu Ile Gln Tyr Trp Asn Ile Asn Tyr Leu Asp Asn Asp Ala
225                 230                 235                 240

Ser Lys Tyr Ile Leu Tyr Asn Leu Gln Asp Thr Asn Arg Val Leu Asp
                245                 250                 255

Val Tyr Asn Ser Gln Ile Ala Asn Gly Thr His Val Ile Val Asp Ser

```
                260                 265                 270
Tyr His Gly Asn Thr Asn Gln Gln Trp Ile Ile Asn Leu Ile
            275                 280                 285

<210> SEQ ID NO 17
<211> LENGTH: 285
<212> TYPE: PRT
<213> ORGANISM: C. botulinum

<400> SEQUENCE: 17

Met Ser Gln Thr Asn Ala Asn Asp Leu Arg Asn Asn Glu Val Phe Phe
1               5                   10                  15

Ile Ser Pro Ser Asn Asn Thr Asn Lys Val Leu Asp Lys Ile Ser Gln
            20                  25                  30

Ser Glu Val Lys Leu Trp Asn Lys Leu Ser Gly Ala Asn Gln Lys Trp
        35                  40                  45

Arg Leu Ile Tyr Asp Thr Asn Lys Gln Ala Tyr Lys Ile Lys Val Met
    50                  55                  60

Asp Asn Thr Ser Leu Ile Leu Thr Trp Asn Ala Pro Leu Ser Ser Val
65                  70                  75                  80

Ser Val Lys Thr Asp Thr Asn Gly Asp Asn Gln Tyr Trp Tyr Leu Leu
                85                  90                  95

Gln Asn Tyr Ile Ser Arg Asn Val Ile Ile Arg Asn Tyr Met Asn Pro
            100                 105                 110

Asn Leu Val Leu Gln Tyr Asn Ile Asp Asp Thr Leu Met Val Ser Thr
        115                 120                 125

Gln Thr Ser Ser Ser Asn Gln Phe Phe Lys Phe Ser Asn Cys Ile Tyr
    130                 135                 140

Glu Ser Phe Asn Asn Ser Thr Cys Lys Ile Gln Thr Ser Leu Thr Ile
145                 150                 155                 160

Lys Phe Ile Asp Lys Asn Gln Asn Ser Asn Asn Val Thr Ile Trp Ser
                165                 170                 175

Trp Asn Asn Gly Asp Asn Gln Lys Trp Lys Ile Leu Tyr Asn Glu Ser
            180                 185                 190

Lys Met Ala Tyr Thr Leu Thr Cys Ile Lys Asn Asn Glu Tyr Leu Thr
        195                 200                 205

Trp Phe Ser Ser Ile Gly Asn Asn Val Gly Thr Tyr Arg Thr Glu Gly
    210                 215                 220

Asn Asn Asp Gln Tyr Trp Phe Ile Asn Tyr Leu Asn Asn Asp Ala Ser
225                 230                 235                 240

Met Tyr Thr Ile Ser Asn Phe Ser Asn Gln Ser Lys Phe Leu Asp Val
                245                 250                 255

Val Asn Ser Gly Leu Ala Asp Gly Thr Asn Val Gln Val Trp Asp Ser
            260                 265                 270

Asn Gly Thr Ser Ala Gln Lys Trp Ile Ile Thr Arg Leu
        275                 280                 285

<210> SEQ ID NO 18
<211> LENGTH: 286
<212> TYPE: PRT
<213> ORGANISM: C. botulinum

<400> SEQUENCE: 18

Met Ser Gln Thr Asn Ala Asn Asp Leu Arg Asn Asn Glu Val Phe Phe
1               5                   10                  15

Ile Ser Pro Ser Asn Asn Thr Asn Lys Val Leu Asp Lys Ile Ser Gln
```

```
                    20                  25                  30
Ser Glu Val Lys Leu Trp Asn Lys Leu Ser Gly Ala Asn Gln Lys Trp
                35                  40                  45

Arg Leu Ile Tyr Asp Thr Asn Lys Gln Ala Tyr Thr Ile Lys Val Met
            50                  55                  60

Asp Asn Thr Ser Leu Ile Leu Thr Trp Asp Ala Pro Leu Ser Ser Val
65                  70                  75                  80

Ser Val Lys Thr Asp Thr Asn Thr Asn Asn Gln Tyr Trp Tyr Leu Leu
                85                  90                  95

Gln Asp Tyr Ile Ser Arg Asn Val Ile Leu Arg Asn Tyr Met Asn Pro
            100                 105                 110

Asn Leu Val Leu Gln Tyr Asn Thr Asp Thr Leu Ile Val Ser Thr
            115                 120                 125

Gln Thr Asn Ser Asn Asn Gln Phe Phe Lys Phe Ser Asn Cys Ile Tyr
        130                 135                 140

Glu Ala Leu Asn Asn Arg Asn Cys Lys Leu Gln Thr Gln Leu Asn Ser
145                 150                 155                 160

Asp Arg Phe Leu Ser Lys Asn Leu Asn Ser Gln Ile Ile Val Leu Trp
                165                 170                 175

Gln Trp Phe Asp Ser Ser Arg Gln Lys Trp Thr Ile Glu Tyr Asn Glu
            180                 185                 190

Thr Lys Ser Ala Tyr Thr Leu Lys Cys Gln Glu Asn Asn Arg Tyr Leu
        195                 200                 205

Thr Trp Ile Gln Asn Ser Asn Asn Tyr Val Glu Thr Tyr Gln Ser Thr
    210                 215                 220

Asp Ser Leu Ile Gln Tyr Trp Asn Ile Asn Tyr Leu Asp Asn Asp Ala
225                 230                 235                 240

Ser Lys Tyr Ile Leu Tyr Asn Leu Gln Asp Thr Asn Arg Val Leu Asp
                245                 250                 255

Val Tyr Asn Ser Gln Thr Ala Asn Gly Thr His Val Ile Val Asp Ser
            260                 265                 270

Tyr His Gly Asn Thr Asn Gln Gln Trp Ile Ile Asn Leu Ile
        275                 280                 285

<210> SEQ ID NO 19
<211> LENGTH: 146
<212> TYPE: PRT
<213> ORGANISM: C. botulinum

<400> SEQUENCE: 19

Met Ser Val Glu Arg Thr Phe Leu Pro Asn Gly Asn Tyr Asn Ile Lys
1               5                   10                  15

Ser Ile Phe Ser Gly Ser Leu Tyr Leu Asn Pro Val Ser Lys Ser Leu
            20                  25                  30

Thr Phe Ser Asn Glu Ser Ser Ala Asn Asn Gln Lys Trp Asn Val Glu
        35                  40                  45

Tyr Met Ala Glu Asn Arg Cys Phe Lys Ile Ser Asn Val Ala Glu Pro
    50                  55                  60

Asn Lys Tyr Leu Ser Tyr Asp Asn Phe Gly Phe Ile Ser Leu Asp Ser
65                  70                  75                  80

Leu Ser Asn Arg Cys Tyr Trp Phe Pro Ile Lys Ile Ala Val Asn Thr
                85                  90                  95

Tyr Ile Met Leu Ser Leu Asn Lys Val Asn Glu Leu Asp Tyr Ala Trp
            100                 105                 110
```

```
Asp Ile Tyr Asp Thr Asn Glu Asn Ile Leu Ser Gln Pro Leu Leu Leu
            115                 120                 125

Leu Pro Asn Phe Asp Ile Tyr Asn Ser Asn Gln Met Phe Lys Leu Glu
        130                 135                 140

Lys Ile
145

<210> SEQ ID NO 20
<211> LENGTH: 146
<212> TYPE: PRT
<213> ORGANISM: C. botulinum

<400> SEQUENCE: 20

Met Ser Ala Glu Arg Thr Phe Leu Pro Asn Gly Asn Tyr Asn Ile Lys
1               5                   10                  15

Ser Ile Phe Ser Gly Ser Leu Tyr Leu Ser Pro Val Ser Gly Ser Leu
            20                  25                  30

Thr Phe Ser Asn Glu Ser Ser Ala Asn Asn Gln Lys Trp Asn Val Glu
        35                  40                  45

Tyr Met Ala Glu Asn Arg Cys Phe Lys Ile Ser Asn Val Ala Glu Pro
    50                  55                  60

Asn Lys Tyr Leu Ser Tyr Asp Asn Phe Gly Phe Ile Ser Leu Asp Ser
65                  70                  75                  80

Leu Ser Asn Arg Cys Tyr Trp Phe Pro Ile Lys Ile Ala Val Asn Thr
                85                  90                  95

Tyr Ile Met Leu Ser Leu Asn Lys Val Asn Glu Leu Asp Tyr Ala Trp
            100                 105                 110

Asp Ile Tyr Asp Thr Asn Glu Asn Ile Leu Ser Gln Pro Leu Leu Leu
            115                 120                 125

Leu Pro Asn Phe Asp Ile Tyr Asn Ser Asn Gln Met Phe Lys Leu Glu
        130                 135                 140

Lys Ile
145

<210> SEQ ID NO 21
<211> LENGTH: 146
<212> TYPE: PRT
<213> ORGANISM: C. botulinum

<400> SEQUENCE: 21

Met Ser Ser Glu Arg Thr Phe Leu Pro Asn Gly Asn Tyr Lys Ile Lys
1               5                   10                  15

Ser Leu Phe Ser Asn Ser Leu Tyr Leu Thr Tyr Ser Ser Gly Ala Leu
            20                  25                  30

Ser Phe Ser Asn Thr Ser Ser Leu Asp Asn Gln Lys Trp Lys Leu Glu
        35                  40                  45

Tyr Ile Ser Ser Ser Asn Gly Phe Arg Phe Ser Asn Val Ala Glu Pro
    50                  55                  60

Asn Lys Tyr Leu Ala Tyr Asn Asp Tyr Gly Phe Ile Tyr Leu Ser Ser
65                  70                  75                  80

Ser Ser Asn Asn Ser Leu Trp Asn Pro Ile Lys Ile Ala Ile Asn Ser
                85                  90                  95

Tyr Ile Ile Cys Thr Leu Ser Ile Val Asn Val Thr Asp Tyr Ala Trp
            100                 105                 110

Thr Ile Tyr Asp Asn Asn Asn Asn Ile Thr Asp Gln Pro Ile Leu Asn
            115                 120                 125
```

```
Leu Pro Asn Phe Asp Ile Asn Asn Ser Asn Gln Ile Leu Lys Leu Glu
        130                 135                 140

Lys Leu
145
```

<210> SEQ ID NO 22
<211> LENGTH: 146
<212> TYPE: PRT
<213> ORGANISM: C. botulinum

<400> SEQUENCE: 22

```
Met Ser Ser Glu Arg Thr Phe Leu Pro Asn Gly Asn Tyr Lys Ile Lys
1               5                   10                  15

Ser Leu Phe Ser Asp Ser Leu Tyr Leu Thr Tyr Ser Ser Gly Ser Leu
            20                  25                  30

Ser Phe Leu Asn Thr Ser Ser Leu Asp Asn Gln Lys Trp Lys Leu Glu
        35                  40                  45

Tyr Ile Ser Ser Ser Asn Gly Phe Arg Phe Ser Asn Val Ala Glu Pro
    50                  55                  60

Asn Lys Tyr Leu Ala Tyr Asn Asp Tyr Gly Phe Ile Tyr Leu Ser Ser
65                  70                  75                  80

Ser Ser Asn Asn Ser Leu Trp Asn Pro Ile Lys Ile Ala Ile Asn Ser
                85                  90                  95

Tyr Ile Ile Cys Thr Leu Ser Ile Val Asn Val Thr Asp Tyr Ala Trp
            100                 105                 110

Thr Ile Tyr Asp Asn Asn Asn Ile Thr Asp Gln Pro Ile Leu Asn
        115                 120                 125

Leu Pro Asn Phe Asp Ile Asn Asn Ser Asn Gln Ile Leu Lys Leu Glu
    130                 135                 140

Lys Leu
145
```

<210> SEQ ID NO 23
<211> LENGTH: 1193
<212> TYPE: PRT
<213> ORGANISM: C. botulinum

<400> SEQUENCE: 23

```
Met Asn Ile Asn Asp Asn Leu Ser Ile Asn Ser Pro Val Asp Asn Lys
1               5                   10                  15

Asn Val Val Val Val Arg Ala Arg Lys Thr Asp Thr Val Phe Lys Ala
            20                  25                  30

Phe Lys Val Ala Pro Asn Ile Trp Val Ala Pro Glu Arg Tyr Tyr Gly
        35                  40                  45

Glu Ser Leu Ser Ile Asp Glu Glu Tyr Lys Val Asp Gly Gly Ile Tyr
    50                  55                  60

Asp Ser Asn Phe Leu Ser Gln Asp Ser Glu Lys Asp Lys Phe Leu Gln
65                  70                  75                  80

Ala Ile Ile Thr Leu Leu Lys Arg Ile Asn Ser Thr Asn Ala Gly Glu
                85                  90                  95

Lys Leu Leu Ser Leu Ile Ser Thr Ala Ile Pro Phe Pro Tyr Gly Tyr
            100                 105                 110

Ile Gly Gly Gly Tyr Tyr Ala Pro Asn Met Ile Thr Phe Gly Ser Ala
        115                 120                 125

Pro Lys Ser Asn Lys Lys Leu Asn Ser Leu Ile Ser Ser Thr Ile Pro
    130                 135                 140
```

```
Phe Pro Tyr Ala Gly Tyr Arg Glu Thr Asn Tyr Leu Ser Ser Glu Asp
145                 150                 155                 160

Asn Lys Ser Phe Tyr Ala Ser Asn Ile Val Ile Phe Gly Pro Gly Ala
                165                 170                 175

Asn Ile Val Glu Asn Asn Thr Val Phe Tyr Lys Lys Glu Asp Ala Glu
            180                 185                 190

Asn Gly Met Gly Thr Met Thr Glu Ile Trp Phe Gln Pro Phe Leu Thr
        195                 200                 205

Tyr Lys Tyr Asp Glu Phe Tyr Ile Asp Pro Ala Ile Glu Leu Ile Lys
    210                 215                 220

Cys Leu Ile Lys Ser Leu Tyr Phe Leu Tyr Gly Ile Lys Pro Ser Asp
225                 230                 235                 240

Asp Leu Val Ile Pro Tyr Arg Leu Arg Ser Glu Leu Glu Asn Ile Glu
                245                 250                 255

Tyr Ser Gln Leu Asn Ile Val Asp Leu Leu Val Ser Gly Gly Ile Asp
            260                 265                 270

Pro Lys Phe Ile Asn Thr Asp Pro Tyr Trp Phe Thr Asp Asn Tyr Phe
        275                 280                 285

Ser Asn Ala Lys Lys Val Phe Glu Asp His Arg Asn Ile Tyr Glu Thr
    290                 295                 300

Glu Ile Glu Gly Asn Asn Ala Ile Gly Asn Asp Ile Lys Leu Arg Leu
305                 310                 315                 320

Lys Gln Lys Phe Arg Ile Asn Ile Asn Asp Ile Trp Glu Leu Asn Leu
                325                 330                 335

Asn Tyr Phe Ser Lys Glu Phe Ser Ile Met Met Pro Asp Arg Phe Asn
            340                 345                 350

Asn Ala Leu Lys His Phe Tyr Arg Lys Gln Tyr Tyr Lys Ile Asp Tyr
        355                 360                 365

Pro Glu Asn Tyr Ser Ile Asn Gly Phe Val Asn Gly Gln Ile Asn Ala
    370                 375                 380

Gln Leu Ser Leu Ser Asp Arg Asn Gln Asp Ile Ile Asn Lys Pro Glu
385                 390                 395                 400

Glu Ile Ile Asn Leu Leu Asn Gly Asn Asn Val Ser Leu Met Arg Ser
                405                 410                 415

Asn Ile Tyr Gly Asp Gly Leu Lys Ser Thr Val Asp Asp Phe Tyr Ser
            420                 425                 430

Asn Tyr Lys Ile Pro Tyr Asn Arg Ala Tyr Glu Tyr His Phe Asn Asn
        435                 440                 445

Ser Asn Asp Ser Ser Leu Asp Asn Val Asn Ile Gly Val Ile Asp Asn
    450                 455                 460

Ile Pro Glu Ile Ile Asp Val Asn Pro Tyr Lys Glu Asn Cys Asp Lys
465                 470                 475                 480

Phe Ser Pro Val Gln Lys Ile Thr Ser Thr Arg Glu Ile Asn Thr Asn
                485                 490                 495

Ile Pro Trp Pro Ile Asn Tyr Leu Gln Ala Gln Asn Thr Asn Asn Glu
            500                 505                 510

Lys Phe Ser Leu Ser Ser Asp Phe Val Glu Val Ser Ser Lys Asp
        515                 520                 525

Lys Ser Leu Val Tyr Ser Phe Leu Ser Asn Val Met Phe Tyr Leu Asp
    530                 535                 540

Ser Ile Lys Asp Asn Ser Pro Ile Asp Thr Asp Lys Lys Tyr Tyr Leu
545                 550                 555                 560

Trp Leu Arg Glu Ile Phe Arg Asn Tyr Ser Phe Asp Ile Thr Ala Thr
```

-continued

```
            565                 570                 575
Gln Glu Ile Asn Thr Asn Cys Gly Ile Asn Lys Val Val Thr Trp Phe
            580                 585                 590
Gly Lys Ala Leu Asn Ile Leu Asn Thr Ser Asp Ser Phe Val Glu Glu
            595                 600                 605
Phe Gln Asn Leu Gly Ala Ile Ser Leu Ile Asn Lys Lys Glu Asn Leu
            610                 615                 620
Ser Met Pro Ile Ile Glu Ser Tyr Glu Ile Pro Asn Asp Met Leu Gly
625                 630                 635                 640
Leu Pro Leu Asn Asp Leu Asn Glu Lys Leu Phe Asn Ile Tyr Ser Lys
            645                 650                 655
Asn Thr Ala Tyr Phe Lys Lys Ile Tyr Tyr Asn Phe Leu Asp Gln Trp
            660                 665                 670
Trp Thr Gln Tyr Tyr Ser Gln Tyr Phe Asp Leu Ile Cys Met Ala Lys
            675                 680                 685
Arg Ser Val Leu Ala Gln Glu Thr Leu Ile Lys Arg Ile Ile Gln Lys
            690                 695                 700
Lys Leu Ser Tyr Leu Ile Gly Asn Ser Asn Ile Ser Ser Asp Asn Leu
705                 710                 715                 720
Ala Leu Met Asn Leu Thr Thr Thr Asn Thr Leu Arg Asp Ile Ser Asn
            725                 730                 735
Glu Ser Gln Ile Ala Met Asn Asn Val Asp Ser Phe Leu Asn Asn Ala
            740                 745                 750
Ala Ile Cys Val Phe Glu Ser Asn Ile Tyr Pro Lys Phe Ile Ser Phe
            755                 760                 765
Met Glu Gln Cys Ile Asn Asn Ile Asn Ile Lys Thr Lys Glu Phe Ile
            770                 775                 780
Gln Lys Cys Thr Asn Ile Asn Glu Asp Glu Lys Leu Gln Leu Ile Asn
785                 790                 795                 800
Gln Asn Val Phe Asn Ser Leu Asp Phe Glu Phe Leu Asn Ile Gln Asn
            805                 810                 815
Met Lys Ser Leu Phe Ser Ser Glu Thr Ala Leu Leu Ile Lys Glu Glu
            820                 825                 830
Thr Trp Pro Tyr Glu Leu Val Leu Tyr Ala Phe Lys Glu Pro Gly Asn
            835                 840                 845
Asn Val Ile Gly Asp Ala Ser Gly Lys Asn Thr Ser Ile Glu Tyr Ser
850                 855                 860
Lys Asp Ile Gly Leu Val Tyr Gly Ile Asn Ser Asp Ala Leu Tyr Leu
865                 870                 875                 880
Asn Gly Ser Asn Gln Ser Ile Ser Phe Ser Asn Asp Phe Phe Glu Asn
            885                 890                 895
Gly Leu Thr Asn Ser Phe Ser Ile Tyr Phe Trp Leu Arg Asn Leu Gly
            900                 905                 910
Lys Asp Thr Ile Lys Ser Lys Leu Ile Gly Ser Lys Glu Asp Asn Cys
            915                 920                 925
Gly Trp Glu Ile Tyr Phe Gln Asp Thr Gly Leu Val Phe Asn Met Ile
            930                 935                 940
Asp Ser Asn Gly Asn Glu Lys Asn Ile Tyr Leu Ser Asp Val Ser Asn
945                 950                 955                 960
Asn Ser Trp His Tyr Ile Thr Ile Ser Val Asp Arg Leu Lys Glu Gln
            965                 970                 975
Leu Leu Ile Phe Ile Asp Asp Asn Leu Val Ala Asn Glu Ser Ile Lys
            980                 985                 990
```

-continued

```
Glu Ile Leu Asn Ile Tyr Ser Ser Asn Ile Ile Ser Leu Leu Ser Glu
            995                 1000                1005

Asn Asn Pro Ser Tyr Ile Glu Gly Leu Thr Ile Leu Asn Lys Pro
    1010                1015                1020

Thr Thr Ser Gln Glu Val Leu Ser Asn Tyr Phe Glu Val Leu Asn
    1025                1030                1035

Asn Ser Tyr Ile Arg Asp Ser Asn Glu Glu Arg Leu Glu Tyr Asn
    1040                1045                1050

Lys Thr Tyr Gln Leu Tyr Asn Tyr Val Phe Ser Asp Lys Pro Ile
    1055                1060                1065

Cys Glu Val Lys Gln Asn Asn Ile Tyr Leu Thr Ile Asn Asn
    1070                1075                1080

Thr Asn Asn Leu Asn Leu Gln Ala Ser Lys Phe Lys Leu Leu Ser
    1085                1090                1095

Ile Asn Pro Asn Lys Gln Tyr Val Gln Lys Leu Asp Glu Val Ile
    1100                1105                1110

Ile Ser Val Leu Asp Asn Met Glu Lys Tyr Ile Asp Ile Ser Glu
    1115                1120                1125

Asp Asn Arg Leu Gln Leu Ile Asp Asn Lys Asn Asn Ala Lys Lys
    1130                1135                1140

Met Ile Ile Ser Asn Asp Ile Phe Ile Ser Asn Cys Leu Thr Leu
    1145                1150                1155

Ser Tyr Asn Gly Lys Tyr Ile Cys Leu Ser Met Lys Asp Glu Asn
    1160                1165                1170

His Asn Trp Met Ile Cys Asn Asn Asp Met Ser Lys Tyr Leu Tyr
    1175                1180                1185

Leu Trp Ser Phe Lys
    1190

<210> SEQ ID NO 24
<211> LENGTH: 1198
<212> TYPE: PRT
<213> ORGANISM: C. botulinum

<400> SEQUENCE: 24

Met Asn Ile Asn Asp Asn Leu Ser Ile Asn Ser Pro Val Asp Asn Lys
1               5                   10                  15

Asn Val Val Val Val Arg Ala Arg Lys Thr Asp Thr Val Phe Lys Ala
                20                  25                  30

Phe Lys Val Ala Pro Asn Ile Trp Val Ala Pro Glu Arg Tyr Tyr Gly
            35                  40                  45

Glu Ser Leu Ser Ile Asp Glu Glu Tyr Lys Val Asp Gly Gly Ile Tyr
        50                  55                  60

Asp Ser Asn Phe Leu Ser Gln Asp Ser Glu Lys Asp Lys Phe Leu Gln
65                  70                  75                  80

Ala Ile Ile Thr Leu Leu Lys Arg Ile Asn Ser Thr Asn Ala Gly Glu
                85                  90                  95

Lys Leu Leu Ser Leu Ile Ser Thr Ala Ile Pro Phe Pro Tyr Gly Tyr
                100                 105                 110

Ile Gly Gly Gly Tyr Tyr Ala Pro Asn Met Ile Thr Phe Gly Ser Ala
            115                 120                 125

Pro Lys Ser Asn Lys Lys Leu Asn Ser Leu Ile Ser Ser Thr Ile Pro
        130                 135                 140

Phe Pro Tyr Ala Gly Tyr Arg Glu Thr Asn Tyr Leu Ser Ser Glu Asp
```

```
                145                 150                 155                 160
Asn Lys Ser Phe Tyr Ala Ser Asn Ile Val Ile Phe Gly Pro Gly Ala
                165                 170                 175
Asn Ile Val Glu Asn Asn Thr Val Phe Tyr Lys Lys Glu Asp Ala Glu
                180                 185                 190
Asn Gly Met Gly Thr Met Thr Glu Ile Trp Phe Gln Pro Phe Leu Thr
                195                 200                 205
Tyr Lys Tyr Asp Glu Phe Tyr Ile Asp Pro Ala Ile Glu Leu Ile Lys
                210                 215                 220
Cys Leu Ile Lys Ser Leu Tyr Phe Leu Tyr Gly Ile Lys Pro Ser Asp
225                 230                 235                 240
Asp Leu Val Ile Pro Tyr Arg Leu Arg Ser Glu Leu Glu Asn Ile Glu
                245                 250                 255
Tyr Ser Gln Leu Asn Ile Val Asp Leu Leu Val Ser Gly Gly Ile Asp
                260                 265                 270
Pro Lys Phe Ile Asn Thr Asp Pro Tyr Trp Phe Ile Asp Asn Tyr Phe
                275                 280                 285
Ser Asn Ala Lys Lys Val Phe Glu Asp His Arg Asn Ile Tyr Glu Thr
                290                 295                 300
Glu Ile Glu Gly Asn Asn Ala Ile Gly Asn Asp Ile Lys Leu Arg Leu
305                 310                 315                 320
Lys Gln Lys Phe Arg Ile Asn Ile Asn Asp Ile Trp Glu Leu Asn Leu
                325                 330                 335
Asn Tyr Phe Ser Lys Glu Phe Ser Ile Met Met Pro Asp Arg Phe Asn
                340                 345                 350
Asn Ala Leu Lys His Phe Tyr Arg Lys Gln Tyr Tyr Lys Ile Asp Tyr
                355                 360                 365
Pro Glu Asn Tyr Ser Ile Asn Gly Phe Val Asn Gly Gln Ile Asn Ala
                370                 375                 380
Gln Leu Ser Leu Ser Asp Arg Asn Gln Asp Ile Ile Asn Lys Pro Glu
385                 390                 395                 400
Glu Ile Ile Asn Leu Leu Asn Gly Asn Asn Val Ser Leu Met Arg Ser
                405                 410                 415
Asn Ile Tyr Gly Asp Gly Leu Lys Ser Thr Val Asp Asp Phe Tyr Ser
                420                 425                 430
Asn Tyr Lys Ile Pro Tyr Asn Arg Ala Tyr Glu Tyr His Phe Asn Asn
                435                 440                 445
Ser Asn Asp Ser Ser Leu Asp Asn Val Asn Ile Gly Val Ile Asp Asn
                450                 455                 460
Ile Pro Glu Ile Ile Asp Val Asn Pro Tyr Lys Glu Asn Cys Asp Lys
465                 470                 475                 480
Phe Ser Pro Val Gln Lys Ile Thr Ser Thr Arg Glu Ile Asn Thr Asn
                485                 490                 495
Ile Pro Trp Pro Ile Asn Tyr Leu Gln Ala Gln Asn Thr Asn Asn Glu
                500                 505                 510
Lys Phe Ser Leu Ser Ser Asp Phe Val Glu Val Val Ser Ser Lys Asp
                515                 520                 525
Lys Ser Leu Val Tyr Ser Phe Leu Ser Asn Val Met Phe Tyr Leu Asp
                530                 535                 540
Ser Ile Lys Asp Asn Ser Pro Ile Asp Thr Asp Lys Lys Tyr Tyr Leu
545                 550                 555                 560
Trp Leu Arg Glu Ile Phe Arg Asn Tyr Ser Phe Asp Ile Thr Ala Thr
                565                 570                 575
```

-continued

Gln Glu Ile Asn Thr Asp Cys Gly Ile Asn Lys Val Val Thr Trp Phe
            580                 585                 590

Gly Lys Ala Leu Asn Ile Leu Asn Thr Ser Asp Ser Phe Val Glu Glu
            595                 600                 605

Phe Gln Asn Leu Gly Pro Ile Ser Leu Ile Asn Lys Lys Glu Asn Leu
            610                 615                 620

Ser Met Pro Lys Ile Glu Ile Asp Glu Ile Pro Asn Ser Met Leu Asn
625                 630                 635                 640

Leu Ser Phe Lys Asp Leu Ser Glu Asn Leu Phe Asn Ile Phe Ser Lys
            645                 650                 655

Asn Asn Ser Tyr Phe Glu Lys Ile Tyr Tyr Asp Phe Leu Asp Gln Trp
            660                 665                 670

Trp Thr Gln Tyr Tyr Ser Gln Tyr Phe Asp Leu Ile Cys Met Ala Lys
            675                 680                 685

Arg Ser Val Leu Ala Gln Glu Ser Leu Ile Lys Lys Ile Ile Gln Lys
            690                 695                 700

Lys Leu Ser Tyr Leu Ile Gly Asn Ser Asn Ile Ser Ser Asp Asn Leu
705                 710                 715                 720

Ala Leu Met Asn Leu Thr Thr Thr Asn Thr Leu Arg Asp Ile Ser Asn
            725                 730                 735

Glu Ser Gln Ile Ala Met Asn Asn Val Asn Asn Phe Leu Asn Asn Val
            740                 745                 750

Ala Ile Cys Val Phe Gln Thr Asn Ile Tyr Pro Lys Phe Ile Ser Phe
            755                 760                 765

Met Glu Gln Cys Ile Asn Asn Ile Asn Lys Asn Thr Arg Glu Phe Ile
            770                 775                 780

Gln Lys Cys Thr Asn Ile Thr Glu Asn Glu Lys Leu Gln Leu Ile Asn
785                 790                 795                 800

Gln Asn Ile Phe Ser Ser Leu Asp Phe Asp Phe Leu Asn Ile Glu Asn
            805                 810                 815

Leu Lys Ser Leu Phe Asn Ser Glu Thr Gly Leu Leu Ile Lys Glu Glu
            820                 825                 830

Thr Ser Pro Tyr Glu Leu Val Leu Tyr Ala Phe Gln Glu Pro Gly Asn
            835                 840                 845

Asn Ala Ile Gly Asp Ala Ser Gly Lys Asn Thr Ser Ile Glu Tyr Ser
            850                 855                 860

Lys Asp Ile Gly Leu Val Tyr Gly Ile Asn Ser Asp Ala Leu Tyr Leu
865                 870                 875                 880

Asn Gly Ser Asn Gln Ser Ile Ser Phe Ser Asn Asp Phe Phe Glu Asn
            885                 890                 895

Gly Leu Thr Asn Ser Phe Ser Ile Tyr Phe Trp Leu Arg Asn Leu Gly
            900                 905                 910

Lys Asp Thr Ile Lys Ser Lys Leu Ile Gly Ser Lys Glu Asp Asn Cys
            915                 920                 925

Gly Trp Glu Ile Tyr Phe Gln Asp Thr Gly Leu Val Phe Asn Met Ile
            930                 935                 940

Asp Ser Asn Gly Asn Glu Lys Asn Ile Tyr Leu Ser Asp Val Ser Asn
945                 950                 955                 960

Asn Ser Trp His Tyr Ile Thr Ile Ser Val Asp Arg Leu Lys Glu Gln
            965                 970                 975

Leu Leu Ile Phe Ile Asp Asp Asn Leu Val Ala Asn Glu Ser Ile Lys
            980                 985                 990

```
Glu Ile Leu Asn Ile Tyr Ser Ser Asn Thr Ile Ser Leu Val Asn Glu
        995                 1000                1005

Asn Asn Pro Ile Tyr Val Glu Gly Leu Ser Ile Leu Asn Arg Ser
    1010                1015                1020

Ile Thr Ser Glu Glu Val Val Asn Asn Tyr Phe Thr Tyr Leu Asn
    1025                1030                1035

Asn Ser Tyr Ile Arg Asp Ile Ser Gly Glu Arg Leu Glu Tyr Asn
    1040                1045                1050

Lys Thr Tyr Glu Leu Tyr Asn Tyr Val Phe Pro Glu Ser Ser Leu
    1055                1060                1065

Tyr Glu Val Thr Glu Asn Asn Asn Ile Tyr Leu Ser Ile Lys Asn
    1070                1075                1080

Thr Asn Asn Leu Asn Ile Gln Gly Ala Lys Phe Lys Leu Ile Asn
    1085                1090                1095

Ile Asp Ala Asn Lys Gln Tyr Val Gln Lys Trp Asp Glu Gly Val
    1100                1105                1110

Val Cys Leu Leu Gly Asp Glu Glu Lys Tyr Val Asp Ile Ser Ser
    1115                1120                1125

Glu Asn Asn Arg Ile Gln Leu Val Ser Ser Lys Asp Thr Ala Lys
    1130                1135                1140

Arg Ile Ile Phe Asn Asn Asp Ile Phe Arg Pro Asn Cys Leu Thr
    1145                1150                1155

Phe Ala Tyr Asn Asn Lys Tyr Leu Ser Leu Ser Leu Arg Asp Arg
    1160                1165                1170

Asn Tyr Asn Trp Met Ile Cys Asn Asn Asn Asp Asn Ile Pro Lys
    1175                1180                1185

Ala Ala His Leu Trp Ala Leu Lys Gly Ile
    1190                1195

<210> SEQ ID NO 25
<211> LENGTH: 1197
<212> TYPE: PRT
<213> ORGANISM: C. botulinum

<400> SEQUENCE: 25

Met Asn Ile Asn Asp Asn Leu Ser Ile Asn Ser Pro Val Asp Asn Lys
1               5                   10                  15

Asn Val Val Val Val Arg Ala Arg Lys Thr Asp Thr Val Phe Lys Ala
                20                  25                  30

Phe Lys Val Ala Pro Asn Ile Trp Val Ala Pro Glu Arg Tyr Tyr Gly
            35                  40                  45

Glu Ser Leu Ser Ile Asp Glu Glu Tyr Lys Val Asp Gly Gly Ile Tyr
        50                  55                  60

Asp Ser Asn Phe Leu Ser Gln Asp Ser Glu Lys Asp Lys Phe Leu Gln
65                  70                  75                  80

Ala Ile Ile Thr Leu Leu Lys Arg Ile Asn Ser Thr Asn Ala Gly Glu
                85                  90                  95

Lys Leu Leu Ser Leu Ile Ser Thr Ala Ile Pro Phe Pro Tyr Gly Tyr
            100                 105                 110

Ile Gly Gly Gly Tyr Tyr Ala Pro Asn Met Ile Thr Phe Gly Ser Ala
        115                 120                 125

Pro Lys Ser Asn Lys Lys Leu Asn Ser Leu Ile Ser Ser Thr Ile Pro
    130                 135                 140

Phe Pro Tyr Ala Gly Tyr Arg Glu Thr Asn Tyr Leu Ser Ser Glu Asp
145                 150                 155                 160
```

-continued

Asn Lys Ser Phe Tyr Ala Ser Asn Ile Val Ile Phe Gly Pro Gly Ala
            165                 170                 175
Asn Ile Val Glu Asn Asn Thr Val Phe Tyr Lys Lys Glu Asp Ala Glu
        180                 185                 190
Asn Gly Met Gly Thr Met Thr Glu Ile Trp Phe Gln Pro Phe Leu Thr
        195                 200                 205
Tyr Lys Tyr Asp Glu Phe Tyr Ile Asp Pro Ala Ile Glu Leu Ile Lys
    210                 215                 220
Cys Leu Ile Lys Ser Leu Tyr Phe Leu Tyr Gly Ile Lys Pro Ser Asp
225                 230                 235                 240
Asp Leu Val Ile Pro Tyr Arg Leu Arg Ser Glu Leu Glu Asn Ile Glu
                245                 250                 255
Tyr Ser Gln Leu Asn Ile Val Asp Leu Val Ser Gly Gly Ile Asp
            260                 265                 270
Pro Lys Phe Ile Asn Thr Asp Pro Tyr Trp Phe Thr Asp Asn Tyr Phe
        275                 280                 285
Ser Asn Ala Lys Lys Val Phe Glu Asp His Arg Asn Ile Tyr Glu Thr
        290                 295                 300
Gln Ile Glu Gly Asn Asn Ala Ile Gly Asn Asp Ile Lys Leu Arg Leu
305                 310                 315                 320
Lys Gln Lys Phe Arg Ile Asn Ile Asn Asp Ile Trp Glu Leu Asn Leu
                325                 330                 335
Asn Tyr Phe Ser Lys Glu Phe Ser Ile Met Met Pro Asp Arg Phe Asn
            340                 345                 350
Asn Ala Leu Lys His Phe Tyr Arg Lys Gln Tyr Tyr Lys Ile Asp Tyr
        355                 360                 365
Pro Glu Asn Tyr Ser Ile Asn Gly Phe Val Asn Gly Gln Ile Asn Val
    370                 375                 380
Gln Leu Ser Leu Ser Asp Arg Asn Gln Asp Ile Ile Asn Lys Pro Glu
385                 390                 395                 400
Glu Ile Ile Asn Leu Leu Asn Gly Asn Val Ser Leu Met Arg Ser
                405                 410                 415
Asn Ile Tyr Gly Asp Gly Leu Lys Ser Thr Val Asp Asp Phe Tyr Ser
            420                 425                 430
Asn Tyr Lys Ile Pro Tyr Asn Arg Ala Tyr Glu Tyr His Phe Asn Asn
        435                 440                 445
Ser Asn Asp Ser Ser Leu Asp Asn Val Asn Ile Gly Val Ile Asp Asn
    450                 455                 460
Ile Pro Glu Ile Ile Asp Val Asn Pro Tyr Lys Glu Asn Cys Asp Lys
465                 470                 475                 480
Phe Ser Pro Val Gln Lys Ile Thr Ser Thr Arg Glu Ile Asn Thr Asn
                485                 490                 495
Ile Pro Trp Pro Ile Asn Tyr Leu Gln Ala Gln Asn Thr Asn Asn Glu
            500                 505                 510
Lys Phe Ser Leu Ser Ser Asp Phe Val Glu Val Ser Ser Lys Asp
        515                 520                 525
Lys Ser Leu Val Tyr Ser Phe Leu Ser Asn Val Met Phe Tyr Leu Asp
    530                 535                 540
Ser Ile Lys Asp Asn Ser Pro Ile Asp Thr Lys Lys Tyr Tyr Leu
545                 550                 555                 560
Trp Leu Arg Glu Ile Phe Arg Asn Tyr Ser Phe Asp Ile Thr Ala Thr
                565                 570                 575

-continued

```
Gln Glu Ile Asn Thr Asp Cys Gly Ile Asn Lys Val Val Thr Trp Phe
            580                 585                 590
Gly Lys Ala Leu Asn Ile Leu Asn Thr Ser Asp Ser Phe Val Glu Glu
        595                 600                 605
Phe Gln Asn Leu Gly Pro Ile Ser Leu Ile Asn Lys Lys Glu Asn Leu
    610                 615                 620
Ser Met Pro Ile Ile Glu Ile Tyr Gly Ile Pro Asn Asp Met Leu Gly
625                 630                 635                 640
Leu Pro Leu Asn Asp Leu Asn Glu Lys Leu Phe Asn Ile Tyr Leu Lys
                645                 650                 655
Asn Ile Leu Tyr Phe Lys Lys Val Tyr Phe Asn Phe Leu Asp Gln Trp
            660                 665                 670
Trp Thr Glu Tyr Tyr Ser Gln Tyr Phe Asp Leu Ile Cys Met Ala Lys
        675                 680                 685
Gln Ser Ile Leu Ala Gln Glu Lys Leu Ile Lys Gln Ile Ile Gln Asn
    690                 695                 700
Lys Leu Gln Asp Leu Phe Lys Ala Asp Ile Ser Met Asp Lys Leu Asn
705                 710                 715                 720
Leu Met Asn Leu Ala Thr Glu Lys Thr Phe Ile Asp Leu Ser Asn Glu
                725                 730                 735
Ser Gln Ile Ala Ile Asn Asn Ile Asn Asp Phe Leu Asn Lys Ser Ala
            740                 745                 750
Ile Cys Val Phe Asp Thr Asn Ile Tyr Pro Lys Phe Ile Ser Phe Met
        755                 760                 765
Glu Gln Cys Ile Asn Ser Val Asn Ser Asn Val Thr Ala Phe Ile Gln
    770                 775                 780
Lys Cys Thr Asn Ile Thr Glu Asp Glu Lys Leu Gln Leu Ile Lys Leu
785                 790                 795                 800
Asn Thr Phe Met Asn Ile Asp Phe Glu Phe Phe Asp Ile Gln Ser Ile
                805                 810                 815
Lys Asp Leu Ile Thr Ser Glu Thr Asp Leu Ile Lys Glu Glu Lys Glu
            820                 825                 830
Ser Asp Tyr Asn Leu Phe Leu Phe Thr Leu Gln Glu Asp Asn Asn Lys
        835                 840                 845
Val Ile Glu Asp Ile Ser Gly Lys Asn Thr Leu Val Lys Tyr Ser Asp
    850                 855                 860
Ser Ile Ser Leu Val Tyr Gly Val Asn Gly Asp Ala Leu Tyr Leu Lys
865                 870                 875                 880
Glu Pro Asp Glu Ser Val Ser Phe Ser Asn Lys Ala Phe Glu Asn Gly
                885                 890                 895
Leu Thr Asn Ser Phe Ser Ile Cys Phe Trp Leu Arg Asn Leu Gly Glu
            900                 905                 910
Asp Ile Ile Thr Ser Lys Leu Ile Glu Asn Lys Ala Asp Asn Cys Gly
        915                 920                 925
Trp Glu Ile Tyr Phe Glu Asn Asn Gly Leu Val Phe Ser Ile Val Asp
    930                 935                 940
Cys Asn Gly Asn Glu Glu Asn Ile Tyr Leu Ser Asp Val Ile Ser Lys
945                 950                 955                 960
Asn Trp Tyr Tyr Ile Ser Ile Ser Ile Asp Arg Leu Arg Asn Gln Leu
                965                 970                 975
Leu Ile Phe Ile Asn Asp Lys Leu Ile Ala Asn Gln Ser Ile Glu Gln
            980                 985                 990
Ile Leu Asn Ile Tyr Ser Ser Asn  Thr Ile Ser Leu Val  Asn Glu Asn
```

```
                 995                1000                1005
Asn Pro Ile Tyr Ile Glu Gly Leu Ser Ile Leu Asn Arg Ser Ile
    1010                1015                1020

Thr Ser Glu Glu Val Val Asn Asn Tyr Phe Ser Tyr Leu Asn Asn
    1025                1030                1035

Ser Tyr Ile Arg Asp Ile Ser Gly Glu Arg Leu Glu Tyr Asn Lys
    1040                1045                1050

Thr Tyr Glu Leu Tyr Asn Tyr Val Phe Pro Glu Asn Ser Leu Tyr
    1055                1060                1065

Glu Val Thr Glu Asn Asn Asn Ile Tyr Leu Ser Ile Lys Asp Thr
    1070                1075                1080

Asn Asn Leu Asn Ile Gln Gly Ala Lys Phe Lys Leu Ile Asn Ile
    1085                1090                1095

Asp Ala Asn Lys Gln Tyr Val Gln Lys Trp Asp Glu Gly Val Val
    1100                1105                1110

Cys Leu Leu Gly Asp Glu Glu Lys Tyr Val Asp Ile Ser Ser Glu
    1115                1120                1125

Asn Asn Arg Ile Gln Leu Val Asn Ser Lys Asp Thr Ala Lys Arg
    1130                1135                1140

Ile Ile Phe Asn Asn Asp Ile Phe Met Pro Asn Cys Leu Thr Phe
    1145                1150                1155

Ala Tyr Asn Asn Lys Tyr Leu Ser Leu Ser Leu Arg Asp Arg Asn
    1160                1165                1170

Tyr Asn Trp Met Ile Cys Asn Asn Asp Asn Ile Pro Lys Ala
    1175                1180                1185

Ala His Leu Trp Ala Leu Lys Gly Ile
    1190                1195

<210> SEQ ID NO 26
<211> LENGTH: 1193
<212> TYPE: PRT
<213> ORGANISM: C. botulinum

<400> SEQUENCE: 26

Met Asp Ile Asn Asp Asp Leu Asn Ile Asn Ser Pro Val Asp Asn Lys
1               5                   10                  15

Asn Val Val Ile Val Arg Ala Arg Lys Thr Asn Thr Phe Phe Lys Ala
            20                  25                  30

Phe Lys Val Ala Pro Asn Ile Trp Val Ala Pro Glu Arg Tyr Tyr Gly
        35                  40                  45

Glu Pro Leu His Ile Ala Glu Glu Tyr Lys Leu Asp Gly Gly Ile Tyr
    50                  55                  60

Asp Ser Asn Phe Leu Ser Gln Asp Ser Glu Arg Glu Asn Phe Leu Gln
65                  70                  75                  80

Ala Ile Ile Ile Leu Leu Lys Arg Ile Asn Asn Thr Ile Ser Gly Lys
                85                  90                  95

Gln Leu Leu Ser Leu Ile Ser Thr Ala Ile Pro Phe Pro Tyr Gly Tyr
            100                 105                 110

Ile Gly Gly Gly Tyr Ser Ser Pro Asn Ile Phe Thr Phe Gly Lys Thr
        115                 120                 125

Pro Arg Thr Asn Lys Lys Leu Asn Ser Leu Val Thr Ser Thr Ile Pro
    130                 135                 140

Phe Pro Phe Gly Gly Tyr Arg Glu Thr Asn Tyr Ile Glu Ser Gln Asn
145                 150                 155                 160
```

-continued

```
Asn Lys Asn Phe Tyr Ala Ser Asn Ile Ile Phe Gly Pro Gly Ser
                165                 170                 175

Asn Ile Val Glu Asn Val Ile Tyr Lys Lys Asn Asp Ala Glu
            180                 185                 190

Asn Gly Met Gly Thr Met Ala Glu Ile Val Phe Gln Pro Leu Leu Thr
            195                 200                 205

Tyr Lys Tyr Asn Lys Phe Tyr Ile Asp Pro Ala Met Glu Leu Thr Lys
        210                 215                 220

Cys Leu Ile Lys Ser Leu Tyr Phe Leu Tyr Gly Ile Lys Pro Ser Gly
225                 230                 235                 240

Asn Leu Val Val Pro Tyr Arg Leu Arg Thr Glu Leu Asp Asn Lys Gln
                245                 250                 255

Phe Ser Gln Leu Asn Ile Ile Asp Leu Leu Ile Ser Gly Gly Val Asp
                260                 265                 270

Leu Glu Phe Ile Asn Thr Asn Pro Tyr Trp Phe Thr Asn Ser Tyr Phe
        275                 280                 285

Pro Asn Ser Ile Lys Met Phe Glu Lys Tyr Lys Asn Ile Tyr Lys Thr
        290                 295                 300

Glu Ile Glu Gly Asn Asn Ala Ile Gly Asn Asp Ile Lys Leu Arg Leu
305                 310                 315                 320

Lys Gln Lys Phe Gln Ile Asn Val Gln Asp Ile Trp Asn Leu Asn Leu
                325                 330                 335

Asn Tyr Phe Cys Gln Ser Phe Asn Ser Ile Ile Pro Asp Arg Phe Ser
                340                 345                 350

Asn Ala Leu Lys His Phe Tyr Arg Lys Gln Tyr Tyr Thr Met Asp Tyr
            355                 360                 365

Thr Asp Asn Tyr Asn Ile Asn Gly Phe Val Asn Gly Gln Ile Asn Thr
        370                 375                 380

Lys Leu Pro Leu Ser Asn Lys Asn Thr Asn Ile Ile Ser Lys Pro Glu
385                 390                 395                 400

Lys Val Val Asn Leu Val Asn Glu Asn Asn Ile Ser Leu Met Lys Ser
                405                 410                 415

Asn Ile Tyr Gly Asp Gly Leu Lys Gly Thr Thr Glu Asp Phe Tyr Ser
                420                 425                 430

Thr Tyr Lys Ile Pro Tyr Asp Glu Glu Tyr Glu Tyr Arg Phe Asn Asp
        435                 440                 445

Ser Asp Asn Phe Pro Leu Asn Asn Ile Ser Ile Glu Glu Val Asp Ser
450                 455                 460

Ile Pro Glu Ile Ile Asp Ile Asn Pro Tyr Lys Asp Asn Ser Asp Asn
465                 470                 475                 480

Leu Val Phe Thr Gln Ile Thr Ser Met Thr Glu Glu Val Thr Thr His
                485                 490                 495

Thr Ala Leu Ser Ile Asn Tyr Leu Gln Ala Gln Ile Thr Asn Asn Glu
            500                 505                 510

Asn Phe Thr Leu Ser Ser Asp Phe Ser Lys Val Val Ser Ser Lys Asp
        515                 520                 525

Lys Ser Leu Val Tyr Ser Phe Leu Asp Asn Leu Met Ser Tyr Leu Glu
        530                 535                 540

Thr Ile Lys Asn Asp Arg Pro Ile His Thr Asp Lys Lys Tyr Tyr Leu
545                 550                 555                 560

Trp Leu Lys Glu Val Phe Lys Asn Tyr Ser Phe Asp Ile Asn Leu Thr
                565                 570                 575

Gln Glu Ile Asp Ser Met Cys Gly Ile Asn Gln Val Val Leu Trp Phe
```

-continued

```
                580                 585                 590
Gly Lys Ala Leu Asn Ile Leu Asn Thr Ser Asn Ser Phe Val Glu Glu
            595                 600                 605
Tyr Gln Asp Ser Gly Ala Ile Ser Leu Ile Ser Lys Lys Asp Asn Leu
        610                 615                 620
Arg Glu Pro Asn Ile Glu Ile Asp Asp Ile Ser Asp Ser Leu Leu Gly
625                 630                 635                 640
Leu Ser Phe Lys Asp Leu Asn Asn Lys Leu Tyr Glu Ile Tyr Ser Lys
                645                 650                 655
Asn Ile Val Tyr Phe Lys Lys Ile Tyr Phe Ser Phe Leu Asp Gln Trp
            660                 665                 670
Trp Thr Gln Tyr Tyr Ser Gln Tyr Phe Asp Leu Ile Cys Met Ala Lys
        675                 680                 685
Lys Ser Ile Leu Ala Gln Glu Thr Leu Ile Lys Lys Ile Ile Gln Lys
        690                 695                 700
Lys Leu Ser Tyr Leu Ile Gly Asn Ser Asn Ile Ser Ser Asp Asn Leu
705                 710                 715                 720
Ala Leu Met Asn Leu Thr Thr Thr Asn Thr Leu Arg Asp Ile Ser Asn
                725                 730                 735
Glu Ser Gln Ile Ala Met Asn Asn Val Asp Ser Phe Leu Asn Ser Ala
            740                 745                 750
Ala Ile Cys Val Phe Glu Gly Asn Ile Tyr Pro Lys Phe Ile Ser Phe
        755                 760                 765
Met Glu Gln Cys Ile Asn Asn Ile Asn Lys Asn Thr Arg Glu Phe Ile
        770                 775                 780
Gln Lys Cys Thr Asn Ile Thr Glu Asn Glu Lys Leu Gln Leu Ile Asn
785                 790                 795                 800
Gln Asn Ile Phe Ser Ser Leu Asp Phe Asp Phe Leu Asn Ile Glu Asn
                805                 810                 815
Leu Lys Ser Leu Phe Ser Ser Glu Thr Ala Leu Leu Ile Lys Glu Glu
            820                 825                 830
Thr Ser Pro Tyr Glu Leu Val Leu Tyr Ala Phe Gln Glu Pro Asp Asn
        835                 840                 845
Asn Ala Ile Gly Asp Ala Ser Ala Lys Asn Thr Ser Ile Glu Tyr Ser
        850                 855                 860
Lys Asp Ile Asp Leu Val Tyr Gly Ile Asn Ser Asp Ala Leu Tyr Leu
865                 870                 875                 880
Asn Gly Ser Asn Gln Ser Ile Ser Phe Ser Asn Asp Phe Phe Glu Asn
                885                 890                 895
Gly Leu Thr Asn Ser Phe Ser Ile Tyr Phe Trp Leu Arg Asn Leu Gly
            900                 905                 910
Lys Asp Thr Ile Lys Ser Lys Leu Ile Gly Ser Lys Gly Asp Asn Cys
        915                 920                 925
Gly Trp Glu Ile Tyr Phe Gln Asp Thr Gly Leu Val Phe Asn Met Ile
        930                 935                 940
Asp Ser Asn Gly Asn Glu Lys Asn Ile Tyr Leu Ser Asp Val Ser Asn
945                 950                 955                 960
Asn Ser Trp His Tyr Ile Thr Ile Ser Val Asp Arg Leu Lys Glu Gln
                965                 970                 975
Leu Leu Ile Phe Ile Asp Asp Asn Leu Val Ala Asn Glu Ser Ile Lys
            980                 985                 990
Glu Ile Leu Asn Ile Tyr Ser Ser  Asn Ile Ile Ser Leu  Leu Ser Glu
        995                1000                1005
```

```
Asn Asn Pro Ser Tyr Ile Glu Gly Leu Thr Ile Leu Asn Lys Pro
    1010                1015                1020

Thr Thr Ser Gln Glu Val Leu Asn Asn Tyr Phe Lys Val Leu Asn
    1025                1030                1035

Asn Ser Tyr Ile Arg Asp Ser Asn Glu Glu Arg Leu Glu Tyr Asn
    1040                1045                1050

Lys Thr Tyr Gln Leu Tyr Asn Tyr Val Phe Ser Asp Lys Pro Ile
    1055                1060                1065

Cys Glu Val Lys Gln Asn Asn Asn Ile Tyr Leu Thr Ile Asn Asn
    1070                1075                1080

Thr Asn Asn Leu Asn Leu Gln Pro Ser Lys Phe Lys Leu Leu Ser
    1085                1090                1095

Ile Asn Pro Asn Lys Gln Tyr Val Gln Lys Leu Asp Glu Val Ile
    1100                1105                1110

Ile Ser Val Leu Gly Asn Met Glu Lys Tyr Ile Asp Ile Ser Glu
    1115                1120                1125

Asp Asn Arg Leu Gln Leu Ile Asp Asn Lys Asn Gly Ala Lys Lys
    1130                1135                1140

Met Ile Ile Ser Asn Asp Met Phe Ile Ser Asn Cys Leu Thr Leu
    1145                1150                1155

Ser Cys Gly Gly Lys Tyr Ile Cys Leu Ser Met Lys Asp Glu Asn
    1160                1165                1170

His Asn Trp Met Ile Cys Asn Asp Met Ser Lys Tyr Leu Tyr
    1175                1180                1185

Leu Trp Ser Phe Lys
    1190

<210> SEQ ID NO 27
<211> LENGTH: 1196
<212> TYPE: PRT
<213> ORGANISM: C. botulinum

<400> SEQUENCE: 27

Met Asp Ile Asn Asp Asp Leu Asn Ile Asn Ser Pro Val Asp Asn Lys
1               5                   10                  15

Asn Val Val Ile Val Arg Ala Arg Lys Thr Asn Thr Phe Phe Lys Ala
                20                  25                  30

Phe Lys Val Ala Pro Asn Ile Trp Val Ala Pro Glu Arg Tyr Tyr Gly
            35                  40                  45

Glu Pro Leu Asp Ile Ala Glu Glu Tyr Lys Leu Asp Gly Gly Ile Tyr
        50                  55                  60

Asp Ser Asn Phe Leu Ser Gln Asp Ser Glu Arg Glu Asn Phe Leu Gln
65                  70                  75                  80

Ala Ile Ile Ile Leu Leu Lys Arg Ile Asn Asn Thr Ile Ser Gly Lys
                85                  90                  95

Gln Leu Leu Ser Leu Ile Ser Thr Ala Ile Pro Phe Pro Tyr Gly Tyr
            100                 105                 110

Ile Gly Gly Gly Tyr Ser Ser Pro Asn Ile Phe Thr Phe Gly Lys Thr
        115                 120                 125

Pro Lys Ser Asn Lys Lys Leu Asn Ser Leu Val Thr Ser Thr Ile Pro
    130                 135                 140

Phe Pro Phe Gly Gly Tyr Arg Glu Thr Asn Tyr Ile Glu Ser Gln Asn
145                 150                 155                 160

Asn Lys Asn Phe Tyr Ala Ser Asn Ile Ile Ile Phe Gly Pro Gly Ser
```

-continued

```
                165                 170                 175
Asn Ile Val Glu Asn Asn Val Ile Tyr Tyr Lys Lys Asn Asp Ala Glu
            180                 185                 190
Asn Gly Met Gly Thr Met Ala Glu Ile Val Phe Gln Pro Leu Leu Thr
        195                 200                 205
Tyr Lys Tyr Asn Lys Phe Tyr Ile Asp Pro Ala Met Glu Leu Thr Lys
    210                 215                 220
Cys Leu Ile Lys Ser Leu Tyr Phe Leu Tyr Gly Ile Lys Pro Ser Asp
225                 230                 235                 240
Asn Leu Val Val Pro Tyr Arg Leu Arg Thr Glu Leu Asp Asn Lys Gln
                245                 250                 255
Phe Ser Gln Leu Asn Ile Ile Asp Leu Leu Ile Ser Gly Gly Val Asp
            260                 265                 270
Leu Glu Phe Ile Asn Thr Asn Pro Tyr Trp Phe Thr Asn Ser Tyr Phe
        275                 280                 285
Pro Asn Ser Ile Lys Met Phe Glu Lys Tyr Lys Asn Ile Tyr Lys Thr
    290                 295                 300
Glu Ile Glu Gly Asn Asn Ala Ile Gly Asn Asp Ile Lys Leu Arg Leu
305                 310                 315                 320
Lys Gln Lys Phe Gln Ile Asn Val Gln Asp Ile Trp Asn Leu Asn Leu
                325                 330                 335
Asn Tyr Phe Cys Gln Ser Phe Asn Ser Ile Ile Pro Asp Arg Phe Ser
            340                 345                 350
Asn Ala Leu Lys His Phe Tyr Arg Lys Gln Tyr Tyr Thr Met Asp Tyr
        355                 360                 365
Thr Asp Asn Tyr Asn Ile Asn Gly Phe Val Asn Gly Gln Ile Asn Thr
    370                 375                 380
Lys Leu Pro Leu Ser Asn Lys Asn Thr Asn Ile Ile Ser Lys Pro Glu
385                 390                 395                 400
Lys Val Val Asn Leu Val Asn Glu Asn Asn Ile Ser Leu Met Lys Ser
                405                 410                 415
Asn Ile Tyr Gly Asp Gly Leu Lys Gly Thr Thr Glu Asp Phe Tyr Ser
            420                 425                 430
Thr Tyr Lys Ile Pro Tyr Asn Glu Glu Tyr Glu Tyr Arg Phe Asn Asp
        435                 440                 445
Ser Asp Asn Phe Pro Leu Asn Asn Ile Ser Ile Glu Glu Val Asp Ser
    450                 455                 460
Ile Pro Glu Ile Ile Asp Ile Asn Pro Tyr Lys Asp Asn Ser Asp Asn
465                 470                 475                 480
Leu Val Phe Thr Gln Ile Thr Ser Met Thr Glu Glu Val Thr Thr His
                485                 490                 495
Thr Ala Leu Ser Ile Asn Tyr Leu Gln Ala Gln Ile Thr Asn Asn Glu
            500                 505                 510
Asn Phe Thr Leu Ser Ser Asp Phe Ser Lys Val Val Ser Ser Lys Asp
        515                 520                 525
Lys Ser Leu Val Tyr Ser Phe Leu Asp Asn Leu Met Ser Tyr Leu Glu
    530                 535                 540
Thr Ile Lys Asn Asp Gly Pro Ile Asp Thr Asp Lys Lys Tyr Tyr Leu
545                 550                 555                 560
Trp Leu Lys Glu Val Phe Lys Asn Tyr Ser Phe Asp Ile Asn Leu Thr
                565                 570                 575
Gln Glu Ile Asp Ser Met Cys Gly Ile Asn Glu Val Val Leu Trp Phe
            580                 585                 590
```

```
Gly Lys Ala Leu Asn Ile Leu Asn Thr Ser Asn Ser Phe Val Glu Glu
            595                 600                 605

Tyr Gln Asp Ser Gly Ala Ile Ser Leu Ile Ser Lys Lys Asp Asn Leu
        610                 615                 620

Arg Glu Pro Asn Ile Glu Ile Asp Asp Ile Ser Asp Ser Leu Leu Gly
625                 630                 635                 640

Leu Ser Phe Lys Asp Leu Asn Asn Lys Leu Tyr Glu Ile Tyr Ser Lys
                645                 650                 655

Asn Ile Val Tyr Phe Lys Lys Ile Tyr Phe Ser Phe Leu Asp Gln Trp
            660                 665                 670

Trp Thr Glu Tyr Tyr Ser Gln Tyr Phe Glu Leu Ile Cys Met Ala Lys
        675                 680                 685

Gln Ser Ile Leu Ala Gln Glu Ser Leu Val Lys Gln Ile Val Gln Asn
    690                 695                 700

Lys Phe Thr Asp Leu Ser Lys Ala Ser Ile Pro Pro Asp Thr Leu Lys
705                 710                 715                 720

Leu Ile Arg Glu Thr Thr Glu Lys Thr Phe Ile Asp Leu Ser Asn Glu
                725                 730                 735

Ser Gln Ile Ser Met Asn Arg Val Asp Asn Phe Leu Asn Lys Ala Ser
            740                 745                 750

Ile Cys Val Phe Val Glu Asp Ile Tyr Pro Lys Phe Ile Ser Tyr Met
        755                 760                 765

Glu Lys Tyr Ile Asn Asn Ile Asn Ile Lys Thr Arg Glu Phe Ile Gln
    770                 775                 780

Arg Cys Thr Asn Ile Asn Asp Asn Glu Lys Ser Ile Leu Ile Asn Ser
785                 790                 795                 800

Tyr Thr Phe Lys Thr Ile Asp Phe Lys Phe Leu Asp Ile Gln Ser Ile
                805                 810                 815

Lys Asn Phe Phe Asn Ser Gln Val Glu Gln Val Met Lys Glu Ile Leu
            820                 825                 830

Ser Pro Tyr Gln Leu Leu Leu Phe Ala Ser Lys Gly Pro Asn Ser Asn
        835                 840                 845

Ile Ile Glu Asp Ile Ser Gly Lys Asn Thr Leu Ile Gln Tyr Thr Glu
850                 855                 860

Ser Ile Glu Leu Val Tyr Gly Val Asn Gly Ser Leu Tyr Leu Lys
865                 870                 875                 880

Ser Pro Asn Glu Thr Ile Lys Phe Ser Asn Lys Phe Phe Thr Asn Gly
                885                 890                 895

Leu Thr Asn Asn Phe Thr Ile Cys Phe Trp Leu Arg Phe Thr Gly Lys
            900                 905                 910

Asn Asp Asp Lys Thr Arg Leu Ile Gly Asn Lys Val Asn Asn Cys Gly
        915                 920                 925

Trp Glu Ile Tyr Phe Glu Asp Asn Gly Leu Val Phe Glu Ile Ile Asp
    930                 935                 940

Ser Asn Gly Asn Gln Glu Ser Val Tyr Leu Ser Asn Ile Ile Asn Asp
945                 950                 955                 960

Asn Trp Tyr Tyr Ile Ser Ile Ser Val Asp Arg Leu Lys Asp Gln Leu
                965                 970                 975

Leu Ile Phe Ile Asn Asp Lys Asn Val Ala Asn Val Ser Ile Asp Gln
            980                 985                 990

Ile Leu Ser Ile Tyr Ser Thr Asn  Ile Ile Ser Leu Val  Asn Lys Asn
        995                 1000                1005
```

-continued

```
Asn Ser Ile Tyr Val Glu Glu Leu Ser Val Leu Asp Asn Pro Ile
    1010                1015                1020

Thr Ser Glu Glu Val Ile Arg Asn Tyr Phe Ser Tyr Leu Asp Asn
    1025                1030                1035

Ser Tyr Ile Arg Asp Ser Ser Lys Ser Leu Leu Glu Tyr Asn Lys
    1040                1045                1050

Asn Tyr Gln Leu Tyr Asn Tyr Val Phe Pro Glu Thr Ser Leu Tyr
    1055                1060                1065

Glu Val Asn Asp Asn Lys Ser Tyr Leu Ser Leu Lys Asn Thr
    1070                1075                1080

Asp Gly Ile Asn Ile Ser Ser Val Lys Phe Lys Leu Ile Asn Ile
    1085                1090                1095

Asp Glu Ser Lys Val Tyr Val Gln Lys Trp Asp Glu Cys Ile Ile
    1100                1105                1110

Cys Val Leu Asp Gly Thr Glu Lys Tyr Leu Asp Ile Ser Pro Glu
    1115                1120                1125

Asn Asn Arg Ile Gln Leu Val Ser Ser Lys Asp Asn Ala Lys Lys
    1130                1135                1140

Ile Thr Val Asn Thr Asp Leu Phe Arg Pro Asp Cys Ile Thr Phe
    1145                1150                1155

Ser Tyr Asn Asp Lys Tyr Phe Ser Leu Ser Leu Arg Asp Gly Asp
    1160                1165                1170

Tyr Asn Trp Met Ile Cys Asp Asn Asn Lys Val Pro Lys Gly
    1175                1180                1185

Ala His Leu Trp Ile Leu Glu Ser
    1190                1195

<210> SEQ ID NO 28
<211> LENGTH: 1196
<212> TYPE: PRT
<213> ORGANISM: C. botulinum

<400> SEQUENCE: 28

Met Asp Ile Asn Asp Asp Leu Asn Ile Asn Ser Pro Val Asp Asn Lys
1               5                   10                  15

Asn Val Val Ile Val Arg Ala Arg Lys Thr Asn Thr Phe Phe Lys Ala
                20                  25                  30

Phe Lys Val Ala Pro Asn Ile Trp Val Ala Pro Glu Arg Tyr Tyr Gly
            35                  40                  45

Glu Pro Leu Asp Ile Ala Glu Glu Tyr Lys Leu Asp Gly Gly Ile Tyr
        50                  55                  60

Asp Ser Asn Phe Leu Ser Gln Asp Ser Glu Arg Glu Asn Phe Leu Gln
65                  70                  75                  80

Ala Ile Ile Thr Leu Leu Lys Arg Ile Asn Asn Thr Ile Ser Gly Lys
                85                  90                  95

Gln Leu Leu Ser Leu Ile Ser Thr Ala Ile Pro Phe Pro Tyr Gly Tyr
                100                 105                 110

Val Gly Gly Gly Tyr Ser Ser Pro Asn Ile Phe Thr Phe Gly Lys Thr
            115                 120                 125

Pro Lys Ser Asn Lys Lys Leu Asn Ser Leu Val Thr Ser Thr Ile Pro
        130                 135                 140

Phe Pro Phe Gly Gly Tyr Arg Glu Thr Asn Tyr Ile Glu Ser Gln Asn
145                 150                 155                 160

Asn Lys Asn Phe Tyr Ala Ser Asn Ile Val Ile Phe Gly Pro Gly Ser
                165                 170                 175
```

-continued

```
Asn Ile Val Glu Asn Val Ile Cys Tyr Lys Lys Asn Asp Ala Glu
            180                 185                 190

Asn Gly Met Gly Thr Met Ala Glu Ile Leu Phe Gln Pro Leu Leu Thr
        195                 200                 205

Tyr Lys Tyr Asn Lys Phe Tyr Ile Asp Pro Ala Met Glu Leu Thr Lys
    210                 215                 220

Cys Leu Ile Lys Ser Leu Tyr Phe Leu Tyr Gly Ile Lys Pro Ser Asp
225                 230                 235                 240

Asp Leu Val Val Pro Tyr Arg Leu Arg Thr Glu Leu Asp Asn Lys Gln
                245                 250                 255

Phe Ser Gln Leu Asn Ile Ile Asp Leu Leu Ile Ser Gly Gly Val Asp
            260                 265                 270

Leu Glu Phe Ile Asn Thr Asn Pro Tyr Trp Phe Thr Asn Ser Tyr Phe
        275                 280                 285

Ser Asn Ser Ile Lys Met Phe Glu Lys Tyr Lys Asn Ile Tyr Glu Thr
    290                 295                 300

Glu Ile Glu Gly Asn Asn Ala Ile Gly Asn Asp Ile Lys Leu Arg Leu
305                 310                 315                 320

Lys Gln Lys Phe Gln Asn Ser Val Gln Asp Ile Trp Asn Leu Asn Leu
                325                 330                 335

Asn Tyr Phe Ser Lys Glu Phe Asn Ser Ile Ile Pro Asp Arg Phe Ser
            340                 345                 350

Asn Ala Leu Lys His Phe Tyr Arg Lys Gln Tyr Tyr Thr Met Asp Tyr
        355                 360                 365

Gly Asp Asn Tyr Asn Ile Asn Gly Phe Val Asn Gly Gln Ile Asn Thr
    370                 375                 380

Lys Leu Pro Leu Ser Asp Lys Asn Thr Asn Ile Ile Ser Lys Pro Glu
385                 390                 395                 400

Lys Val Val Asn Leu Val Asn Ala Asn Asn Ile Ser Leu Met Lys Ser
                405                 410                 415

Asn Ile Tyr Gly Asp Gly Leu Lys Gly Thr Thr Glu Asp Phe Tyr Ser
            420                 425                 430

Thr Tyr Lys Ile Pro Tyr Asn Glu Glu Tyr Glu Tyr Arg Phe Asn Asp
        435                 440                 445

Ser Asp Asn Phe Pro Leu Asn Asn Ile Ser Ile Glu Glu Val Asp Ser
    450                 455                 460

Ile Pro Glu Ile Ile Asp Ile Asn Pro Tyr Lys Asp Asn Ser Asp Asp
465                 470                 475                 480

Leu Leu Phe Thr Gln Ile Thr Ser Thr Thr Glu Glu Val Ile Thr His
                485                 490                 495

Thr Ala Leu Pro Val Asn Tyr Leu Gln Ala Gln Ile Ile Thr Asn Glu
            500                 505                 510

Asn Phe Thr Leu Ser Ser Asp Phe Ser Lys Val Val Ser Ser Lys Asp
        515                 520                 525

Lys Ser Leu Val Tyr Ser Phe Leu Asp Asn Leu Met Ser Tyr Leu Glu
    530                 535                 540

Thr Ile Lys Asn Asp Gly Pro Ile Asp Thr Asp Lys Lys Tyr Tyr Leu
545                 550                 555                 560

Trp Leu Lys Glu Val Phe Lys Asn Tyr Ser Phe Asp Ile Asn Leu Thr
                565                 570                 575

Gln Glu Ile Asp Ser Ser Cys Gly Ile Asn Glu Val Val Ile Trp Phe
            580                 585                 590
```

-continued

```
Gly Lys Ala Leu Asn Ile Leu Asn Thr Ser Asn Ser Phe Val Glu Glu
            595                 600                 605

Tyr Gln Asn Ser Gly Pro Ile Ser Leu Ile Ser Lys Lys Asp Asn Leu
            610                 615                 620

Ser Glu Pro Asn Ile Glu Ile Asp Asp Ile Pro Asp Ser Leu Leu Gly
625                 630                 635                 640

Leu Ser Phe Lys Asp Leu Asn Asn Lys Leu Tyr Glu Ile Tyr Ser Lys
                645                 650                 655

Asn Arg Val Tyr Phe Arg Lys Ile Tyr Phe Asn Phe Leu Asp Gln Trp
                660                 665                 670

Trp Thr Glu Tyr Tyr Ser Gln Tyr Phe Glu Leu Ile Cys Met Ala Lys
                675                 680                 685

Gln Ser Ile Leu Ala Gln Glu Ser Val Val Lys Gln Ile Ile Gln Asn
            690                 695                 700

Lys Phe Thr Asp Leu Ser Lys Ala Ser Ile Pro Pro Asp Thr Leu Lys
705                 710                 715                 720

Leu Ile Lys Glu Thr Thr Glu Lys Thr Phe Ile Asp Leu Ser Asn Glu
                725                 730                 735

Ser Gln Ile Ser Met Asn Arg Val Asp Asn Phe Leu Asn Lys Ala Ser
            740                 745                 750

Ile Cys Val Phe Val Glu Asp Ile Tyr Pro Lys Phe Ile Ser Tyr Met
            755                 760                 765

Glu Lys Tyr Ile Asn Asn Ile Asn Ile Lys Thr Arg Glu Phe Ile Gln
            770                 775                 780

Arg Cys Thr Asn Ile Asn Asp Asn Glu Lys Ser Ile Leu Ile Asn Ser
785                 790                 795                 800

Tyr Thr Phe Lys Thr Ile Asp Phe Lys Phe Leu Asn Ile Gln Ala Ile
                805                 810                 815

Lys Asn Phe Phe Asn Ser Gln Val Glu Gln Val Met Lys Glu Met Leu
                820                 825                 830

Ser Pro Tyr Gln Leu Leu Phe Ala Thr Arg Gly Pro Asn Ser Asn
            835                 840                 845

Ile Ile Glu Asp Ile Ser Gly Lys Asn Thr Leu Ile Gln Tyr Thr Glu
850                 855                 860

Ser Val Glu Leu Val Tyr Gly Val Asn Gly Glu Ser Leu Tyr Leu Lys
865                 870                 875                 880

Ser Pro Asn Glu Thr Val Glu Phe Ser Asn Asn Phe Thr Asn Gly
            885                 890                 895

Leu Thr Asn Asn Phe Thr Ile Cys Phe Trp Leu Arg Phe Thr Gly Lys
            900                 905                 910

Asp Asp Asp Lys Thr Arg Leu Ile Gly Asn Lys Val Asn Asn Cys Gly
            915                 920                 925

Trp Glu Ile Tyr Phe Glu Asp Asn Gly Leu Val Phe Glu Ile Ile Asp
            930                 935                 940

Ser Asn Gly Asn Gln Glu Ser Val Tyr Leu Ser Asn Val Ile Asn Asn
945                 950                 955                 960

Asn Trp Tyr Tyr Ile Ser Ile Ser Val Asp Arg Leu Lys Asp Gln Leu
                965                 970                 975

Leu Ile Phe Ile Asn Asp Lys Asn Val Ala Asn Val Ser Ile Glu Gln
                980                 985                 990

Ile Leu Asn Ile Tyr Ser Thr Asn  Val Ile Ser Leu Val  Asn Lys Asn
            995                 1000                1005

Asn Ser  Ile Tyr Val Glu Glu  Leu Ser Val Leu Asp  Lys Pro Val
```

```
         1010                1015                1020

Ala Ser Glu Glu Val Ile Arg Asn Tyr Phe Ser Tyr Leu Asp Asn
    1025                1030                1035

Ser Tyr Ile Arg Asp Ser Ser Lys Ser Leu Leu Glu Tyr Asn Lys
    1040                1045                1050

Asn Tyr Gln Leu Tyr Asn Tyr Val Phe Pro Glu Thr Ser Leu Tyr
    1055                1060                1065

Glu Val Asn Asp Asn Asn Lys Ser Tyr Leu Ser Leu Lys Asn Thr
    1070                1075                1080

Asp Gly Ile Asn Ile Pro Ser Val Lys Phe Lys Leu Ile Asn Ile
    1085                1090                1095

Asp Glu Ser Lys Gly Tyr Val Gln Lys Trp Asp Glu Cys Ile Ile
    1100                1105                1110

Cys Val Ser Asp Gly Thr Glu Lys Tyr Leu Asp Ile Ser Pro Glu
    1115                1120                1125

Asn Asn Arg Ile Gln Leu Val Ser Ser Lys Asp Asn Ala Lys Lys
    1130                1135                1140

Ile Thr Val Asn Thr Asp Leu Phe Arg Pro Asp Cys Ile Thr Phe
    1145                1150                1155

Ser Tyr Asn Asp Lys Tyr Phe Ser Leu Ser Leu Arg Asp Gly Asp
    1160                1165                1170

Tyr Asn Trp Met Ile Cys Asn Asp Asn Lys Val Pro Lys Gly
    1175                1180                1185

Ala His Leu Trp Ile Leu Lys Ser
    1190                1195

<210> SEQ ID NO 29
<211> LENGTH: 1162
<212> TYPE: PRT
<213> ORGANISM: C. botulinum

<400> SEQUENCE: 29

Met Lys Ile Asn Gly Asn Leu Asn Ile Asp Ser Pro Val Asp Asn
1               5                   10                  15

Asn Val Ala Ile Val Arg Ser Arg Asn Gln Met Phe Phe Lys Ala Phe
                20                  25                  30

Gln Val Ala Pro Asn Ile Trp Ile Val Pro Glu Arg Tyr Tyr Gly Glu
                35                  40                  45

Ser Leu Lys Ile Asn Glu Asp Gln Lys Phe Asp Gly Gly Ile Tyr Asp
50                  55                  60

Ser Asn Phe Leu Ser Thr Asn Glu Lys Asp Asp Phe Leu Gln Ala
65                  70                  75                  80

Thr Ile Lys Leu Leu Gln Arg Ile Asn Asn Asn Val Val Gly Ala Lys
                85                  90                  95

Leu Leu Ser Leu Ile Ser Thr Ala Ile Pro Phe Pro Tyr Glu Asn Asn
                100                 105                 110

Thr Glu Asp Tyr Arg Gln Thr Asn Tyr Leu Ser Ser Lys Asn Asn Glu
            115                 120                 125

His Tyr Tyr Thr Ala Asn Leu Val Ile Phe Gly Pro Gly Ser Asn Ile
    130                 135                 140

Ile Lys Asn Asn Val Ile Tyr Tyr Lys Lys Glu Tyr Ala Glu Ser Gly
145                 150                 155                 160

Met Gly Thr Met Leu Glu Ile Trp Phe Gln Pro Phe Leu Thr His Lys
                165                 170                 175
```

```
Tyr Asp Glu Phe Tyr Val Asp Pro Ala Leu Glu Leu Ile Lys Cys Leu
            180                 185                 190

Ile Lys Ser Leu Tyr Tyr Leu Tyr Gly Ile Lys Pro Asn Asp Asn Leu
        195                 200                 205

Asn Ile Pro Tyr Arg Leu Arg Asn Glu Phe Asn Ser Leu Glu Tyr Ser
    210                 215                 220

Glu Leu Asn Met Ile Asp Phe Leu Ile Ser Gly Ile Asp Tyr Lys
225                 230                 235                 240

Leu Leu Asn Thr Asn Pro Tyr Trp Phe Ile Asp Lys Tyr Phe Ile Asp
                245                 250                 255

Thr Ser Lys Asn Phe Glu Lys Tyr Lys Asn Asp Tyr Glu Ile Lys Ile
            260                 265                 270

Lys Asn Asn Asn Tyr Ile Ala Asn Ser Ile Lys Leu Tyr Leu Glu Gln
        275                 280                 285

Lys Phe Lys Ile Asn Val Lys Asp Ile Trp Glu Leu Asn Leu Ser Tyr
    290                 295                 300

Phe Ser Lys Glu Phe Gln Ile Met Met Pro Glu Arg Tyr Asn Asn Ala
305                 310                 315                 320

Leu Asn His Tyr Tyr Arg Lys Glu Phe Tyr Val Ile Asp Tyr Phe Lys
                325                 330                 335

Asn Tyr Asn Ile Asn Gly Phe Lys Asn Gly Gln Ile Lys Thr Lys Leu
            340                 345                 350

Pro Leu Ser Lys Tyr Asn Lys Glu Ile Ile Asn Lys Pro Glu Leu Ile
        355                 360                 365

Val Asn Leu Ile Asn Gln Asn Asn Thr Val Leu Met Lys Ser Asn Ile
    370                 375                 380

Tyr Gly Asp Gly Leu Lys Gly Thr Val Asp Asn Phe Tyr Ser Asn Tyr
385                 390                 395                 400

Ile Ile Pro Tyr Asn Leu Asn Tyr Glu His Ser Ile Asn Tyr Phe Tyr
                405                 410                 415

Leu Asp Asn Val Asn Ile Glu Glu Ile Glu Lys Ile Pro Pro Ile Asn
            420                 425                 430

Asp Glu Asp Ile Tyr Pro Tyr Arg Lys Asn Ala Asp Thr Phe Ile Pro
        435                 440                 445

Val Tyr Asn Ile Thr Lys Ala Lys Glu Ile Asn Thr Thr Thr Pro Leu
    450                 455                 460

Pro Val Asn Tyr Leu Gln Ala Gln Met Ile Asp Ser Asn Asp Ile Asn
465                 470                 475                 480

Leu Ser Ser Asp Phe Leu Lys Val Ile Ser Ser Lys Gly Ser Leu Val
                485                 490                 495

Tyr Ser Phe Leu Asn Asn Thr Met Asp Tyr Leu Glu Phe Ile Lys Tyr
            500                 505                 510

Asp Lys Pro Ile Asp Thr Asp Lys Lys Tyr Tyr Lys Trp Leu Lys Ala
        515                 520                 525

Ile Phe Arg Asn Tyr Ser Leu Asp Ile Thr Glu Thr Gln Glu Ile Ser
    530                 535                 540

Asn Gln Phe Gly Asp Thr Lys Ile Ile Pro Trp Ile Gly Arg Ala Leu
545                 550                 555                 560

Asn Ile Leu Asn Thr Asn Asn Ser Phe Val Glu Glu Phe Lys Asn Leu
                565                 570                 575

Gly Pro Ile Ser Leu Ile Asn Lys Lys Glu Asn Ile Thr Ile Pro Lys
            580                 585                 590

Ile Lys Ile Asp Glu Ile Pro Ser Ser Met Leu Asn Phe Ser Phe Lys
```

-continued

```
            595                 600                 605
Asp Leu Ser Glu Asn Leu Phe Asn Ile Tyr Cys Lys Asn Asn Phe Tyr
610                 615                 620

Leu Lys Lys Ile Tyr Tyr Asn Phe Leu Asp Gln Trp Thr Gln Tyr
625                 630                 635                 640

Tyr Ser Gln Tyr Phe Asp Leu Ile Cys Met Ala Ser Lys Ser Val Leu
                645                 650                 655

Ala Gln Glu Lys Leu Ile Lys Lys Leu Ile Gln Lys Gln Leu Arg Tyr
            660                 665                 670

Leu Met Glu Asn Ser Asn Ile Ser Ser Thr Asn Leu Ile Leu Ile Asn
            675                 680                 685

Leu Thr Thr Thr Asn Thr Leu Arg Asp Ile Ser Asn Gln Ser Gln Ile
            690                 695                 700

Ala Ile Asn Asn Ile Asp Lys Phe Phe Asn Asn Ala Ala Met Cys Val
705                 710                 715                 720

Phe Glu Asn Asn Ile Tyr Pro Lys Phe Thr Ser Phe Met Glu Gln Cys
                725                 730                 735

Ile Lys Asn Ile Asn Lys Ser Thr Lys Glu Phe Ile Leu Lys Cys Thr
            740                 745                 750

Asn Ile Asn Glu Thr Glu Lys Ser His Leu Ile Met Gln Asn Ser Phe
            755                 760                 765

Ser Asn Leu Asp Phe Asp Phe Leu Asp Ile Gln Asn Met Lys Asn Leu
770                 775                 780

Phe Asn Leu Tyr Thr Glu Leu Leu Ile Lys Glu Gln Thr Ser Pro Tyr
785                 790                 795                 800

Glu Leu Ser Leu Tyr Ala Phe Gln Glu Gln Asp Asn Asn Val Ile Gly
                805                 810                 815

Asp Thr Ser Gly Lys Asn Thr Leu Val Glu Tyr Pro Lys Asp Ile Gly
            820                 825                 830

Leu Val Tyr Gly Ile Asn Asn Asn Ala Ile His Leu Thr Gly Ala Asn
            835                 840                 845

Gln Asn Ile Lys Phe Thr Asn Asp Tyr Phe Glu Asn Gly Leu Thr Asn
            850                 855                 860

Asn Phe Ser Ile Tyr Phe Trp Leu Arg Asn Leu Lys Gln Asn Thr Ile
865                 870                 875                 880

Lys Ser Lys Leu Ile Gly Ser Lys Glu Asp Asn Cys Gly Trp Glu Ile
                885                 890                 895

Tyr Phe Glu Asn Asp Gly Leu Val Phe Asn Ile Ile Asp Ser Asn Gly
            900                 905                 910

Asn Glu Lys Asn Ile Tyr Leu Ser Asn Ile Ser Asn Lys Ser Trp His
            915                 920                 925

Tyr Ile Val Ile Ser Ile Asn Arg Leu Lys Asp Gln Leu Leu Ile Phe
            930                 935                 940

Ile Asp Asn Ile Leu Val Ala Asn Glu Asp Ile Lys Glu Ile Leu Asn
945                 950                 955                 960

Ile Tyr Ser Ser Asp Ile Ile Ser Leu Leu Ser Asp Asn Asn Asn Val
                965                 970                 975

Tyr Ile Glu Gly Leu Ser Val Leu Asn Lys Thr Ile Asn Ser Asn Glu
            980                 985                 990

Ile Leu Thr Asp Tyr Phe Ser Asp Leu Asn Asn Ser Tyr Ile Arg Asn
            995                 1000                1005

Phe Asp Glu Glu Ile Leu Gln Tyr Asn Arg Thr Tyr Glu Leu Phe
    1010                1015                1020
```

-continued

```
Asn Tyr Val Phe Pro Glu Ile Ala Ile Asn Lys Ile Glu Gln Asn
    1025                1030                1035

Asn Asn Ile Tyr Leu Ser Ile Asn Asn Glu Asn Asn Leu Asn Phe
    1040                1045                1050

Lys Pro Leu Lys Phe Lys Leu Leu Asn Thr Asn Pro Asn Lys Gln
    1055                1060                1065

Tyr Val Gln Lys Trp Asp Glu Val Ile Phe Ser Val Leu Asp Gly
    1070                1075                1080

Thr Glu Lys Tyr Leu Asp Ile Ser Thr Thr Asn Asn Arg Ile Gln
    1085                1090                1095

Leu Val Asp Asn Lys Asn Asn Ala Gln Ile Phe Ile Ile Asn Asn
    1100                1105                1110

Asp Ile Phe Ile Ser Asn Cys Leu Thr Leu Thr Tyr Asn Asn Val
    1115                1120                1125

Asn Val Tyr Leu Ser Ile Lys Asn Gln Asp Tyr Asn Trp Val Ile
    1130                1135                1140

Cys Asp Leu Asn His Asp Ile Pro Lys Lys Ser Tyr Leu Trp Ile
    1145                1150                1155

Leu Lys Asn Ile
    1160

<210> SEQ ID NO 30
<211> LENGTH: 1159
<212> TYPE: PRT
<213> ORGANISM: C. botulinum

<400> SEQUENCE: 30

Met Lys Ile Asn Asn Phe Asn Ile Asp Ser Leu Ile Asp Asn Arg
1                   5                   10                  15

Asp Val Ala Ile Val Arg Gly Arg Lys Thr Asp Thr Phe Phe Lys Val
                    20                  25                  30

Phe Gln Val Ala Pro Asn Ile Trp Ile Ala Pro Glu Arg Tyr Tyr Gly
            35                  40                  45

Glu Ser Leu Asn Ile Asn Glu Asp Gln Lys Ser Asp Gly Gly Ile Tyr
    50                  55                  60

Asp Ser Asn Phe Leu Ser Thr Asn Asp Glu Lys Asp Glu Phe Leu Gln
65                  70                  75                  80

Ala Thr Val Lys Ile Leu Gln Arg Ile Asn Asn Asn Val Ile Gly Ala
                    85                  90                  95

Lys Leu Leu Ser Leu Ile Ser Thr Ala Ile Pro Phe Pro Tyr Glu Tyr
                100                 105                 110

Lys Pro Gly Asp Tyr Arg Gln Thr Asn Tyr Leu Val Ser Lys Asp Asn
            115                 120                 125

Gln His Tyr Tyr Thr Ala Asn Leu Val Ile Phe Gly Pro Gly Thr Asn
    130                 135                 140

Ile Val Glu Asn Asn Ala Ile Tyr Tyr Lys Lys Glu Asp Ser Glu Asn
145                 150                 155                 160

Gly Met Gly Thr Met Ser Glu Ile Trp Phe Gln Pro Phe Leu Thr Tyr
                    165                 170                 175

Lys Tyr Gly Gln Phe Tyr Val Asp Pro Ala Leu Glu Leu Ile Lys Cys
                180                 185                 190

Leu Ile Lys Ser Leu Tyr Tyr Leu Tyr Gly Ile Lys Pro Ser Asp Asp
            195                 200                 205

Leu Ser Ile Pro Tyr Arg Leu Arg Ser Glu Leu Asn Ser Phe Glu Tyr
```

-continued

```
            210                 215                 220
Ser Glu Leu Asp Met Ile Asp Phe Leu Ile Ser Gly Gly Thr Glu Tyr
225                 230                 235                 240

Lys Leu Leu Asp Thr Asn Pro Tyr Trp Phe Thr Asp Asn Tyr Phe Ile
                245                 250                 255

Asp Ala Pro Lys Asn Phe Glu Lys Tyr Lys Asn Asp Tyr Glu Thr Lys
                260                 265                 270

Ile Lys Asn Asn Asn Asp Ile Ala Asn Ser Ile Lys Leu Tyr Leu Glu
                275                 280                 285

Gln Lys Phe Lys Thr Asn Ala Gln Asp Ile Trp Glu Leu Asn Leu Ser
290                 295                 300

Tyr Phe Ser Thr Glu Phe Glu Ile Met Met Pro Glu Ile Phe Asn Asn
305                 310                 315                 320

Ala Leu Asn His Tyr Tyr Arg Lys Glu Tyr Tyr Val Ile Asp Tyr Phe
                325                 330                 335

Lys Asn Tyr Asn Ile Asn Gly Phe Ile Asn Gly Gln Ile Lys Thr Ile
                340                 345                 350

Leu Pro Leu Ser Lys Tyr Asn Lys Asn Ile Ile Asn Lys Pro Glu Leu
                355                 360                 365

Val Val Asn Leu Ile Asn Glu Asn Asn Thr Val Leu Met Lys Ser Asn
370                 375                 380

Val Tyr Gly Asp Gly Leu Lys Gly Thr Met Asp Asn Phe Tyr Ala Ala
385                 390                 395                 400

Tyr Lys Ile Pro Tyr Asn Ile Gly Asp Glu Tyr His Ile Asn Tyr Ser
                405                 410                 415

Tyr Leu Asn Asn Val Asn Val Glu Glu Ile Asn Asn Ile Pro Pro Ile
                420                 425                 430

Asn Asp Ala Asp Ile Tyr Pro Tyr Arg Lys Asn Ser Asp Pro Phe Ile
                435                 440                 445

Pro Val Tyr Asn Ile Thr Glu Thr Lys Glu Ile Asn Thr Thr Thr Pro
450                 455                 460

Leu Ser Val Asn Tyr Leu Gln Ala Gln Val Thr Asn Ser Asn Asp Ile
465                 470                 475                 480

Ser Leu Ser Ser Asp Phe Ser Lys Val Ile Ser Ser Lys Asp Arg Ser
                485                 490                 495

Leu Val Tyr Ser Phe Leu Asp Asn Thr Ile Asp Tyr Leu Asp Ser Ile
                500                 505                 510

Lys Tyr Asp Glu Pro Ile Asp Thr Asp Lys Lys Tyr Tyr Leu Trp Leu
                515                 520                 525

Lys Glu Ile Phe Arg Asn Tyr Ser Phe Asp Met Thr Glu Thr Gln Glu
530                 535                 540

Val Asn Thr Pro Cys Gly Ile Asn Lys Val Val Pro Trp Leu Gly Lys
545                 550                 555                 560

Ala Leu Asn Ile Leu Asn Thr Gly Asn Ser Phe Ile Glu Glu Phe Lys
                565                 570                 575

Ser Leu Gly Pro Ile Ser Leu Ile Asn Lys Lys Glu Asn Ile Thr Met
                580                 585                 590

Pro Lys Ile Glu Ile Asp Glu Ile Pro Asn Ser Met Leu Asn Leu Ser
                595                 600                 605

Phe Lys Asp Leu Ser Glu Asn Leu Phe Asn Arg Phe Ser Lys Asn Asn
                610                 615                 620

Ser Tyr Phe Glu Lys Ile Tyr Tyr Asp Phe Leu Asp Gln Trp Trp Thr
625                 630                 635                 640
```

-continued

```
Gln Tyr Tyr Ser Gln Tyr Phe Asp Leu Ile Cys Met Ala Lys Lys Ser
                645                 650                 655

Ile Leu Ala Gln Glu Thr Leu Ile Lys Lys Ile Ile Gln Lys Lys Leu
                660                 665                 670

Ser Tyr Leu Ile Gly Asn Ser Asn Ile Ser Ser Asp Asn Leu Ala Leu
                675                 680                 685

Met Asn Leu Thr Thr Thr Asn Thr Leu Arg Asp Ile Ser Asn Glu Ser
                690                 695                 700

Gln Ile Ala Met Asn Asn Val Asp Ser Phe Leu Asn Ser Ala Ala Ile
705                 710                 715                 720

Cys Val Phe Glu Gly Asn Ile Tyr Ser Lys Phe Ile Ser Phe Met Glu
                725                 730                 735

Gln Cys Ile Asn Asn Ile Asn Lys Asn Thr Arg Glu Phe Ile Gln Lys
                740                 745                 750

Cys Thr Asn Ile Thr Glu Asn Glu Lys Leu Gln Leu Ile Asn Gln Asn
                755                 760                 765

Ile Phe Ser Ser Leu Asp Phe Asp Phe Leu Asn Ile Glu Asn Leu Lys
                770                 775                 780

Ser Leu Phe Ser Ser Glu Thr Ala Leu Leu Ile Lys Glu Glu Thr Ser
785                 790                 795                 800

Pro Tyr Glu Leu Val Leu Tyr Ala Phe Gln Pro Asp Asn Asn Ala
                805                 810                 815

Ile Gly Asp Ala Ser Ala Lys Asn Thr Ser Ile Glu Tyr Ser Lys Asp
                820                 825                 830

Ile Asp Leu Val Tyr Gly Ile Asn Ser Asp Ala Leu Tyr Leu Asn Gly
                835                 840                 845

Ser Asn Gln Ser Ile Ser Phe Ser Asn Asp Phe Phe Glu Asn Gly Leu
                850                 855                 860

Thr Asn Ser Phe Ser Ile Tyr Phe Trp Leu Arg Asn Leu Gly Lys Asp
865                 870                 875                 880

Thr Ile Lys Tyr Lys Leu Ile Gly Ser Lys Glu Asp Asn Cys Gly Trp
                885                 890                 895

Glu Ile Tyr Phe Gln Asp Thr Gly Leu Val Phe Asn Met Ile Asp Ser
                900                 905                 910

Asn Gly Asn Glu Lys Asn Ile Tyr Leu Ser Asp Val Ser Asn Asn Ser
                915                 920                 925

Trp His Tyr Ile Thr Ile Ser Val Asp Arg Leu Lys Glu Gln Leu Leu
                930                 935                 940

Ile Phe Ile Asp Asp Asn Leu Val Ala Asn Glu Ser Ile Lys Glu Ile
945                 950                 955                 960

Leu Asn Ile Tyr Ser Ser Asn Ile Ile Ser Leu Leu Ser Glu Asn Lys
                965                 970                 975

Pro Ser Tyr Ile Glu Gly Leu Thr Ile Leu Asn Lys Pro Thr Thr Ser
                980                 985                 990

Gln Glu Val Leu Asn Asn Tyr Phe  Lys Val Leu Asn Asn  Ser Tyr Ile
                995                 1000                1005

Arg Asp  Ser Asn Glu Glu Arg  Leu Glu Tyr His Lys  Thr Tyr Gln
    1010                1015                1020

Leu Asp  Asn Tyr Val Phe Ser  Asp Lys Pro Ile Cys  Glu Val Lys
    1025                1030                1035

Gln Asn  Asn Asn Ile Tyr Leu  Thr Ile Asn Asn Thr  Asn Asn Leu
    1040                1045                1050
```

Asn Leu Gln Pro Ser Lys Phe Lys Leu Leu Ser Ile Asn Ser Asn
    1055                1060                1065

Lys Gln Tyr Val Gln Lys Phe Asp Glu Val Ile Ile Ser Ile Leu
    1070                1075                1080

Gly Asn Met Glu Lys Tyr Ile Asp Ile Ser Glu Asp Asn Arg Leu
    1085                1090                1095

Gln Leu Ile Asp Asn Lys Asn Gly Ala Lys Lys Met Ile Ile Ser
    1100                1105                1110

Asn Asp Met Phe Ile Ser Asn Cys Leu Thr Leu Ser Cys Gly Gly
    1115                1120                1125

Lys Tyr Ile Cys Leu Ser Met Lys Asp Glu Asn His Asn Trp Met
    1130                1135                1140

Ile Cys Asn Asn Asp Met Ser Lys Tyr Leu Tyr Leu Trp Ser Phe
    1145                1150                1155

Lys

<210> SEQ ID NO 31
<211> LENGTH: 1165
<212> TYPE: PRT
<213> ORGANISM: C. botulinum

<400> SEQUENCE: 31

Met Lys Ile Asn Asp Asp Leu Asn Ile Asn Ser Pro Val Asp Asn Lys
1               5                   10                  15

Asn Val Val Ile Val Arg Ala Arg Lys Thr Asn Ile Phe Phe Lys Ala
                20                  25                  30

Phe Gln Val Ala Pro Asn Ile Trp Val Ala Pro Glu Arg Tyr Tyr Gly
            35                  40                  45

Glu Pro Leu Asn Ile Ser Asp Gln Glu Lys Ser Asp Gly Gly Ile Tyr
50                  55                  60

Asp Glu Asn Phe Leu Lys Glu Asn Ser Glu Lys Glu Phe Leu Gln
65                  70                  75                  80

Ala Ile Ile Leu Leu Leu Lys Arg Ile Asn Asn Asn Ile Ile Gly Gln
                85                  90                  95

Lys Leu Leu Ser Leu Met Cys Thr Ser Ile Pro Phe Leu His Glu Tyr
            100                 105                 110

Lys Gln Gly Asp Tyr Arg Gln Ser Asn Tyr Leu Gly Ser Lys Asn Ser
        115                 120                 125

Glu Tyr Leu Tyr Ser Ala Asn Ile Val Ile Phe Gly Pro Gly Ser Asn
    130                 135                 140

Ile Val Lys Asn Asn Thr Ile Tyr Tyr Lys Lys Asn Phe Ala Glu Asn
145                 150                 155                 160

Gly Met Gly Thr Met Ala Glu Ile Leu Phe Gln Pro Phe Leu Thr Tyr
                165                 170                 175

Lys Tyr Asn Gln Phe Tyr Ala Asp Pro Ala Leu Glu Leu Ile Lys Cys
            180                 185                 190

Leu Ile Lys Ala Ile Tyr Phe Leu Tyr Gly Ile Lys Pro Asn Asp Asn
        195                 200                 205

Leu Asn Ile Pro Tyr Arg Leu Arg Asn Glu Phe Ser Asn Val Glu Tyr
    210                 215                 220

Ser Glu Leu Asn Ile Ile Asp Phe Leu Ile Ser Gly Gly Ile Asp Tyr
225                 230                 235                 240

Lys Phe Ile Asn Thr Asn Pro Tyr Trp Phe Ile Asp Asn Tyr Phe Ile
                245                 250                 255

```
Asp Val Pro Lys Val Phe Glu Lys His Lys Asn Asp Tyr Glu Ile Asn
            260                 265                 270

Ile Lys Asn Asn Ser Glu Ile Gly Thr Ser Ile Lys Leu Tyr Leu Glu
        275                 280                 285

Gln Lys Phe Lys Thr Asn Val Gln Asp Ile Trp Glu Leu Asn Leu Ser
    290                 295                 300

Tyr Phe Ser Lys Glu Phe Gln Ile Met Met Pro Glu Lys His Asn Asn
305                 310                 315                 320

Ala Leu Lys His Tyr Tyr Arg Lys Glu Tyr Lys Ile Asn Tyr Ser
            325                 330                 335

Lys Gln Tyr Asp Ile Asn Gly Phe Val Asn Gly Gln Ile Ala Thr Lys
            340                 345                 350

Leu Leu Leu Ser Glu Lys Asn Gln Tyr Ile Ile Asn Lys Pro Gln Leu
            355                 360                 365

Ile Ile Asn Leu Ile Asn Lys Ser Asn Asn Ser Leu Leu Met Lys Ser
        370                 375                 380

Asn Ile Tyr Gly Asp Gly Leu Asn Gly Thr Thr Asp Asn Phe Tyr Arg
385                 390                 395                 400

Asn Tyr Lys Ile Pro Asp Asn Ile Ala Tyr Gln Tyr His Pro Asn Asn
                405                 410                 415

Thr Tyr Leu Asp Asn Val Asn Ile Glu Glu Ile Asn Asn Ile Pro Gln
            420                 425                 430

Ile Thr Asp Ala Asp Ile Tyr Pro Tyr Thr Asn Asn Cys Asp Thr Phe
        435                 440                 445

Ile Pro Ile Tyr Asn Ile Thr Gln Ser Arg Glu Ile Asn Thr Thr Val
    450                 455                 460

Pro Tyr Ser Ile Asn Tyr Leu Gln Ser Gln Ile Met Asn Ser Asp Asp
465                 470                 475                 480

Ile Thr Leu Ser Ser Asp Phe Trp Glu Val Val Cys Ser Asn Asp Lys
            485                 490                 495

Ser Leu Val Tyr Ser Tyr Leu Asp Asn Val Ile Asn Tyr Leu Asp Ser
            500                 505                 510

Ile Lys Asn Asn Thr Pro Ile Asn Thr Asp Lys Lys Tyr Tyr Leu Trp
        515                 520                 525

Leu Lys Glu Ile Phe Arg Asn Tyr Ser Phe Asp Ile Thr Ala Thr Glu
    530                 535                 540

Glu Ile Thr Thr Glu Cys Gly Ile Asn Lys Ile Val Ser Trp Phe Gly
545                 550                 555                 560

Lys Ala Phe Asn Ile Leu Asn Thr Asp Asn Ser Phe Lys Ile Glu Phe
                565                 570                 575

Gln Asn Ser Gly Ala Ile Ala Leu Ile Asn Lys Lys Asp Asn Ile Ile
            580                 585                 590

Ile Pro Lys Ile Glu Ile Asp Glu Met Pro Asn Ser Met Leu Asn Leu
        595                 600                 605

Ser Phe Glu Asp Leu Asn Glu Gln Leu Tyr Ser Ile Tyr Ser Lys Asn
    610                 615                 620

Ile Thr Tyr Phe Lys Lys Ile Tyr Tyr Asn Phe Leu Asp Gln Trp Trp
625                 630                 635                 640

Thr Glu Tyr Tyr Ser Gln Tyr Phe Asp Leu Ile Cys Met Ala Lys Lys
                645                 650                 655

Ser Ile Leu Ala Gln Glu Asn Leu Ile Lys Lys Ile Gln Lys Lys
            660                 665                 670

Ile Ser Tyr Leu Ile Gly Ala Ser Asn Ile Pro Asp Asp Ile Leu Ala
```

-continued

```
            675                 680                 685
Val Met Arg Leu Thr Thr Thr Asn Thr Leu Arg Asp Ile Ser Val Glu
690                     695                 700
Ser Gln Ile Ala Met Asn Asn Leu Asn Asn Phe Leu Asn Lys Ala Ala
705                     710                 715                 720
Met Cys Val Phe Gln Ser Asn Ile Tyr Pro Lys Phe Ile Ser Phe Met
                    725                 730                 735
Glu Gln Cys Ile Lys His Ile Asn Lys Ser Thr Lys Glu Phe Ile Gln
                740                 745                 750
Lys Cys Thr Asn Ile Asn Glu Thr Glu Lys Leu Gln Leu Ile Met Gln
            755                 760                 765
Asn Ser Phe Ser Asn Leu Asp Phe Asp Phe Leu Asp Ile Gln Asn Met
770                 775                 780
Lys Asn Leu Phe Asn Ser Tyr Thr Glu Leu Leu Ile Lys Glu Gln Thr
785                 790                 795                 800
Ser Pro Tyr Glu Leu Ser Leu Tyr Ala Phe Glu Glu Gln Asp Asn Asn
                805                 810                 815
Val Ile Gly Asp Ala Ser Gly Lys Asn Thr Leu Val Glu Tyr Pro Lys
                820                 825                 830
Gly Ile Glu Leu Val Tyr Gly Ile Asn Asn Ser Ala Leu Tyr Leu Asn
            835                 840                 845
Gly Ser Asn Gln Ser Ile Ile Phe Thr Asn Asp Tyr Phe Glu Asn Gly
            850                 855                 860
Leu Thr Asn Ser Phe Ser Ile Tyr Phe Trp Leu Arg Asn Leu Gly Gln
865                 870                 875                 880
Asp Thr Ile Lys Ser Lys Leu Ile Gly Ser Lys Glu Tyr Asn Cys Gly
                885                 890                 895
Trp Glu Ile Tyr Phe Gln Ile Gly His Val Phe Asn Met Ile Asp
                900                 905                 910
Ser Asn Gly Asn Glu Lys Asn Ile Tyr Leu Ser Asp Val Ser Asn Asn
            915                 920                 925
Ser Trp His Tyr Ile Thr Ile Ser Val Asp Arg Leu Lys Glu Gln Leu
            930                 935                 940
Leu Ile Phe Ile Asp Asp Asn Leu Val Val Asn Glu Ser Ile Lys Asp
945                 950                 955                 960
Ile Leu Asn Ile Tyr Ser Ser Asn Ile Ile Ser Leu Ser Asp Asn
                    965                 970                 975
Lys Ala Ser Tyr Ile Glu Gly Leu Thr Ile Leu Asn Lys Pro Thr Thr
                980                 985                 990
Gly Glu Glu Val Leu Arg Asn Tyr  Phe Lys Asn Leu Asn  Asn Ser Tyr
            995                 1000                1005
Val Arg Asp Ser Asn Asp Glu  Arg Leu Glu Tyr Asn  Lys Thr Tyr
    1010                1015                1020
Gln Leu Tyr Asp Tyr Val Phe  Pro Asp Asn Pro Ile  Cys Glu Val
    1025                1030                1035
Lys Gln Asp Asn Asn Ile Tyr  Leu Thr Ile Asn Asn  Ile Asn Asn
    1040                1045                1050
Leu Asn Met Lys Pro Cys Lys  Phe Lys Leu Leu Ser  Ile Asn Ser
    1055                1060                1065
Asn Lys Gln Tyr Val Gln Lys  Trp Asp Glu Val Ile  Ile Ser Val
    1070                1075                1080
Leu Tyr Asp Thr Glu Lys Tyr  Val Cys Ile Ser Asn  Glu Asn Asn
    1085                1090                1095
```

```
Arg Val Lys Ile Ile Asp Asn Lys Ile Met Gln Val Lys Phe Ile
    1100                1105                1110

Ile Ser Asn Asp Ile Phe Ile Ser Asn Cys Leu Thr His Ala His
    1115                1120                1125

Asn Asn Lys Tyr Ile Cys Leu Ser Met Lys Asp Glu Asn Tyr Asn
    1130                1135                1140

Trp Met Ile Cys Asn Asn Glu Ser Asn Ile Pro Lys Lys Ala Tyr
    1145                1150                1155

Leu Trp Ile Leu Lys Glu Val
    1160                1165

<210> SEQ ID NO 32
<211> LENGTH: 1198
<212> TYPE: PRT
<213> ORGANISM: C. botulinum

<400> SEQUENCE: 32

Met Lys Ile Asn Ser Asn Leu Thr Ile Asn Ser Pro Ile Asp Asn Lys
1               5                   10                  15

Asn Val Val Ile Val Arg Ala Arg Glu Thr Ser Lys Phe Phe Lys Ala
                20                  25                  30

Phe Lys Val Ala Pro Asn Ile Trp Val Ala Pro Glu Arg Tyr Tyr Gly
            35                  40                  45

Glu Ser Leu Ser Ile Glu Ser Lys Lys Val Asn Gly Gly Val Tyr
        50                  55                  60

Asp Ser Asn Phe Leu Ser Gln Asn Asn Glu Lys Asp Lys Phe Leu Gln
65                  70                  75                  80

Ala Ile Ile Thr Leu Leu Lys Arg Ile Asn Ser Asn Ile Ala Gly Glu
                85                  90                  95

Lys Leu Leu Ser Leu Val Ser Thr Ala Ile Pro Phe Pro Tyr Gly Tyr
            100                 105                 110

Ile Gly Gly Gly Tyr Tyr Cys Pro Asn Ile Val Thr Phe Gly Ser Thr
        115                 120                 125

Ile Lys Tyr Asn Lys Lys Ile Asn Ser Leu Ile Ser Thr Thr Ile Pro
    130                 135                 140

Phe Pro Tyr Gly Gly Tyr Arg Glu Thr Asn Tyr Leu Ser Ser Lys Asp
145                 150                 155                 160

Thr Glu Asn Phe Tyr Ala Ala Asn Ile Val Ile Phe Gly Pro Gly Ala
                165                 170                 175

Asn Ile Val Glu Asn Asn Thr Val Phe Tyr Lys Lys Glu Asp Ala Glu
            180                 185                 190

Asn Gly Met Gly Thr Met Ala Glu Ile Cys Phe Gln Pro Phe Leu Thr
        195                 200                 205

Tyr Lys Tyr Asp Gln Phe Tyr Val Asp Pro Ala Leu Glu Leu Met Glu
    210                 215                 220

Cys Leu Ile Lys Ser Leu Tyr Phe Leu Tyr Gly Ile Lys Pro Asn Asn
225                 230                 235                 240

Asn Leu Thr Val Pro Tyr Arg Leu Arg Asn Glu Leu Ser Asn Ile Glu
                245                 250                 255

Phe Ser Gln Leu Ser Ile Val Asp Leu Leu Ile Ser Gly Gly Ile Asp
            260                 265                 270

Ser Lys Phe Ile Asn Thr Asp Pro Tyr Trp Phe Ile Asp Ser Tyr Phe
        275                 280                 285

Ser Asn Ala Lys Thr Thr Phe Glu Glu His Lys Ser Ile Tyr Glu Thr
```

-continued

```
            290                 295                 300
Glu Ile Lys Gly Asn Asn Ala Ile Gly Asn Asp Ile Lys Leu Arg Leu
305                 310                 315                 320

Lys Gln Lys Phe Gln Thr Thr Val His Asp Ile Trp Gln Leu Asn Leu
                325                 330                 335

Asp Tyr Phe Ser Lys Glu Phe Gln Ile Met Met Pro Tyr Arg Phe Asn
                340                 345                 350

Asn Ala Leu Lys Tyr Tyr Tyr Arg Lys Glu Tyr Tyr Lys Ile Asp Tyr
                355                 360                 365

Pro Glu Lys Tyr Ser Ile Ala Gly Phe Val Asp Gly Gln Leu Asn Thr
370                 375                 380

Gln Leu Ser Leu Ser Asp Lys Asn Gln Tyr Ile Ile Asn Lys Pro Glu
385                 390                 395                 400

Leu Ile Val Asn Leu Ile Ser Glu Asn Asn Ile Ser Leu Met Arg Ser
                405                 410                 415

Asn Ile Tyr Gly Asp Gly Leu Lys Tyr Thr Thr Asp Asn Phe Tyr Ser
                420                 425                 430

Thr Tyr Lys Ile Pro Tyr Asn Arg Ala Tyr Glu Tyr His Phe Asn Asn
                435                 440                 445

Ser Ser Thr Ser Ser Leu Glu Asn Val Asn Val Glu Glu Ile Ser Asn
                450                 455                 460

Ile Pro Glu Ile Ile Asp Ile Asn Pro Tyr Arg Glu Asn Ser Asp Ile
465                 470                 475                 480

Phe Ser Pro Val Glu Asn Ile Ile Glu Thr Lys Glu Val Asn Thr Lys
                485                 490                 495

Thr Pro Trp Pro Ile Asn Tyr Leu Gln Ala Gln Ile Pro Asn Asn Glu
                500                 505                 510

Glu Phe Thr Leu Ser Ser Asp Phe Ser Gln Val Val Ser Tyr Lys Thr
                515                 520                 525

Gln Ser Leu Val Tyr Ser Phe Leu Ser Asn Val Ile Ser Tyr Leu Asp
                530                 535                 540

Ser Val Lys Asp Thr Asn Pro Ile Asp Thr Asp Glu Lys Tyr Tyr Leu
545                 550                 555                 560

Trp Leu Arg Glu Ile Phe Arg Asn Tyr Ser Phe Asp Ile Thr Ala Ile
                565                 570                 575

Glu Glu Ile Asn Thr Ser Cys Gly Ile Asn Lys Val Val Ser Trp Phe
                580                 585                 590

Gly Lys Ala Leu Asn Ile Leu Asn Thr Ser Asn Ser Phe Val Lys Glu
                595                 600                 605

Phe Lys Asn Leu Gly Pro Ile Ser Leu Ile Asn Lys Lys Glu Asn Leu
                610                 615                 620

Ser Met Pro Ile Ile Glu Val Asn Glu Ile Pro Asn Asp Met Leu Gly
625                 630                 635                 640

Leu Ser Leu Lys Asp Leu Asn Glu Lys Leu Phe Asn Ile Tyr Leu Lys
                645                 650                 655

Asn Ile Leu Tyr Phe Lys Lys Val Tyr Phe Ser Phe Leu Asp Gln Trp
                660                 665                 670

Trp Thr Glu Tyr Tyr Ser Gln Tyr Phe Gly Leu Ile Cys Met Ala Lys
                675                 680                 685

Gln Ser Ile Leu Ala Gln Glu Asn Leu Ile Lys Lys Ile Val Gln Lys
                690                 695                 700

Lys Leu Ser Asp Leu Ser Lys Gln Ser Asn Ile Ser Asn Glu Lys Leu
705                 710                 715                 720
```

-continued

Asn Leu Met Asn Leu Thr Thr Glu Lys Thr Phe Ile Asp Leu Ser Asn
            725                 730                 735

Gln Ser Gln Ile Ala Met Asn Ile Asn Asn Phe Leu Asn Lys Ala
            740                 745                 750

Ala Ile Cys Val Phe Glu Ser Asn Ile Tyr Pro Lys Phe Ile Ser Phe
            755                 760                 765

Met Glu Gln Tyr Ile Asn Asn Ile Asn Ile Lys Thr Thr Ala Phe Ile
            770                 775                 780

Arg Lys Cys Thr Asn Ile Thr Glu Lys Glu Lys Leu Gln Leu Ile Asn
785                 790                 795                 800

Gln Asn Thr Phe Asn Asn Leu Asp Phe Glu Phe Phe Asp Ile Gln Thr
            805                 810                 815

Ile Glu Asn Leu Leu Thr Ser Glu Thr Asn Leu Ile Ile Lys Glu Lys
            820                 825                 830

Thr Ser Pro Tyr Asp Leu Leu Leu Phe Ser Leu Gln Glu Ala Asp Arg
            835                 840                 845

Lys Val Ile Lys Asp Ile Ser Gly Lys Asp Thr Leu Val Gln Tyr Ser
            850                 855                 860

Asp Thr Ile Asp Leu Ser Tyr Gly Val Asn Gly Asp Ala Leu Tyr Leu
865                 870                 875                 880

Lys Glu Pro Asn Gln Ser Val Asn Phe Ser Asn Asn Ile Phe Glu Asn
            885                 890                 895

Gly Leu Thr Asn Ser Phe Ser Ile Cys Phe Trp Leu Arg Asn Leu Gly
            900                 905                 910

Gln Asp Asn Leu Ser Ser Asn Leu Ile Gly Asn Ile Val Asn Asn Cys
            915                 920                 925

Gly Trp Gln Ile Tyr Phe Glu Asn Asn Gly Leu Val Phe Ser Met Val
            930                 935                 940

Asp Cys Asn Gly Asn Glu Lys Asn Ile Tyr Leu Ser Asp Val Leu Ser
945                 950                 955                 960

Lys Tyr Trp Tyr Tyr Ile Ser Val Ser Val Asp Arg Leu Arg Asn Lys
            965                 970                 975

Leu Leu Ile Phe Ile Asn Asp Lys Leu Ile Val Asn Glu Ser Ile Glu
            980                 985                 990

Gln Ile Leu Asn Ile Tyr Ser Ser Asn Ile Ile Ser Leu Val Asn Glu
            995                 1000                1005

Asn Asn Pro Ile Cys Ile Glu Glu Leu Ser Ile Leu Asn Lys Ala
    1010                1015                1020

Leu Thr Ser Glu Glu Val Leu Asn Ser Tyr Phe Thr Asn Leu Asn
    1025                1030                1035

Asn Ser Tyr Ile Arg Asp Ser Tyr Gly Ala Arg Leu Glu Tyr Asn
    1040                1045                1050

Lys Asn Tyr Glu Leu Tyr Asn Tyr Val Phe Pro Glu Asn Ser Leu
    1055                1060                1065

Tyr Glu Val Ile Glu Asn Asn Met Tyr Leu Ser Ile Lys Asn
    1070                1075                1080

Ile Lys Asn Thr Asn Ile Leu Gly Ala Lys Phe Lys Leu Ile Asn
    1085                1090                1095

Thr Asp Glu Ser Lys Gln Tyr Val Gln Lys Trp Asp Glu Val Ile
    1100                1105                1110

Ile Cys Val Leu Gly Asp Thr Glu Lys Tyr Ala Asp Ile Gln Ala
    1115                1120                1125

```
Gly Asn Asn Arg Ile Gln Leu Val Asn Ser Lys Asp Asn Ala Arg
        1130                1135                1140

Lys Ile Ile Val Asn Asn Ile Phe Arg Pro Asn Cys Val Leu
    1145                1150                1155

Phe Ser Tyr Asn Asn Lys Tyr Leu Ser Leu Ser Leu Arg Asn Arg
    1160                1165                1170

Asn Tyr Asn Trp Met Ile Cys Asn Asp Asn Ser Phe Ile Pro Lys
    1175                1180                1185

His Ala His Leu Trp Ile Leu Lys Lys Ile
        1190                1195

<210> SEQ ID NO 33
<211> LENGTH: 11
<212> TYPE: PRT
<213> ORGANISM: H. sapiens

<400> SEQUENCE: 33

Arg Pro Lys Pro Gln Gln Phe Phe Gly Leu Met
1               5                   10

<210> SEQ ID NO 34
<211> LENGTH: 12
<212> TYPE: PRT
<213> ORGANISM: H, sapiens

<400> SEQUENCE: 34

Arg Pro Lys Pro Gln Gln Phe Phe Gly Leu Met Gly
1               5                   10

<210> SEQ ID NO 35
<211> LENGTH: 13
<212> TYPE: PRT
<213> ORGANISM: H, sapiens

<400> SEQUENCE: 35

Arg Pro Lys Pro Gln Gln Phe Phe Gly Leu Met Gly Lys
1               5                   10

<210> SEQ ID NO 36
<211> LENGTH: 14
<212> TYPE: PRT
<213> ORGANISM: H, sapiens

<400> SEQUENCE: 36

Arg Pro Lys Pro Gln Gln Phe Phe Gly Leu Met Gly Lys Arg
1               5                   10

<210> SEQ ID NO 37
<211> LENGTH: 13
<212> TYPE: PRT
<213> ORGANISM: SV-40

<400> SEQUENCE: 37

Cys Gly Gly Gly Pro Lys Lys Lys Arg Lys Val Gly Gly
1               5                   10

<210> SEQ ID NO 38
<211> LENGTH: 14
<212> TYPE: PRT
<213> ORGANISM: HIV-1

<400> SEQUENCE: 38

Cys Gly Gly Arg Lys Lys Arg Arg Gln Arg Arg Arg Ala Pro
```

-continued

<210> SEQ ID NO 39
<211> LENGTH: 13
<212> TYPE: PRT
<213> ORGANISM: Adenovirus

<400> SEQUENCE: 39

Cys Gly Gly Phe Ser Thr Ser Leu Arg Ala Arg Lys Ala
1               5                   10

<210> SEQ ID NO 40
<211> LENGTH: 15
<212> TYPE: PRT
<213> ORGANISM: Artificial sequence
<220> FEATURE:
<223> OTHER INFORMATION: integrin binding site

<400> SEQUENCE: 40

Cys Lys Lys Lys Lys Lys Lys Gly Gly Arg Gly Asp Met Phe Gly
1               5                   10                  15

<210> SEQ ID NO 41
<211> LENGTH: 11
<212> TYPE: PRT
<213> ORGANISM: HIV TAT

<400> SEQUENCE: 41

Tyr Gly Arg Lys Lys Arg Arg Gln Arg Arg Arg
1               5                   10

<210> SEQ ID NO 42
<211> LENGTH: 16
<212> TYPE: PRT
<213> ORGANISM: H. sapiens

<400> SEQUENCE: 42

Ala Ala Val Ala Leu Leu Pro Ala Val Leu Leu Ala Leu Leu Ala Pro
1               5                   10                  15

<210> SEQ ID NO 43
<211> LENGTH: 12
<212> TYPE: PRT
<213> ORGANISM: H. sapiens

<400> SEQUENCE: 43

Thr Pro Pro Lys Lys Lys Arg Lys Val Glu Asp Pro
1               5                   10

<210> SEQ ID NO 44
<211> LENGTH: 27
<212> TYPE: PRT
<213> ORGANISM: Artificial sequence
<220> FEATURE:
<223> OTHER INFORMATION: engineered cell penetration peptide

<400> SEQUENCE: 44

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
                20                  25

<210> SEQ ID NO 45
<211> LENGTH: 34
<212> TYPE: PRT

<213> ORGANISM: HSV-1

<400> SEQUENCE: 45

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 46
<211> LENGTH: 16
<212> TYPE: PRT
<213> ORGANISM: Artificial sequence
<220> FEATURE:
<223> OTHER INFORMATION: a penetratin

<400> SEQUENCE: 46

Arg Gln Ile Lys Ile Trp Phe Gln Asn Arg Arg Met Lys Trp Lys Lys
1               5                   10                  15

<210> SEQ ID NO 47
<211> LENGTH: 16
<212> TYPE: PRT
<213> ORGANISM: Artificial sequence
<220> FEATURE:
<223> OTHER INFORMATION: a penetratin

<400> SEQUENCE: 47

Lys Lys Trp Lys Met Arg Arg Asn Gln Phe Trp Ile Lys Ile Gln Arg
1               5                   10                  15

<210> SEQ ID NO 48
<211> LENGTH: 16
<212> TYPE: PRT
<213> ORGANISM: Artificial sequences
<220> FEATURE:
<223> OTHER INFORMATION: a penetratin

<400> SEQUENCE: 48

Arg Gln Ile Lys Ile Trp Phe Gln Asn Arg Arg Met Lys Trp Lys Lys
1               5                   10                  15

<210> SEQ ID NO 49
<211> LENGTH: 16
<212> TYPE: PRT
<213> ORGANISM: Artificial sequence
<220> FEATURE:
<223> OTHER INFORMATION: a penetratin

<400> SEQUENCE: 49

Arg Gln Ile Lys Ile Trp Phe Gln Asn Arg Arg Met Lys Trp Lys Lys
1               5                   10                  15

<210> SEQ ID NO 50
<211> LENGTH: 16
<212> TYPE: PRT
<213> ORGANISM: Artificial sequence
<220> FEATURE:
<223> OTHER INFORMATION: a penetratin

<400> SEQUENCE: 50

Arg Gln Ile Lys Ile Trp Phe Gln Asn Arg Arg Met Lys Trp Lys Lys
1               5                   10                  15

<210> SEQ ID NO 51

```
<211> LENGTH: 16
<212> TYPE: PRT
<213> ORGANISM: Artificial sequence
<220> FEATURE:
<223> OTHER INFORMATION: a penetratin

<400> SEQUENCE: 51

Arg Gln Ile Lys Ile Trp Phe Gln Asn Met Arg Arg Lys Trp Lys Lys
1               5                   10                  15

<210> SEQ ID NO 52
<211> LENGTH: 16
<212> TYPE: PRT
<213> ORGANISM: Artificial sequence
<220> FEATURE:
<223> OTHER INFORMATION: a penetratin

<400> SEQUENCE: 52

Arg Gln Ile Arg Ile Trp Phe Gln Asn Arg Arg Met Arg Trp Arg Arg
1               5                   10                  15

<210> SEQ ID NO 53
<211> LENGTH: 16
<212> TYPE: PRT
<213> ORGANISM: Artificial sequence
<220> FEATURE:
<223> OTHER INFORMATION: a penetratin

<400> SEQUENCE: 53

Arg Arg Trp Arg Arg Trp Trp Arg Arg Trp Trp Arg Arg Trp Arg Arg
1               5                   10                  15

<210> SEQ ID NO 54
<211> LENGTH: 16
<212> TYPE: PRT
<213> ORGANISM: Artificial sequence
<220> FEATURE:
<223> OTHER INFORMATION: a penetratin

<400> SEQUENCE: 54

Arg Gln Ile Lys Ile Phe Phe Gln Asn Arg Arg Met Lys Phe Lys Lys
1               5                   10                  15

<210> SEQ ID NO 55
<211> LENGTH: 15
<212> TYPE: PRT
<213> ORGANISM: Artificial sequence
<220> FEATURE:
<223> OTHER INFORMATION: a penetratin

<400> SEQUENCE: 55

Thr Glu Arg Gln Ile Lys Ile Trp Phe Gln Asn Arg Arg Met Lys
1               5                   10                  15

<210> SEQ ID NO 56
<211> LENGTH: 15
<212> TYPE: PRT
<213> ORGANISM: Artificial sequence
<220> FEATURE:
<223> OTHER INFORMATION: a penetratin

<400> SEQUENCE: 56

Lys Ile Trp Phe Gln Asn Arg Arg Met Lys Trp Lys Lys Glu Asn
1               5                   10                  15
```

MULTIVALENT CLOSTRIDIAL TOXIN DERIVATIVES AND METHODS OF THEIR USE

This application is a non-provisional application claiming priority pursuant to 35 U.S.C. 119(e) to provisional patent application Ser. No. 60/662,151, filed on Mar. 15, 2005 and to provisional patent application Ser. No. 60/661,953 filed on Mar. 15, 2005. Each of these provisional patent applications is hereby expressly incorporated by reference herein in its entirety. Each and every patent, patent application, and other publication cited herein is expressly incorporated by reference herein in its entirety.

The present invention is drawn to multivalent *Clostridial* neurotoxin derivatives having more than one binding domain directed to a cell surface feature of a target cell.

The ability of *Clostridial* toxins, such as, e.g., Botulinum neurotoxins (BoNTs), BoNT/A, BoNT/B, BoNT/C1, BoNT/D, BoNT/E, BoNT/F and BoNT/G, and Tetanus neurotoxin (TeNT), to inhibit neuronal transmission are being exploited in a wide variety of therapeutic and cosmetic applications, see e.g., William J. Lipham, COSMETIC AND CLINICAL APPLICATIONS OF BOTULINUM TOXIN (Slack, Inc., 2004). As an example, BOTOX® is currently approved in one or more countries for the following indications: achalasia, adult spasticity, anal fissure, back pain, blepharospasm, bruxism, cervical dystonia, essential tremor, glabellar lines or hyperkinetic facial lines, headache, hemifacial spasm, hyperactivity of bladder, hyperhidrosis, juvenile cerebral palsy, multiple sclerosis, myoclonic disorders, nasal labial lines, spasmodic dysphonia, strabismus and VII nerve disorder. In addition, *Clostridial* toxin therapies are proposed for treating neuromuscular disorders, see e.g., Kei Roger Aoki et al., Method for Treating Neuromuscular Disorders and Conditions with Botulinum Toxin Types A and B, U.S. Pat. No. 6,872,397 (Mar. 29, 2005); Rhett M. Schiffman, Methods for Treating Uterine Disorders, U.S. Patent Publication No. 2004/0175399 (Sep. 9, 2004); Richard L. Barron, Methods for Treating Ulcers and Gastroesophageal Reflux Disease, U.S. Patent Publication No. 2004/0086531 (May. 7, 2004); and Kei Roger Aoki, et al., Method for Treating Dystonia with Botulinum Toxin C to G, U.S. Pat. No. 6,319,505 (Nov. 20, 2001); eye disorders, see e.g., Eric R. First, Methods and Compositions for Treating Eye Disorders, U.S. Patent Publication No. 2004/0234532 (Nov. 25, 2004); Kei Roger Aoki et al., Botulinum Toxin Treatment for Blepharospasm, U.S. Patent Publication No. 2004/0151740 (Aug. 5, 2004); and Kei Roger Aoki et al., Botulinum Toxin Treatment for Strabismus, U.S. Patent Publication No. 2004/0126396 (Jul. 1, 2004); pain, see e.g., Kei Roger Aoki et al., Pain Treatment by Peripheral Administration of a Neurotoxin, U.S. Pat. No. 6,869,610 (Mar. 22, 2005); Stephen Donovan, *Clostridial* Toxin Derivatives and Methods to Treat Pain, U.S. Pat. No. 6,641,820 (Nov. 4, 2003); Kei Roger Aoki, et al., Method for Treating Pain by Peripheral Administration of a Neurotoxin, U.S. Pat. No. 6,464,986 (Oct. 15, 2002); Kei Roger Aoki and Minglei Cui, Methods for Treating Pain, U.S. Pat. No. 6,113,915 (Sep. 5, 2000); Martin A. Voet, Methods for Treating Fibromyalgia, U.S. Pat. No. 6,623,742 (Sep. 23, 2003); Martin A. Voet, Botulinum Toxin Therapy for Fibromyalgia, U.S. Patent Publication No. 2004/0062776 (Apr. 1, 2004); and Kei Roger Aoki et al., Botulinum Toxin Therapy for Lower Back Pain, U.S. Patent Publication No. 2004/0037852 (Feb. 26, 2004); muscle injuries, see e.g., Gregory F. Brooks, Methods for Treating Muscle Injuries, U.S. Pat. No. 6,423,319 (Jul. 23, 2002); headache, see e.g., Martin Voet, Methods for Treating Sinus Headache, U.S. Pat. No. 6,838,434 (Jan. 4, 2005); Kei Roger Aoki et al., Methods for Treating Tension Headache, U.S. Pat. No. 6,776,992 (Aug. 17, 2004); and Kei Roger Aoki et al., Method for Treating Headache, U.S. Pat. No. 6,458,365 (Oct. 1, 2002); William J. Binder, Method for Reduction of Migraine Headache Pain, U.S. Pat. No. 5,714,469 (Feb. 3, 1998); cardiovascular diseases, see e.g., Gregory F. Brooks and Stephen Donovan, Methods for Treating Cardiovascular Diseases with Botulinum Toxin, U.S. Pat. No. 6,767,544 (Jul. 27, 2004); neurological disorders, see e.g., Stephen Donovan, Parkinson's Disease Treatment, U.S. Pat. No. 6,620,415 (Sep. 16, 2003); and Stephen Donovan, Method for Treating Parkinson's Disease with a Botulinum Toxin, U.S. Pat. No. 6,306,403 (Oct. 23, 2001); neuropsychiatric disorders, see e.g., Stephen Donovan, Botulinum Toxin Therapy for Neuropsychiatric Disorders, U.S. Patent Publication No. 2004/0180061 (Sep. 16, 2004); and Steven Donovan, Therapeutic Treatments for Neuropsychiatric Disorders, U.S. Patent Publication No. 2003/0211121 (Nov. 13, 2003); endocrine disorders, see e.g., Stephen Donovan, Method for Treating Endocrine Disorders, U.S. Pat. No. 6,827,931 (Dec. 7, 2004); Stephen Donovan, Method for Treating Thyroid Disorders with a Botulinum Toxin, U.S. Pat. No. 6,740,321 (May. 25, 2004); Kei Roger Aoki et al., Method for Treating a Cholinergic Influenced Sweat Gland, U.S. Pat. No. 6,683,049 (Jan. 27, 2004); Stephen Donovan, Neurotoxin Therapy for Diabetes, U.S. Pat. No. 6,416,765 (Jul. 9, 2002); Stephen Donovan, Methods for Treating Diabetes, U.S. Pat. No. 6,337,075 (Jan. 8, 2002); Stephen Donovan, Method for Treating a Pancreatic Disorder with a Neurotoxin, U.S. Pat. No. 6,261,572 (Jul. 17, 2001); Stephen Donovan, Methods for Treating Pancreatic Disorders, U.S. Pat. No. 6,143,306 (Nov. 7, 2000); cancers, see e.g., Stephen Donovan, Methods for Treating Bone Tumors, U.S. Pat. No. 6,565,870 (May 20, 2003); Stephen Donovan, Method for Treating Cancer with a Neurotoxin to Improve Patient Function, U.S. Pat. No. 6,368,605 (Apr. 9, 2002); Stephen Donovan, Method for Treating Cancer with a Neurotoxin, U.S. Pat. No. 6,139,845 (Oct. 31, 2000); and Mitchell F. Brin and Stephen Donovan, Methods for Treating Diverse Cancers, U.S. Patent Publication No. 2005/0031648 (Feb. 10, 2005); otic disorders, see e.g., Stephen Donovan, Neurotoxin Therapy for Inner Ear Disorders, U.S. Pat. No. 6,358,926 (Mar. 19, 2002); and Stephen Donovan, Method for Treating Otic Disorders, U.S. Pat. No. 6,265,379 (Jul. 24, 2001); autonomic disorders, see, e.g., Pankaj J. Pasricha and Anthony N. Kalloo, Method for Treating Gastrointestinal Muscle Disorders and Other Smooth Muscle Dysfunction, U.S. Pat. No. 5,437,291 (Aug. 1, 1995); as well as other disorders, see e.g., William J. Binder, Method for Treatment of Skin Lesions Associated with Cutaneous Cell-proliferative Disorders, U.S. Pat. No. 5,670,484 (Sep. 23, 1997); Eric R. First, Application of Botulinum Toxin to the Management of Neurogenic Inflammatory Disorders, U.S. Pat. No. 6,063,768 (May 16, 2000); Marvin Schwartz and Brian J. Freund, Method to Reduce Hair Loss and Stimulate Hair Growth, U.S. Pat. No. 6,299,893 (Oct. 9, 2001); Jean D. A. Carruthers and Alastair Carruthers, Cosmetic Use of Botulinum Toxin for Treatment of Downturned Mouth, U.S. Pat. No. 6,358,917 (Mar. 19, 2002); Stephen Donovan, Use of a *Clostridial* Toxin to Reduce Appetite, U.S. Patent Publication No. 2004/40253274 (Dec. 16, 2004); and Howard I. Katz and Andrew M. Blumenfeld, Botulinum Toxin Dental Therapies and Procedures, U.S. Patent Publication No. 2004/0115139 (Jun. 17, 2004); Kei Roger Aoki, et al., Treatment of Neuromuscular Disorders and Conditions with Different Botulinum, U.S. Patent Publication No. 2002/0010138 (Jan. 24, 2002); and Kei Roger Aoki, et al., Use of Botulinum Toxins for Treating Various Disorders and Conditions and Associated Pain, U.S.

Patent Publication No. 2004/0013692 (Jan. 22, 2004). In addition, the expected use of *Clostridial* toxins, such as, e.g., BoNTs and TeNT, in therapeutic and cosmetic treatments of humans and other mammals is anticipated to expand to an ever widening range of diseases and ailments that can benefit from the properties of these toxins.

Table 1, below, provides the amino acid sequences of the various currently known *clostridial* toxins. These toxins possess approximately 35% amino acid identity with each other and share the same functional domain organization and overall structural architecture. As stated above, *clostridial* toxins are each translated as a single chain polypeptide of approximately 150 kDa that is subsequently cleaved by proteolytic scission within a disulfide loop by a naturally-occurring protease, such as, e.g., an endogenous *clostridial* toxin protease or a naturally-occurring protease produced in the environment. This posttranslational processing yields a di-chain molecule comprising an approximately 50 kDa light chain (LC) and an approximately 100 kDa heavy chain (HC) held together by a single disulfide bond and noncovalent interactions.

Each mature di-chain molecule comprises three functionally distinct domains: 1) an enzymatic domain located in the LC that includes a metalloprotease region containing a zinc-dependent endopeptidase activity which specifically targets core components of the neurotransmitter release apparatus; 2) a translocation domain contained within the amino-terminal half of the H chain ($H_N$) that facilitates release of at least the L chain of the toxin from an endosome into the cytoplasm of the target cell; and 3) a binding domain found within the carboxyl-terminal half of the H chain ($H_C$) that determines the binding activity and binding specificity of the toxin to the receptor complex located at the surface of the target cell.

It will be understood that there exist certain strains of each of these toxins that may vary in their amino acid sequence in non-critical regions without a substantial change in the identity or activity of the indicated toxin.

TABLE 1

Clostridial Toxin Reference Sequences and Regions
(identified from amino to carboxy direction;
amino acid number to amino acid number)

| Toxin | SEQ ID NO: | LC | HN | HC |
|---|---|---|---|---|
| BoNT/A | 1 | M1-K448 | A449-K871 | N872-L1296 |
| BoNT/B | 2 | M1-K441 | A442-S858 | E859-E1291 |
| BoNT/C1 | 3 | M1-K449 | T450-N866 | N867-E1291 |
| BoNT/D | 4 | M1-R445 | D446-N862 | S863-E1276 |
| BoNT/E | 5 | M1-R422 | K423-K845 | R846-K1252 |
| BoNT/F | 6 | M1-K439 | A440-K864 | K865-E1274 |
| BoNT/G | 7 | M1-K446 | S447-S863 | N864-E1297 |
| TeNT | 8 | M1-A457 | S458-V879 | I880-D1315 |

Using this information it is possible to construct an expressible open nucleic acid reading frame for insertion into an expression vector and subsequent expression within a chosen host cell. Indeed, International Patent publication WO 01/14570 discloses methods of making single-chain, cleavable recombinant modified or unmodified *Clostridial* neurotoxin derivatives and chimeric and hybrid forms thereof using such methods. Additional publications disclosing methods of making expressible recombinant neurotoxins and derivatives thereof include U.S. Pat. Nos. 5,989,545; 6,203,794; 6,395, 513; U.S. Publication Numbers U.S. 2003/0166238; U.S. 2002/169942; U.S. 2004/176299; U.S. 2004/126397; U.S. 2005/035730; U.S. 2005/068494; U.S. 2006/011966; International Patent Applications WO95/32738; WO 99/55359; WO96/33273; WO98/07864; WO99/17806; WO98/07864; WO02/44199; WO02/40506. All these publications are incorporated by reference herein in their entirety.

The use of recombinant DNA techniques permits the construction of modified *clostridial* neurotoxins having different functional properties from the naturally occurring toxin subtypes and strains thereof. For example, altering the naturally occurring amino acid sequence of the native neurotoxin light chain and/or adding a different therapeutic moiety permits the construction of transport proteins designed to carry a therapeutic agent within a neuron. See U.S. Pat. No. 6,203,794 (incorporated by reference herein). Altering the targeting (binding) domain permits the toxin to be transported within pancreatic cells, such as acinar cells, thereby preventing secretion of activated digestive enzymes by such cells, See U.S. Pat. No. 6,843,998 (hereby incorporated by reference herein), or sensory afferent neurons, thereby preventing neurotransmitter release and thus providing relief from pain; see U.S. Pat. No. 6,395,513 (hereby incorporated by reference herein.)

In addition, the creation of chimeric neurotoxin derivatives comprising, for example, the binding domain and the translocation domain (or modified versions thereof) of one neurotoxin subtype for example, BoNT/A, and the light chain region of another neurotoxin subtype, for example, BoNT/E. It will be seen that given the general structural homology between the neurotoxin subtypes, any combination of the three basic *clostridial* neurotoxin domains, may be made in a single amino acid chain (or cleaved di-chain molecule). Thus, a binding region from any of neurotoxin subtypes A, B, C1, D, E, F, G, or TeTX may be independently combined with a translocation domain from neurotoxin subtypes A, B, C1, D, E, F, G, or TeTX, and further independently combined with a endopeptidase domain from any of neurotoxin subtypes A, B, C1, D, E, F, G or TeTX.

When discussing the three general neurotoxin domains of each *clostridial* neurotoxin subtype (binding, translocation and endopeptidase) it will be understood that *clostridial* neurotoxin research is a well-developed field, and the correlation of the amino acid sequences comprising each of these domains with their functions is well known. Additionally, the nucleotide and amino acid sequences of each of these domains are known and have been disclosed in this specification. It will therefore be understood that an endopeptidase domain, translocation domain, or the binding domain(s) of a given neurotoxin subtype may respectively and independently have 60%, or 65%, or 70%, or 75%, or 80%, or 85%, or 90%, or 95% identity to any of the amino acid sequence regions indicated in Table 1 and disclosed in SEQ ID NO: 1-8. Further, it will be understood that the amino acid sequences set forth in Table 1 and SEQ ID NO: 1-8 provide a full disclosure of any and all nucleotide sequences encoding these amino acid sequences and indicated regions thereof. A nucleotide sequence encoding an endopeptidase domain, translocation domain, or binding domain of a given neurotoxin subtype may respectively have 60%, or 65%, or 70%, or 75%, or 80%, or 85%, or 90%, or 95% identity to any of such reference nucleotide sequence regions listed in Table 1 and/or SEQ ID NO: 1, 2, 3, 4, 5, 6, 7, or 8.

BRIEF DESCRIPTION OF THE DRAWINGS

FIG. 2A depicts an embodiment of the multivalent *Clostridial* neurotoxin derivatives of the invention in which the domains "Binding 1", "Translocation" and "Endopeptidase" correspond to the domains of the naturally occurring *Clostridial* neurotoxin. In this embodiment, two additional binding sites, ("Binding 2" and "Binding 3") are inserted at the amino terminus of the single chain toxin prior to cleavage. The protease sensitive regions separating the Translocation and Endopeptidase domain and the Binding 2 and Binding 3 domains may independently comprise naturally occurring loop region amino acid sequences, or may contain an engineered protease sensitive amino acid sequence. Two cysteine residues create a disulfide linkage between the Translocation and Endopeptidase domains and the Binding 1 and Binding 2 domains.

FIG. 2B shows the multivalent *Clostridial* neurotoxin derivative of FIG. 2A after protease cleavage. The Binding 1 and Binding 2 sites are part of the Translocation and Endopeptidase domains, respectively, while the Binding 3 site comprises a separate disulfide-linked chain.

DETAILED DESCRIPTION

Figure 1:
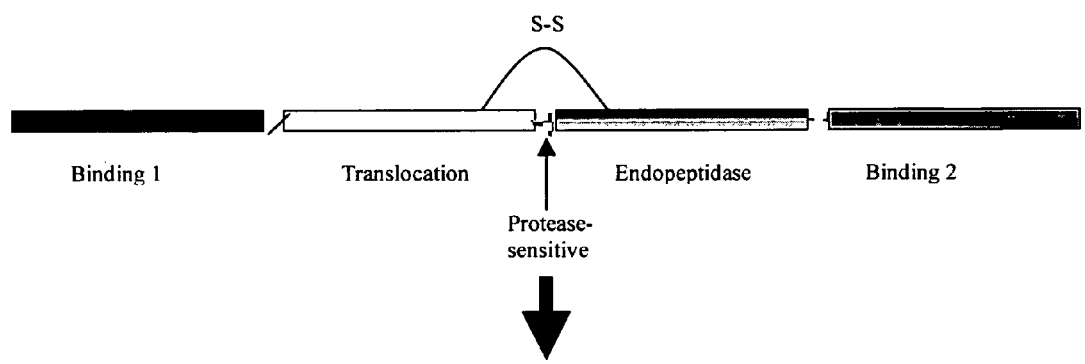
FIG. 1A depicts an embodiment of the multivalent *Clostridial* neurotoxin derivatives of the invention in which the domains "Binding 1", "Translocation" and "Endopeptidase" correspond to the domains of the naturally occurring Clostridial neurotoxin. In this embodiment, a second binding domain, "Binding 2", is inserted at the amino terminus of the single chain toxin prior to cleavage. The protease sensitive region separating the Translocation and Endopeptidase domains may be the naturally occurring loop region, or may contain an engineered protease sensitive amino acid sequence. Two cysteine residues create a disulfide linkage between the Translocation and Endopeptidase domains.
FIG. 1B shows the multivalent *Clostridial* neurotoxin derivative of FIG. 1A after protease cleavage. The Binding 1 and Binding 2 sites are part of the Translocation and Endopeptidase domains, respectively.
Figure 1:
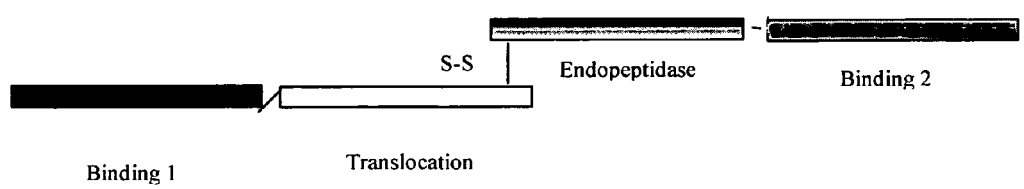

The binding and/or selectivity and thus, the therapeutic utility of a naturally occurring or modified *clostridial* neurotoxin may be enhanced or altered by inclusion of at least 2 target cell-binding domains. All such enhanced or altered *Clostridial* neurotoxins are referred to herein as "multivalent *Clostridial* neurotoxin derivatives" or MCNDs. By adding, for example, multiple binding domains the binding constant (Kd) (which equals [toxin] [target cell]/[toxin:target cell complex]) of the MCND will be increased over that of a monovalent toxin or toxin derivative.

Each binding domain of a MCND may comprise any ligand capable of binding under physiological conditions to a cell surface receptor capable of selectively binding to the ligand; however each such binding domain is capable of binding to, or facilitating the entry of the MCND to, a single target cell type. In addition, at least one of said binding domains will bind selectively to the target cell and at least one of the binding domains will bind to a cell surface receptor capable of mediating the internalization of the MCND within the target cell.

By "cell surface receptor" is meant both a traditional receptor capable of binding a ligand and thereby causing a ligand-selective response (at e.g., the cell surface, the cytoplasm, or both), and a cell surface feature such as caveolae, membrane "patches", or lipid rafts, which appear to serve at least in part to gather together and locally concentrate at the cell surface specific receptors and bound ligand types for later processing such as endocytosis, often mediated by a cell surface receptor. By "selective binding" between ligand and such a cell surface receptor is meant that the dissociation constant (Kd) of ligand for target is at least four fold, or preferably at least 10 fold, or preferably at least 50 fold, or preferably at least 100 fold, or preferably at least 1000, or preferably at least 100,000 fold the value of Kd of the ligand for other cell surface receptors.

In one embodiment therefore, the present invention is drawn to a composition comprising a multivalent *Clostridial* neurotoxin derivative having an endopeptidase domain which selectively cleaves a vSNARE or tSNARE protein; a translocation domain which assists in the migration of the endopeptidase through a vesicular membrane, and at least two binding domains, each independently capable of binding a cell surface receptor of the desired target cell. The binding domains may be identical or different; however both domains bind target cell surface receptors on the surface of the target cell.

In one broad embodiment the target cell may be a natural target of a *Clostridial* neurotoxin. For example, the target cell may be a neuron located at the neuromuscular junction. In such a case, one or more of the binding domains of the multivalent *Clostridial* neurotoxin derivative of the present invention may be the naturally-occurring $H_C$ domain of the *Clostridium botulinum* subtypes or of TeTX. However, one or more of the binding domains may comprise a ligand that does not comprise a naturally occurring neurotoxin $H_C$ domain. For example, one or more binding domain may comprise a domain of a hemagglutinin (HA) or non-toxin non-hemagglutinin (NTNH) protein constituent of a *clostridial* toxin complex.

Any of a variety of sequence alignment methods can be used to determine percent identity of a multivalent *Clostridial* neurotoxin derivative, or of an endopeptidase, translocation, or binding domain thereof, relative to a given naturally-occurring *Clostridial* neurotoxin, or of the respective domains it comprises. Such methods may include, without limitation, global methods, local methods and hybrid methods, such as, e.g., segment approach methods. Protocols to determine percent identity are routine procedures within the scope of one skilled in the art and from the teaching herein.

Approaches well known to one skilled in the art on how to modify a *Clostridial* neurotoxin in order to increase its binding activity for an endogenous *Clostridial* toxin receptor system present on a naturally-occurring *Clostridial* toxin target cell. As described above, one approach involves identifying amino acids using computational protein design algorithms; changing specifically-identified amino acids using, without limitation, site-directed mutagenesis, oligonucleotide-directed mutagenesis and site-specific mutagenesis; and testing the relevant activity (selective endopeptidase activity, translocation activity, or binding activity) of multivalent *Clostridial* neurotoxin derivatives using relevant assays, e.g., heterogeneous assays, homogeneous assays and non-separating homogeneous assays. It is further envisioned that the binding activity of a multivalent *Clostridial* neurotoxin derivative having altered or enhanced binding domains, as disclosed in the present specification, can be determined by, for example, affinity chromatography using immobilized receptors and interfacial optical assays. In another approach described above, a binding activity of a multivalent *Clostridial* neurotoxin derivative for a cell surface receptor present on a target cell can be achieved using directed-evolution methods. Similar methods can be used to alter the endopeptidase domain's substrate selectivity.

A multivalent *Clostridial* neurotoxin derivative includes, without limitation, naturally occurring *Clostridial* toxin domains, such as, e.g., naturally occurring *Clostridial* endopeptidase, translocation and at least 2 naturally occurring *Clostridial* toxin binding domains, each such domain from the same or different *Clostridial* toxin types, isoforms; non-naturally occurring *Clostridial* domain variants, such as, e.g., conservative *Clostridial* domain variants, non-conservative *Clostridial* domain variants, *Clostridial* domain chimerics, active *Clostridial* domain fragments thereof, or any combination thereof.

As used herein, the term "*Clostridial* domain variant", whether naturally-occurring or non-naturally-occurring, means a *Clostridial* endopeptidase, translocation, or binding domains that has at least one amino acid change from the corresponding region of the disclosed reference sequences (see Table 1) and can be described in terms of percent identity to the corresponding region of that reference sequence. Unless expressly indicated, all *Clostridial* domain variants disclosed in the present specification are capable of executing the endopeptidase, translocation, and/or target cell binding step of the intoxication process.

It is recognized by those of skill in the art that within each *Clostridial* bacterium there can be naturally occurring *Clostridial* toxin variants having *Clostridial* domain variants that differ somewhat in their amino acid sequence, and also in the nucleic acids encoding these proteins, from the sequences provided in Table 1 and SEQ ID NO: 1-8 above.

As used herein, the term "naturally occurring *Clostridial* domain variant" means any *Clostridial* domain (endopeptidase, translocation, and/or binding domains) produced by a naturally-occurring process, including, without limitation, *Clostridial* domain isoforms produced from alternatively-spliced transcripts, *Clostridial* domain isoforms produced by spontaneous mutation and *Clostridial* domain subtypes. A naturally occurring *Clostridial* domain variant can function in substantially the same manner as the reference *Clostridial* domain on which the naturally occurring *Clostridial* domain variant is based, and can be substituted for the reference *Clostridial* domain in any aspect of the present invention. A naturally occurring *Clostridial* domain variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids or 100 or more amino acids from the reference *Clostridial* domain on which the naturally occurring *Clostridial* domain variant is based. A naturally occurring *Clostridial* domain variant can also substitute at least 10 contiguous amino acids, at least 15 contiguous amino acids, at least 20 contiguous amino acids, or at least 25 contiguous amino acids from the reference *Clostridial* domain on which the naturally occurring *Clostridial* domain variant is based, that possess at least 50% amino acid identity, 65% amino acid identity, 75% amino acid identity, 85% amino acid identity or 95% amino acid identity to the reference *Clostridial* domain on which the naturally occurring *Clostridial* domain variant is based.

Non-toxin Associated Proteins (NAPs)

HA and NTNH regions, including, without limitation, regions of non-toxin associated proteins of *Clostridial* toxins, such as, e.g., non-toxic non-hemagglutinin (NTNH), hemagglutinin-17 (HA-17), hemagglutinin-33 (HA-33) and hemagglutinin-70 (HA-70) may provide an enhanced targeting domain that increases binding activity for an endogenous *Clostridial* toxin receptor system present on a naturally-occurring *Clostridial* toxin target cell. As indicated previously, *Clostridial* bacteria produce a toxin complex that comprises the approximately 150-kDa di-chain *Clostridial* toxin along with other proteins. These other proteins are collectively called nontoxin associated proteins (NAPs). Identified NAPs include proteins possessing hemaglutination activity, such, e.g., a hemagglutinin of approximately 17-kDa (HA-17), a hemagglutinin of approximately 33-kDa (HA-33) and a hemagglutinin of approximately 70-kDa (HA-70); as well as a non-toxic non-hemagglutinin (NTNH), a protein of approximately 130-kDa, see, e.g., Eric A. Johnson and Marite Bradshaw, *Clostridial botulinum and its Neurotoxins: A Metabolic and Cellular Perspective*, 39 TOXICON 1703-1722 (2001); and Stephanie Raffestin et al., Organization and Regulation of the *Neurotoxin Genes in Clostridium botulinum and Clostridium tetani*, 10 ANAEROBE 93-100 (2004). The toxin complex is believed to be important for the intoxication process at least in part because it appears to provide protection to the toxin molecule from adverse environmental conditions and resistance to protease digestion. Importantly, certain domains of the HA and NTNH proteins appear to coordinate with toxin binding and bind to locations on the cell surface (and may bind to the natural *Clostridial* neurotoxin cell surface receptor at sites other than or additional to the toxin binding site), thus facilitating binding, internalization, and activation of the toxin.

Recent crystallography experiments have revealed that HA-17, HA-33 and NTNH from various *Clostridial* bacteria contain a region comprising β-trefoil domains very similar to the single β-trefoil domain present in the binding domain of *Clostridial* toxins, see, e.g., Kaoru Inoue et al., *Structural Analysis by X-Ray Crystallography and Calorimetry of a Haemagglutinin Component (HA1) of the Progenitor Toxin from Clostridium botulinum*, 149 MICROBIOL. 3361-3370 (2003); and Joseph W. Arndt et al., *The Structure of the Neurotoxin-Associated Protein HA33/A from Clostridial botulinum Suggests a Reoccurring β-trefoil Fold in the Progenitor Toxin Complex*, 346 J. MOL. BIOL. 1083-1093 2005). For example, HA-33 from *Clostridum botulinum* serotype A has two β-trefoil domains, each of which consists of three potential carbohydrate binding moieties or β-trefoil folds, designated 1α (amino acids 10-55 of SEQ ID NO: 9), 1β (amino acids 56-102 of SEQ ID NO: 9) and 1γ (amino acids 103-144 of SEQ ID NO: 9) for the first β-trefoil domain and 2α (amino acids 151-197 of SEQ ID NO: 9), 2β (amino acids 198-245 of SEQ ID NO: 9) and 2γ (amino acids 246-293 of SEQ ID NO: 9) for the second β-trefoil domain. Mutations in conserved amino acids of the carbohydrate binding moiety result in a loss of carbohydrate binding, see, e.g., Kaoru Inoue et al., *Structural Analysis by X-Ray Crystallography and Calorimetry of a Haemagglutinin Component (HA1) of the Progenitor Toxin from Clostridium botulinum*, 149 MICROBIOL. 3361-3370 (2003).

These β-trefoil domains are also found in the HA-33 proteins produced by *Clostridium botulinum* serotype B, serotype C1 and serotype D and sequence alignments revealed that amino acids essential for overall carbohydrate binding are conserved. The amino acids predicted to be important or essential for carbohydrate binding are as follows Asp 263, Tyr 265, Gln 268, Gln 276, Phe 278 and Gln 286 of HA-33/A1 of SEQ ID NO: 9, HA-33/A2 of SEQ ID NO: 10, HA-33/A3 of SEQ ID NO: 11, HA-33/A5 of SEQ ID NO: 12 and HA-33/B2 of SEQ ID NO: 15; Asp 264, Tyr 266, Gln 269, Gln 277, Phe 279 and Gln 287 of HA-33/A4 of SEQ ID NO: 12; Asp 262, Tyr 264, Gln 267, Gln 275, Phe 277 and Gln 285 of HA-33/B1 of SEQ ID NO: 14; Asp 255, Val 257, Gly 260, Gln 268, Typ 270 and Gln 278 of HA-33/C1 of SEQ ID NO: 16; and Asp 256, Tyr 258, Gln 261, Ise 269, Asp 271 and Gln 279 of HA-33/C2 of SEQ ID NO: 17 and HA-33/D of SEQ ID NO: 18. Immunoaffinity column chromatography and pull-down assays have shown that HA-33 an bind synaptotagmin II, a putative *Clostridial* toxin receptor, see, e.g., Yu Zhou et al., *Haemagglutinin-33 of Type Q Botulinum Neurotoxin Complex Binds with Synaptotagmin II*, 272 FEBS LETT. 2717-

2726 (2005). The amino acid sequences comprising the β-trefoil domains found in various *Clostridial* HA-33 proteins are shown in Tables 2 and 3.

TABLE 2

β-trefoil Domains of Clostridial HA-33 Proteins

| | | Amino Acid Sequence Region of Carbohydrate Binding Moieties | | | | |
|---|---|---|---|---|---|---|
| Protein | SEQ ID NO: | 1α-fold | 1β4/β5 β-hairpin turn | 1β-fold | 1β8/β9 β-hairpin turn | 1γ-fold |
| HA-33/A1 | 9 | 10-54 | 55-59 | 60-100 | 101-104 | 105-144 |
| HA-33/A2 | 10 | 10-54 | 55-59 | 60-100 | 101-104 | 105-144 |
| HA-33/A3 | 11 | 10-54 | 55-59 | 60-100 | 101-104 | 105-144 |
| HA-33/A4 | 12 | 10-56 | 57-61 | 62-102 | 103-106 | 107-146 |
| HA-33/A5 | 13 | 10-54 | 55-59 | 60-100 | 101-104 | 105-144 |
| HA-33/B1 | 14 | 10-54 | 55-59 | 60-100 | 101-104 | 105-144 |
| HA-33/B2 | 15 | 10-56 | 57-61 | 62-102 | 103-106 | 107-146 |
| HA-33/C1-1 | 16 | 10-54 | 55-59 | 60-98 | 99-102 | 103-141 |
| HA-33/C1-2 | 17 | 10-54 | 55-59 | 60-98 | 99-102 | 103-141 |
| HA-33/D1 | 18 | 10-54 | 55-59 | 60-98 | 99-102 | 103-141 |

TABLE 3

β-trefoil Domains of Clostridial HA-33 Proteins

| | | Amino Acid Sequence Region of Carbohydrate Binding Moieties | | | | |
|---|---|---|---|---|---|---|
| Protein | SEQ ID NO: | 2α-fold | 2β4/β5 β-hairpin turn | 2β-fold | 2β8/β9 β-hairpin turn | 2γ-fold |
| HA-33/A1 | 9 | 151-195 | 196-199 | 200-242 | 243-248 | 249-293 |
| HA-33/A2 | 10 | 151-195 | 196-199 | 200-242 | 243-248 | 249-293 |
| HA-33/A3 | 11 | 151-195 | 196-199 | 200-242 | 243-248 | 249-293 |
| HA-33/A4 | 12 | 153-197 | 198-201 | 202-243 | 244-249 | 250-294 |
| HA-33/A5 | 13 | 151-195 | 196-199 | 200-242 | 243-248 | 249-279 |
| HA-33/B1 | 14 | 151-195 | 196-199 | 200-241 | 242-247 | 248-292 |
| HA-33/B2 | 15 | 153-197 | 198-201 | 200-242 | 243-248 | 249-291 |
| HA-33/C1-1 | 16 | 148-190 | 191-194 | 195-234 | 235-240 | 241-285 |
| HA-33/C1-2 | 17 | 148-190 | 191-194 | 195-235 | 236-241 | 242-286 |
| HA-33/D1 | 18 | 148-190 | 191-194 | 195-235 | 236-241 | 242-286 |

Further analysis of the β-trefoil domain sequence of HA-33 also identified β-trefoil domains in HA-17 and NTNH, see, e.g., Joseph W. Arndt et al., *The Structure of the Neurotoxin-Associated Protein HA33/A from Clostridial botulinum Suggests a Reoccurring β-trefoil Fold in the Progenitor Toxin Complex,* 346 J. Mol. Biol. 1083-1093 (2005). The HA-17 comprises a single β-trefoil domain containing three carbohydrate binding moieties or β-trefoil folds. The carbohydrate binding moieties of HA-17 exhibits the greatest sequence similarity with the 2γ carbohydrate-binding moiety of HA-33. These β-trefoil domains are also found in the HA-17 proteins produced by *Clostridium botulinum* serotype B, serotype C1 and serotype D and sequence alignments revealed that amino acids essential for overall carbohydrate binding are conserved. The amino acids predicted to be important or essential for carbohydrate binding are as follows Tyr 110, Typ 112, Tyr 115, Pro 130, Phe 132 and Asn 138 of HA-17/A of SEQ ID NO: 19, HA-17/B of SEQ ID NO: 20, HA-17/C1 of SEQ ID NO: 21 and HA-17/D of SEQ ID NO: 22. The amino acid sequences comprising the β-trefoil domains found in various *Clostridial* HA-17 proteins are shown in Table 4.

TABLE 4

β-trefoil Domains of Clostridial HA-17 Proteins

| | | Amino Acid Sequence Region of Carbohydrate Binding Moieties | | | | |
|---|---|---|---|---|---|---|
| Protein | SEQ ID NO: | α-fold | β4/β5 β-hairpin turn | β-fold | β8/β9 β-hairpin turn | γ-fold |
| HA-17/A | 19 | 9-50 | 51-54 | 55-91 | 92-94 | 95-146 |
| HA-17/B | 20 | 9-50 | 51-54 | 55-91 | 92-94 | 95-146 |
| HA-17/C1 | 21 | 9-50 | 51-54 | 55-91 | 92-94 | 95-146 |
| HA-17/D | 22 | 9-50 | 51-54 | 55-91 | 92-94 | 95-146 |

NTNH proteins from various *Clostridial* bacteria show significant sequence similarity to the β-trefoil domains present in the cell-binding domain of BoNT/A and TeNT. The high degree of structural similarity is interesting in light of the low primary sequence similarity between NTNH and the *Clostridial* toxins themselves. Furthermore, since NTNH of the various serotypes have greater sequence similarity than the *Clostridial* toxins, it is likely that the NTNH produced by other *Clostridial* strains will also have β-trefoil domains exhibiting high structural similarity with the binding domains of *Clostridial* toxins. The β-trefoil domains of various *Clostridial* NTNHs are as follows: amino acids 1050-1193 of NTNH/A1 of SEQ ID NO: 23; amino acids 1050-1198 of NTNH/A2 of SEQ ID NO: 24; amino acids 1050-1193 of NTNH/A3 of SEQ ID NO: 25; amino acids 1049-1197 of NTNH/B of SEQ ID NO: 26; amino acids 1049-1196 of NTNH/C1 of SEQ ID NO: 27; amino acids 1049-1196 of NTNH/D of SEQ ID NO: 28; amino acids 1014-1162 of NTNH/E of SEQ ID NO: 29; amino acids 1016-1159 of NTNH/F1 of SEQ ID NO: 30; amino acids 1017-1165 of NTNH/F2 of SEQ ID NO: 31; and amino acids 1050-1198 of NTNH/G of SEQ ID NO: 32. The amino acid sequences comprising the β-trefoil domains found in various *Clostridial* NTNH proteins are shown in Table 5.

The β-trefoil domains present in the *Clostridial* toxin, HA-33, HA-17 and NTNH collectively form nearly half the mass of a *Clostridial* toxin complex and underlies the apparent importance of carbohydrate binding in the cell-binding step of the intoxication process. This observation is further enhanced by the fact that a *Clostridial* toxin alone is not as effective in intoxicating a cell as the entire toxin complex. One potential explanation for this enhanced binding activity is the presence, both in type and in quantity, of the β-trefoil domains present in HA-33, HA-17 and NTNH. Therefore, the high prediction of structural similarity of the β-trefoil domains present in HA-33, HA-17 and NTNH relative to the β-trefoil domain found in *Clostridial* toxins provides a potential source of binding domains useful for developing multivalent *Clostridial* neurotoxin derivatives with enhanced binding activity. As a non-limiting example, such a multivalent *Clostridial* neurotoxin derivative may comprise one or more carbohydrate binding moiety or a β-trefoil fold from HA-33, HA-17 or NTNH. Such a NAP binding motif may be substituted for, or added to, the naturally occurring binding domain (or a variant thereof) present in a *Clostridial* toxin. As yet another non-limiting example, 2 or more carbohydrate binding moieties or β-trefoil folds from HA-33, HA-17 or NTNH can be substituted in a multivalent *Clostridial* neurotoxin derivative for the naturally occurring carbohydrate binding moiety (or a variant thereof) present in a *Clostridial* toxin. As still another non-limiting example, two or more carbohydrate binding moieties or β-trefoil folds from HA-33, HA-17 or NTNH can be added in addition to the naturally occurring carbohydrate binding moiety present in a *Clostridial* toxin. As another non-limiting example, multiple carbohydrate binding moieties or a β-trefoil folds from a *Clostridial* toxin binding domain can be added in addition to the naturally occurring carbohydrate binding moiety present in a *Clostridial* toxin.

binding affinity or a binding specificity, to a statistically significantly degree relative to an unmodified naturally occurring *Clostridial* toxin binding domain from a *Clostridial* toxin. By definition, a NAP with enhanced binding activity has at least one amino acid change from the corresponding region of the disclosed reference sequences (see Tables 2-5) and can be described in percent identity to the corresponding region of that reference sequence.

Any of a variety of sequence alignment methods can be used to determine percent identity of a modified *Clostridial* NAP relative to a naturally-occurring *Clostridial* NAP, including, without limitation, global methods, local methods and hybrid methods, such as, e.g., segment approach methods. Protocols to determine percent identity are routine procedures within the scope of one skilled in the art and from the teaching herein.

Approaches well known to one skilled in the art on how to modify a *Clostridial* NAP in order to increase its binding activity for an endogenous *Clostridial* toxin receptor system present on a naturally-occurring *Clostridial* toxin target cell. As described above, one approach involves identifying amino acids using computational protein design algorithims; changing specifically-identified amino acids using, without limitation, site-directed mutagenesis, oligonucleotide-directed mutagenesis and site-specific mutagenesis; and testing the binding activity of multivalent *Clostridial* neurotoxin derivatives comprising a modified *Clostridial* NAP with enhanced binding activity using, e.g., heterogeneous assays, homogeneous assays and non-separating homogeneous assays. It is further envisioned that the binding activity of a multivalent *Clostridial* neurotoxin derivative disclosed in the present specification can be determined by affinity chromatography using immobilized receptors and interfacial optical assays. In another approach described above, a binding activity of a modified *Clostridial* NAP for a naturally occurring

TABLE 5

β-trefoil Domains of Clostridial NTNH Proteins

Amino Acid Sequence Region of Carbohydrate Binding Moieties

| Protein | SEQ ID NO: | α-fold | β4/β5 β-hairpin turn | β-fold | β8/β9 β-hairpin turn | γ-fold |
|---|---|---|---|---|---|---|
| NTNH/A1 | 23 | 1050-1097 | 1098-1110 | 1111-1138 | 1139-1148 | 1149-1194 |
| NTNH/A2 | 24 | 1050-1097 | 1098-1110 | 1111-1139 | 1140-1148 | 1149-1199 |
| NTNH/A3 | 25 | 1050-1097 | 1098-1110 | 1111-1138 | 1139-1148 | 1149-1194 |
| NTNH/B | 26 | 1049-1096 | 1097-1109 | 1110-1138 | 1139-1147 | 1148-1198 |
| NTNH/C1 | 27 | 1049-1096 | 1097-1109 | 1110-1138 | 1139-1147 | 1148-1197 |
| NTNH/D | 28 | 1049-1096 | 1097-1109 | 1110-1138 | 1139-1147 | 1148-1197 |
| NTNH/E | 29 | 1014-1061 | 1062-1074 | 1075-1103 | 1104-1113 | 1114-1163 |
| NTNH/F1 | 30 | 1016-1063 | 1064-1076 | 1077-1104 | 1105-1114 | 1115-1160 |
| NTNH/F2 | 31 | 1017-1064 | 1065-1077 | 1078-1106 | 1107-1116 | 1117-1166 |
| NTNH/G | 32 | 1050-1097 | 1098-1110 | 1111-1139 | 1140-1149 | 1150-1199 |

As used herein, the term "Non-toxin Associated Protein" is synonymous with "NAP" and means a *Clostridial* NAP with selective binding activity, such as, e.g., a binding affinity or a binding specificity, for an endogenous *Clostridial* toxin receptor system. It is envisioned that both naturally occurring NAPs as well as NAPs with enhanced binding activity can be used to practice aspects of the present invention. As used herein, the term "NAP with enhanced binding activity" means a *Clostridial* NAP with enhanced binding activity for an endogenous *Clostridial* toxin receptor system, such as, e.g., a *Clostridial* toxin receptor system present on a naturally occurring *Clostridial* toxin target cell can be achieved using directed-evolution methods.

A *Clostridial* NAP includes, without limitation, naturally Occurring *Clostridial* NAP variants, such as, e.g., *Clostridial* NAP isoforms and *Clostridial* NAP subtypes; non-naturally occurring *Clostridial* NAP variants, such as, e.g., conservative *Clostridial* NAP variants, non-conservative *Clostridial* NAP variants, *Clostridial* NAP chimerics, active *Clostridial* NAP fragments thereof, or any combination thereof.

As used herein, the term "*Clostridial* NAP variant," whether naturally-occurring or non-naturally-occurring, means a *Clostridial* NAP that has at least one amino acid change from the corresponding region of the disclosed reference sequences (see Tables 2-5) and can be described in terms of percent identity to the corresponding region of that reference sequence. Unless expressly indicated, all *Clostridial* NAP variants disclosed in the present specification are capable of executing the cell-binding step of the intoxication process.

It is recognized by those of skill in the art that within each *Clostridial bacterium* there can be naturally occurring *Clostridial* NAP variants that differ somewhat in their amino acid sequence, and also in the nucleic acids encoding these proteins. For example, there are presently known five *Clostridial botulinum* serotype A HA-33 variants, HA-33/A1, HA-33/A2, HA-33/A3, HA-33/A4 and HA-33/A5 (Tables 2 and 3), with specific HA-33 variants showing various degrees of amino acid divergence when compared to another HA-33 variant. As another example, there are presently three *Clostridial botulinum* serotype A NTNH-33 variants, NTNH/A1, NTNH/A2 and NTNH/A3 (Table 5), with specific NTNH variant showing various degrees of amino acid divergence when compared to another NTNH variant. As used herein, the term "naturally occurring *Clostridial* NAP variant" means any *Clostridial* NAP produced by a naturally-occurring process, including, without limitation, *Clostridial* NAP isoforms produced from alternatively-spliced transcripts, *Clostridial* NAP isoforms produced by spontaneous mutation and *Clostridial* NAP subtypes. A naturally occurring *Clostridial* NAP variant can function in substantially the same manner as the reference *Clostridial* NAP on which the naturally occurring *Clostridial* NAP variant is based, and can be substituted for the reference *Clostridial* NAP in any aspect of the present invention. A naturally occurring *Clostridial* NAP variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids or 100 or more amino acids from the reference *Clostridial* NAP on which the naturally occurring *Clostridial* NAP variant is based. A naturally occurring *Clostridial* NAP variant can also substitute at least 10 contiguous amino acids, at least 15 contiguous amino acids, at least 20 contiguous amino acids, or at least 25 contiguous amino acids from the reference *Clostridial* NAP on which the naturally occurring *Clostridial* NAP variant is based, that possess at least 50% amino acid identity, 65% amino acid identity, 75% amino acid identity, 85% amino acid identity or 95% amino acid identity to the reference *Clostridial* NAP on which the naturally occurring *Clostridial* NAP variant is based.

Non-limiting examples of naturally occurring *Clostridial* NAP variant are each of the following *Clostridial* NAP isoform such as, e.g., a *Clostridial botulinum* serotype A HA-33 isoform, a *Clostridial botulinum* serotype B HA-33 isoform, a *Clostridial botulinum* serotype C1 HA-33 isoform, a *Clostridial botulinum* serotype D HA-33 isoform, a *Clostridial botulinum* serotype A HA-17 isoform, a *Clostridial botulinum* serotype B HA-17 isoform, a *Clostridial botulinum* serotype C1 HA-17 isoform, a *Clostridial botulinum* serotype D HA-17 isoform, a *Clostridial botulinum* serotype A NTNH isoform, a *Clostridial botulinum* serotype B NTNH isoform, a *Clostridial botulinum* serotype C1 NTNH isoform, a *Clostridial botulinum* serotype D NTNH isoform, a *Clostridial botulinum* serotype E NTNH isoform, a *Clostridial botulinum* serotype F NTNH isoform and a *Clostridial botulinum* serotype G NTNH isoform. A *Clostridial* NAP isoform can function in substantially the same manner as the reference *Clostridial* NAP on which the *Clostridial* NAP isoform is based, and can be substituted for the reference *Clostridial* NAP in any aspect of the present invention.

Cell Surface Receptors

Each of the two or more binding domains in a multivalent *Clostridial* neurotoxin derivative may be, for example, a targeting moiety or moiety that enhances stability, solubility and/or cell penetration (see below). At least one such binding domain is selective for a cell surface receptor of a target cell. In addition, at least one cell surface receptor to which a multivalent *Clostridial* neurotoxin derivative binds is capable of being internalized by the target cell after ligand binding. Preferably, at least one cell surface receptors to which a multivalent *Clostridial* neurotoxin derivative selectively binds is capable of being internalized by the target cell after ligand binding.

Each binding domain of a multivalent *Clostridial* neurotoxin derivative may independently be a ligand. Non-limiting examples of ligands or binding partners include native, recombinant and modified cell surface receptor binding domains (e.g. $H_C$ from serotypes A-G and TeTx) or one or more of the BoNT complex proteins (e.g. HA, NTNH). Such ligands have been described above. In addition, peptide or protein ligands may target specific cellular receptors that do not normally bind BONT or TeTx.

Examples of the latter category of ligands include, but are not restricted to, the transforming growth factor beta (TGF-$\beta$) family of receptors and ligands (such as, without limitation, bone morphogenetic protein (BMP)); growth factor receptor ligands (e.g. (BDNF bone-derived neurotropic factor) at TrkB, insulin-like growth factor at IGF1,2); and visceral (gut) peptides (e.g. gastrin, VIP, bombesin, etc). As described herein, "ligand" is not limited to entities selectively binding to receptors, but may include any moiety that enhances binding stable binding of the multivalent *Clostridial* neurotoxin derivative at the cell surface.

Other ligands that may be employed in accordance with the present invention are disclosed in U.S. Pat. No. 6,843,998, No. 6,641,820, No. 6,831,059, and No. 5,989,545. The disclosures of which are incorporated in their entirety herein by reference.

In some embodiments, the ligand is CPN/A (centrally presented nociceptin-A), CPNvar/A, opioid, galanin and/or somatostatin. In some embodiments, a CPN/A, CPNvar/A, opioid, galanin and/or somatostatin is/are attached to the toxin at the nicking loop.

In some embodiments, the ligand is capable of selective binding to presynaptic receptors such as those selectively binding members of the growth factor families; for example, the fibroblast growth factor (FGF) family, the epidermal growth factor (EGF) family, the insulin-like growth factor (IGF) family; neurotrophins such as nerve growth factor (NGF), bone derived neurotrophic factor (BDNF), NT-3, NT-4/5); members of the transforming growth factor TGF-beta family, such as Gbb, BMP; Neurexin (neuroligin); Frizzled (WNTs); Neuroleukin/AMF/MF receptor; Axon guidance signaling (netrin, semaphoring, ephrin type interactions; neuroregulatory cytokines (e.g., CNTF, GPA, LIF, interleukins, oncostatin M, CT-1, CLC.

In some embodiments, the ligand is capable of selective binding to cell surface receptors pf the post-synaptic membrane; for example: sequestration proteins at neuromuscular junction such as Ng-CAM (L1), NCAM, and N-cadherin.

In some embodiments, a ligand of the multivalent *Clostridial* neurotoxin derivative of the present invention is Substance P or a derivative or modified polypeptide based thereupon. Substance P is an 11 amino acid peptide that has a number of different natural and synthetic precursor forms. A representative listing of certain substance P-related compositions is provided by Table 6 below; all of these amino acid sequences are based on those set forth (left to right correlating from amino to carboxyl terminus) as SEQ ID NO: 33 (Arg-Pro-Lys-Pro-Gln-Gln-Phe-Phe-Gly-Leu-Met), SEQ ID NO: 34 (Arg-Pro-Lys-Pro-Gln-Gln-Phe-Phe-Gly-Leu-Met-Gly) and SEQ ID NO: 35 (Arg-Pro-Lys-Pro-Gln-Gln-Phe-Phe-Gly-Leu-Met-Gly-Lys) and SEQ ID NO: 36 (Arg-Pro-Lys-Pro-Gln-Gln-Phe-Phe-Gly-Leu-Met-Gly-Lys-Arg). The following are representative and not exhaustive examples of Substance P variants. Naturally occurring Substance P possesses the amino acid sequence SEQ ID NO: 33, with an amidated carboxy terminus. Longer variants are also known.

```
Arg-Pro-Lys-Pro-Gln-Gln-Phe-Phe-     (SEQ ID NO: 34)
Gly-Leu-Met-Gly

Arg-Pro-Lys-Pro-Gln-Gln-Phe-Phe-     (SEQ ID NO: 35)
Gly-Leu-Met-Gly-Lys

Arg-Pro-Lys-Pro-Gln-Gln-Phe-Phe-     (SEQ ID NO: 36)
Gly-Leu-Met-Gly-Lys-Arg
```

Each of these molecules may also possess modifications such as methyl or ethyl esters at the carboxy terminus. In addition, fragment of Substance P may function to binding receptors at cell surface; such fragments may include peptide fragments comprising the N-terminal 4, 5, 6, 7, 8, 9, or 10 amino acids of SEQ ID NO: 33.

In certain embodiments of the present invention, the multivalent *Clostridial* neurotoxin derivative of the present invention may contain two or more identical or different binding domains comprising substance P or a substance P derivative or analog; such a multivalent *Clostridial* neurotoxin derivative may be administered to neural cells in order to treat pain. In other embodiments the Substance P derived binding domain of the multivalent *Clostridial* neurotoxin derivative may be combined with different additional binding domains (such as binding domains that directly or indirectly bind to clatherin, or a caveolin-1 binding region of a glycosyl phosphatylinositol (GPI)-linked membrane protein.) engineered to provide cooperative and therefore stronger binding than would otherwise be provided using a monovalent neurotoxin.

One major route of receptor-mediated endocytosis is by means of endocytotic coated pits. These specialized sites on the plasma membrane of eukaryotic cells are responsible for internalization of many cell surface receptors, usually after ligand binding. The coated pits serve in part to concentrate the receptors for internalization within far fewer endosomes than would be the case if each receptor were individually internalized.

Coated pits consist largely of two major proteins: clatherin and the adaptor protein (adaptin) Adaptor Protein-2 (AP-2). Assembly of the coated pit is thought to be initiated by the binding of AP-2 molecules to a receptor or ligand-docking site in the membrane. The receptor:AP-2 complex then recruits the structural protein clatherin.

Sorting signals present in many membrane proteins, such as cell surface receptors, provide for recognition and binding of AP-2 to these proteins as the initial step of coated pit formation. One common sorting signal is the amino acid sequence YXXΦ (wherein Φ is an amino acid with a bulky hydrophobic side chain, such as leucine, phenylalanine, methionine and valine), which provides a signal for rapid internalization. This signal is recognized by and binds to the µ2 subunit of AP-2, and mediates rapid internalization by mammalian cells. Preferably, the signal is present ion such a way as to be displayed on the cytosolic side of the membrane. See e.g., Bonifacino et al., J. Cell Biol. 145: 923 (May 31, 1999).

At least one binding domain of a multivalent *Clostridial* neurotoxin derivative of the present invention may comprise at least one sorting signal for an adaptin, preferably AP-2. Preferably, the binding site comprising this sorting signal is present in addition to another distinct binding domain which will directly bind a cell surface receptor.

In certain embodiments, a multivalent *Clostridial* neurotoxin derivative of the present invention comprising two or more pancreatic acinar cell targeting moieties may be administered to treat pancreatitis; the use of CCK forms and derivatives capable of selective binding to CCK receptors of pancreatic acinar cells is disclosed in U.S. Pat. No. 6,843,998. In one preferred embodiment of this aspect of the present invention, two or more binding moieties of the present invention are independently a CCK or CCK derivative.

In another embodiment of the invention for treatment of, e.g., acute or chronic pancreatitis, at least one binding moiety of the multivalent *Clostridial* neurotoxin derivative is a CCK or CCK derivative, and at least one additional binding region comprises a region of a glycosyl phosphatylinositol (GPI)-linked membrane protein that directly or indirectly binds caveolin-1 binding. Alternatively, the additional binding region may comprise a ligand capable of binding a GPI-linked membrane protein, particularly a membrane associated cell surface receptor, as the CCK receptor, like the TNF and other known receptors, is known to be concentrated and recruited for internalization by caveolae.

Caveolae are discrete membrane domains present in many cell types; they are not thought to be present in neural cells. Caveolae are comprised largely of detergent-insoluble lipids and lipid associated proteins, including a major protein, caveolin-1. Caveolae are also known to recruit and concentrate GPI-linked membrane proteins, a family of membrane proteins that includes cell surface receptors. Further, caveolae appear to participate in a non clatherin-associated form of endocytosis, and experiments have been reported in which gene transfer vectors have been directed to GPI-linked receptor proteins to facilitate gene transfer.

Thus, for example, the urokinase plasminogen activator receptor (uPAR) is a GPI-linked membrane protein that appears to facilitate endocytosis upon binding of its cognate ligand urokinase plasminigen activator (uPA). See e.g., Drapkin et al., J. CLIN. INVEST. 105: 589-596 (Mar. 1, 2000), incorporated by reference as part of this specification. uPA is a 55 KDa protein secreted by alveolar epithelial cells that cleaves plasminogen to plasmin and is known to degrade the extracellular matrix in alveoli. Targeting such cells, which also display the uPAR, with the multivalent *Clostridial* neurotoxin derivative of the present invention comprising, for example, two or more binding domains comprising a uPAR-binding region derived from, for example, uPA or an anti-uPAR antibody may be of therapeutic use is the treatment of respiratory and lung diseases such as e.g., cystic fibrosis, since the ligand-bound receptor is subject to endocytosis in a ligand dependent manner. Thus for example, a patient may be administered a mist or dispersion comprising such multivalent *Clostridial* neurotoxin derivative as a delivery mechanism.

In certain embodiments the target cell may comprise a cell comprising a membrane protein that displays an antibody variable region at the cell surface. In such a case the multivalent *Clostridial* neurotoxin derivative comprises two or more binding domains, with at least one binding domain comprising an antigen able to selectively bind the antibody variable region. In a preferred embodiment, the multivalent *Clostridial* neurotoxin derivative may comprise more than one binding region comprising an antigen able to selectively bind to said antibody variable region.

Alternatively, the multivalent *Clostridial* neurotoxin derivative of the present invention (comprising more than one binding domain), may have at least one binding domain comprising an antigen-binding portion of an antibody H or L chain, wherein the antigen comprises a cell surface marker for a target cell. For example, and without limitation, the multivalent *Clostridial* neurotoxin derivative of the present invention may comprise at least one binding domain comprising an antibody variable region that selectively binds to an eosinophil cell surface marker (for example, the cell surface markers CD 44 and CD 69), thereby aiding in alleviating the symptoms of allergy. The nomenclature "CD" is derived from the use of monoclonal antibodies directed towards a given cell type, and stands for "Cluster of Differentiation".

In another example, the multivalent *Clostridial* toxin derivative may be used to inhibit or decrease the rate of infection of T helper cells by the human immunodeficiency virus (HIV). T helper cells are commonly identified by virtue of their display of the cell surface marker CD4. The HIV virus uses the CD4 marker to gain entry into and thereby infect T helper cells, and appears to employ viral fusion proteins sharing remarkable similarity to the SNARE system to invade cells through a membrane fusion mechanism. See e.g., Duman & Forte, AM. J. PHYSIOL. CELL PHYSIOL. 285: C237-C249 (2003). A multivalent *Clostridial* neurotoxin derivative of the present invention comprising at least one, and preferably two or more, anti-CD4 antibody domain or similar CD4 "addressable" binding domain would permit the neurotoxin protease domain to deny the virus use of the SNARE proteins for entry and/or exit of the cell. Moreover, alteration of the toxin proteolytic domain to selectively recognize and cleave one or more of the HIV viral fusion proteins, using S such techniques as directed evolution, site directed mutagenesis or other well known molecular biology methods, could provide a method of reducing the extent of, or eliminating, HIV infection.

In some embodiments, one or more binding domain of the multivalent *Clostridial* neurotoxin derivative may comprise a translocation domain. As used herein, a "translocator" of the present invention comprises a protein, peptide (or a peptidomimetic) that facilitates the transport of the neurotoxin across a cell membrane. In some embodiments, the translocator may function independently of cell surface transporters or specific receptors, and therefore non-specifically. In this embodiment the multivalent *Clostridial* toxin derivative will also comprise at least one target cell selective ligand.

In other embodiments, a translocator may comprise a ligand selective for a cell surface transporter, feature, or receptor; in such an embodiment the multivalent *Clostridial* toxin derivative may comprise two or more identical binding domains, or may comprise at least one target cell selective domain and at least one target cell non-selective binding domain, so long as the number of binding domains totals at least two.

Without wishing to limit the invention to any theory or mechanism of operation, it is believed that the translocator comprises a protein translocation domain (PTD). Further, it is believed that the PTD is primarily responsible for the translocation of the neurotoxin across a cell membrane. PTDs are amino acid sequence domains that have been shown to cross biological membranes efficiently and independently of transporters or specific receptors. See e.g., Morris M. C. et al., NATURE BIOTECHNOLOGY, 19:1173-1176 (December 2001), the disclosure of which is incorporated in its entirety by reference herein. A number of PTDs have now been characterized and are well-known in the art. For example, the SV-40 virus large T-related PTD is:

CGGGPKKKRKVGG        (SEQ ID NO: 37)

an HIV TAT-related PTD is:

CGGRKKRRQRRRAP       (SEQ ID NO: 38)

an adenovirus related PTD is:

CGGFSTSLRARKA        (SEQ ID NO: 39)

a synthetic integrin binding domain-related PTD is:

CKKKKKKGGRGDMFG      (SEQ ID NO: 40)

In some embodiments, the multivalent *Clostridial* toxin derivative comprises at least two binding domains, wherein at least one of these domains comprises a ligand selected from the cell surface receptor-binding domains of ciliary neurotrophic factor (CNTF), caveolin, interleukin 1-β (Il-1β), thioredoxin, fibroblast growth factor-1 (FGF-1), fibroblast growth factor-2 (FGF-2), Human integrins such the β1 and β3 subunits, lactoferrin, Engrailed, Hoxa-5, Hoxb-4, or Hoxc-8. Engrailed-1, Engrailed-2, Hoxa-5, Hoxb-4 and Hoxc-8 are homeoproteins. Homeoproteins are helix-turn-helix proteins that contain a 60 amino acid DNA-binding domain, the homeodomain (HD) or homeobox. The PTD is believed to lie within the HD. When Engrailed-1 and Engrailed-2 are expressed in COS7 cells, they are secreted by the host cell and then reinternalized by other cells. Similar observations have been made for Hoxa-5, Hoxc-8 and Hoxb-4.

In some embodiments, the translocator is a PTD domain of a herpes simplex virus type 1 (HSV-1) VP22 protein, which is a transcription factor that concentrates in the nucleus and binds chromatin. It has been shown that VP22 traffics across the membrane via non-classical endocytosis and can enter cells regardless of GAP junctions and physical contacts. If VP22 is expressed in a small population of cells in culture, it will reach 100% of the cells in that culture. Fusion proteins with VP22 and for example p53, GFP, thymidine kinase, β-galactosidase and others have been generated. It has been demonstrated that the fusion proteins are taken up by several kinds of cells including terminally differentiated cells suggesting that mitosis is not a requirement for efficient entry. In addition, VP22-GFP fusion showed that the protein can shuttle in and out of the cells and enter cells that were not exposed to VP22.

The HIV-1 trans-activator gene product (TAT) was one of the earliest cell-permeating proteins described. A receptor-mediated event appears not to be required for TAT to pass into a neighboring cell; thus for selective cell targeting, a PTD is preferably used in conjunction with a more target cell-selective binding domain in the multivalent *Clostridial* toxin derivative of the present invention. HIV-1, as well as other lentiviruses, encodes a potent TAT protein. Embury et al., DIABETES 50:1706-1713, 2001 discuss the use the TAT PTD to transduce anti-apoptotic proteins into pancreatic islet cells. The PTD of TAT is a small peptide comprising amino acids 47-57 of the TAT protein; the PTD sequence comprises the amino acid sequence YGRKKRRQRRR (SEQ ID NO 41) or at least the nonapeptide comprising TAT amino acids 49-57. Fusion proteins comprising this peptide can transit the plasma membrane in vitro and in vivo. E.g., Schwartz, J. J. et al., Peptide-mediated cellular delivery, *Curr. Opin. Mol. Therapeutics* 2000, 2:162-7. The disclosures of these references are incorporated in their entirety by reference herein.

Furthermore, PTD-transported proteins and peptides, such as fusion peptides, have been shown to generally retain their biological properties and functions once inside the cells. Further, the TAT-PTD is able to carry a variety of cargo molecules including nucleic acids (DNA and RNA), and therapeutic drugs. The capability of this sequence to promote internalization of the peptide (and any cargo peptide) appears to be related to the strongly positive charge pf the PTD sequence, and not to be inhibited at 4° C. or in the presence of endocytosis inhibitors. Thus, the PTD appears not to be dependent upon active transport or recentor mediated endocytosis for this activity.

The PTD sequence is able to mediate the transduction of its cargo in a concentration dependent and receptor-, transporter-, and endocytosis-independent manner to 100% of the target cells in a given tissue or culture. Of special interest are the studies demonstrating that the PTD of TAT is able to deliver proteins in vivo to several different tissues when injected into animals.

In some embodiments, the multivalent *Clostridial* toxin derivative comprises at least one binding domain comprising a at least two PTDs, or at least three PTDs. Additional, non-limiting examples of PTDs are shown below.

```
Kaposi fibroblast growth factor membrane-
translocating sequence (kFGF MTS)
AAVALLPAVLLALLAP              (SEQ ID NO. 42)

Nuclear Localization Signal (NLS)
TPPKKKRKVEDP                  (SEQ ID NO. 43)

Transportan
GWTLNSAGYLLGKINLKALAALAKKIL   (SEQ ID NO. 44)

Herpes Simplex Virus Type 1 Protein 22 (VP22)
DAATATRGRSAASRPTERPRAPARSASRPRRPVE (SEQ ID NO. 45)
```

In some embodiments, PTDs contained in one or more binding site(s) of this invention are peptides derived from a homeoprotein. Homeoproteins are helix turn helix proteins that contain a 60 amino acid DNA-binding domain, the homeodomain (HD). PTDs may be derived from the HD. In some embodiments, PTDs are derived from the family of *Drosophila* homeoproteins. *Drosophila* homeoproteins are involved in developmental processes and are able to translocate across neuronal membranes. The third helix of the homeodomain of just 16 amino acids, known as penetratin, is able to translocate molecules into live cells. When added to several cell types in culture, 100% of the cells were able to uptake the peptide. Internalization occurs both at 37° C. and 4° C., and thus appears to be neither receptor-mediated nor energy-dependent. Several penetrating peptides, including those of the penetratin family, have been developed and used to internalize cargo molecules into the cytoplasm and nucleus of several cell types in vivo and in vitro. The results suggest that the entry of penetratin peptides is mediated by tryptophan, phenylalanine, and/or glutamine residues. In addition, the retro-inverse and all D-amino acid forms are also translocated efficiently using the penetratins, and non-α-helical structures are also internalized. See Prochiantz, A., Messenger proteins: homeoproteins, TAT and others, *Curr Opin Cell Biol* 2000, 12:400-6; and Schwartz, J J et al., Peptide-mediated cellular delivery, *Curr Opin Mol Therapeutics* 2000, 2:162-7. The disclosures of these references are incorporated in their entirety by reference herein.

In some embodiments, the translocator comprises the PDT of at least one penetratin peptide. Non-limiting examples of penetratin peptides are shown below:

```
RQIKIWFQNRRMKWKK       (SEQ ID NO: 46)

KKWKMRRNQFWIKIQR       (SEQ ID NO: 47)

RQIKIWFQNRRMKWKK       (SEQ ID NO: 48)

RQIKIWFPNRRMKWKK       (SEQ ID NO: 49)

RQPKIWFPNRRMPWKK       (SEQ ID NO: 50)

RQIKIWFQNMRRKWKK       (SEQ ID NO: 51)

RQIRIWFQNRRMRWRR       (SEQ ID NO: 52)

RRWRRWWRRWWRRWRR       (SEQ ID NO: 53)

RQIKIFFQNRRMKFKK       (SEQ ID NO: 54)

TERQIKIWFQNRRMK        (SEQ ID NO: 55)

KIWFQNRRMKWKKEN        (SEQ ID NO: 56)
```

In some embodiments, a translocator comprises a synthetic protein transduction domain. Other synthetic PTD sequences that may be employed in accordance with the present invention may be found in WO 99/29721 and Ho, A. et al., Synthetic PTDs: enhanced transduction potential in vitro and in vivo, CANCER RES 2001, 61, 474-7. In addition, it has been demonstrated that a 9-mer of L-Arginine is 20 fold more efficient than the TAT-PTD at cellular uptake, and when a D-arginine oligomer was used the rate enhancement was >100 fold. See Wender, P A et al., *The Design, Synthesis, And Evaluation Of Molecules That Enable Or Enhance Cellular Uptake: Peptoid Molecular Transporters*, PROC. NATL. ACAD. SCI. USA 2000, 97:13003-13008. These data suggested that the guanidinium groups of TAT-PTD play a greater role than charge or backbone structure in mediating cellular uptake. Thus, a peptoid analogue containing a six-methylene spacer between the guanidine head group and backbone was synthesized. This peptoid exhibited enhanced cellular uptake when compared to TAT-PTD and even to the D-Arg peptide.

In addition to the proteins and peptides discussed above, other peptide-mediated delivery systems have been described and are well-known to those of skill in the art. These PTD-containing proteins and peptides include: MPG, SCWKn, (LARL)n, HA2, RGD, AlkCWK$_{18}$, DiCWK$_{18}$, DipaLytic, K$_{16}$RGD, Plae and Kplae. See Schwartz, J J et al., Peptide-mediated cellular delivery, *Curr Opin Mol Therapeutics* 2000, 2:162-7. The disclosure of which is incorporated in its entirety by reference herein. In some embodiments, these

EXAMPLES

Example 1

Construction of a Multivalent *Clostridial* Neurotoxin Derivative Comprising Two *Clostridial* Toxin Binding Domains This example illustrates how to make a multivalent *Clostridial* neurotoxin derivative comprising two modified *Clostridial* toxin binding domains with enhanced binding activity using site-directed mutagenesis.

A polynucleotide molecule encoding BoNT/A (SEQ ID NO: 1) and further comprising a nucleotide sequence comprising a repeat of the binding domain of BoNT/A at the amino terminus (Table 1) is synthesized using standard procedures (BlueHeron® Biotechnology, Bothell, Wash.). The basic strategy is set forth in FIG. 1A and FIG. 1B. Oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/BoNT/MCND(AA)1. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

If desired, an expression-optimized polynucleotide molecule encoding BoNT/A (SEQ ID NO: 1) can be synthesized in order to improve expression in an *Escherichia coli* strain. The polynucleotide molecule encoding the BoNT/A can be modified to 1) contain synonymous codons typically present in native polynucleotide molecules of an *Escherichia coli* strain; 2) contain a G+C content that more closely matches the average G+C content of native polynucleotide molecules found in an *Escherichia coli* strain; 3) reduce polymononucleotide regions found within the polynucleotide molecule; and/or 4) eliminate internal regulatory or structural sites found within the polynucleotide molecule, see, e.g., Lance E. Steward et al. Optimizing Expression of Active Botulinum Toxin Type E, PCT Patent Serial No. 2005/020578 (Jun. 9, 2005); Lance E. Steward et al. Optimizing Expression of Active Botulinum Toxin Type A, PCT Patent Serial No. 2005/027917 (Aug. 3, 2005). Once sequence optimization is complete, oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/BoNT/MCND1/(AA)1:ECopt. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.). Is so desired, optimization to a different organism, such as, e.g., a yeast strain, an insect cell-line or a mammalian cell line, can be done, see, e.g., Steward, supra, PCT Patent Serial No. 2005/020578 (Jun. 9, 2005); and Steward, supra, PCT Patent Serial No. 2005/027917 (Aug. 3, 2005).

A similar cloning strategy is used to make pUCBHB1 cloning constructs comprising a polynucleotide molecule encoding BoNT/B of SEQ ID NO: 2; a polynucleotide molecule encoding BoNT/C1 of SEQ ID NO: 3; a polynucleotide molecule encoding BoNT/D of SEQ ID NO: 4; a polynucleotide molecule encoding BoNT/E of SEQ ID NO: 5; a polynucleotide molecule encoding BoNT/F of SEQ ID NO: 6; a polynucleotide molecule encoding BoNT/G of SEQ ID NO: 7; and a polynucleotide molecule encoding TeNT of SEQ ID NO: 8; each with an additional binding domain of any of the BONRT subtypes added to the amino terminus of the BoNT toxin sequence. In addition, one skilled in the art can modify *Clostridial* toxins, such as, e.g., to include an exogenous protease cleavage site within the di-chain loop region, or flexible spacer regions.

To construct pET29/MCND/A(AA)1, a pUCBHB1/MCND(AA)1 construct is digested with restriction endonucleases that 1) excise the insert comprising the open reading frame of SEQ ID NO: 1 (with the added nucleotide sequence encoding the N terminal Binding 1 site) encoding the MCND (AA)1; and 2) enable this insert to be operably-linked to a pET29 vector (EMD Biosciences-Novagen, Madison, Wis.). This insert is subcloned using a T4 DNA ligase procedure into a pET29 vector that is digested with appropriate restriction endonucleases to yield pET29/MCND/A(AA)1. The ligation mixture is transformed into chemically competent *E. coli* DH5α cells (Invitrogen, Inc, Carlsbad, Calif.) using a heat shock method, plated on 1.5% Luria-Bertani agar plates (pH 7.0) containing 50 μg/mL of Kanamycin, and placed in a 37° C. incubator for overnight growth. Bacteria containing expression constructs are identified as kanamycin resistant colonies. Candidate constructs are isolated using an alkaline lysis plasmid mini-preparation procedure and analyzed by restriction endonuclease digest mapping to determine the presence and orientation of the insert. This cloning strategy yields a pET29 expression construct comprising the polynucleotide molecule encoding the BoNT/A of SEQ ID NO: 1 operably-linked to an additional N-terminal binding site comprising the native binding region of BoNT/A.

A similar cloning strategy is used to make pET29 expression constructs comprising polynucleotide molecule encoding MCNDs comprising BoNT/B of SEQ ID NO: 2; a polynucleotide molecule encoding BoNT/C1 of SEQ ID NO: 3; a polynucleotide molecule encoding BoNT/D of SEQ ID NO: 4; a polynucleotide molecule encoding BoNT/E of SEQ ID NO: 5; a polynucleotide molecule encoding BoNT/F of SEQ ID NO: 6; a polynucleotide molecule encoding BoNT/G of SEQ ID NO: 7; and a polynucleotide molecule encoding TeNT of SEQ ID NO: 8, each with an additional N-terminal binding site of the same native BONT or TeNT subtype to which the binding site is linked. It will be understood that added binding sites of *Clostridial* neurotoxin subtypes other than that of the subtype to which the additional binding domain is linked may easily be substituted at the N-terminus of the MCND.

To construct a MCND comprising one or more modified binding domain with enhanced binding activity, specific amino acids influencing binding activity will be changed. For example, it is already known that amino acids Trp 1101, Gly 1102, Leu 1105, Tyr 1111, Tyr 1112, Gly 1158, Ile 1163, Asp 1179, Glu 1203, Phe 1252, Ser 1264, Trp 1266, Tyr 1267, Gln 1270, Gly 1279 and Trp 1282 of SEQ ID NO: 1 (within the binding site) are important for function. To determine which amino acid substitutions could enhance the binding activity of a BoNT/A binding domain, computational protein design algorithms will generate novel binding domains with optimized properties. The crystal structure of a BoNT/A binding domain will be used as the starting template for computational calculations. Potential amino acid candidates will be identified using a combined output from Protein Design Automation® (PDA®) and Sequence Prediction Algorithm™ (SPA™) calculations. For PDA calculations, the conformations of amino acids at variable positions will be represented as a set of backbone-independent side chain rotamers derived from the rotamer library. The energies of all possible combinations of the considered amino acids at the chosen variable positions will be calculated using a force field containing terms describing van der Waals, salvation, electrostatic, and hydrogen bond interactions. The optimal (ground state) sequence will be determined using a Dead End Elimination (DEE) algorithm, and a Monte Carlo (MC) algorithm will be used to evaluate the energies of similar sequences around the predicted ground state. SPA calculations utilize a genetic algorithm to screen for low energy sequences, with energies being calculated during each round of "evolution" for those sequences being sampled. The conformations of amino acids will be represented as a set of side chain rotamers derived from a backbone-independent rotamer library using a flexible rotamer model. SPA calculations will generate sequences which will be subsequently clustered computationally into groups of similar sequences using a nearest neighbor single linkage hierarchical clustering algorithm. Critical contact amino acids will be fixed in both sequence and conformation and calculations will be carried out to evaluate single and combinatorial substitutions at variable amino acids. All amino acids in contact with these residues will be floated, that is the amino acid conformation but not the amino acid identity will be allowed to vary to allow for conformational adjustments. Final experimental substitutions will be chosen based on their predicted energies relative to the naturally occurring BoNT/A binding domain and their occupancy, that is the number times the substitution occurred in the set of 1000 MC or genetic algorithm sequences. Two sets of design calculations will be carried out using Rosetta to identify substitutions predicted to stabilize the BoNT/A binding domain. In the first round, only single amino acid substitutions will be modeled. In a second round, interface amino acids will be allowed to change to all 20 naturally occurring amino acids including the native amino acid type, but excluding cysteine, simultaneously. In each case, amino acid side chains contacting the substituted amino acid side chains will be repacked (allowing all rotamers of the native amino acid type). Sequences and conformations with low energies will be selected using a Monte-Carlo simulated annealing procedure. All resulting protein complex models will be rescored by computing a predicted binding energy. Final sequences are selected for the lowest binding energy.

To use this information to generate one or more modified Clostridial neurotoxin binding domain, candidate amino acids identified as described above will be changed using site-directed in vitro mutagenesis. A 50 μL reaction will be assembled using pET29/MCND/A(AA)1 as a template, sense and antisense oligonucleotides encoding the desired amino acid change identified above, and reagents included with the QuickChange® II XL Site-Directed Mutagenesis kit (Stratagene, La Jolla, Calif.). The polymerase chain reaction (PCR) mix will contain 5 μL of 10× Buffer, 1 μL of deoxyribonucleotides (dNTPs), 1 μL of PfuUltra™ High Fidelity DNA polymerase (2.5 units/μL), 125 ng of each primer, 100 ng of template DNA, and nuclease-free water to a final volume of 50 μL. The thermocycler conditions will be: one cycle of 95° C. for 60 seconds; 16 cycles of 95° C. for 30 seconds, 55° C. for 60 seconds, and 72° C. for 10 minutes; one cycle of 72° C. for 5 minutes; and 4° C. to hold. Following thermocycling, 1 μL of DpnI restriction enzyme (Stratagene, La Jolla, Calif.) will be added to the reaction and will be incubated for 1 hour at 37° C. to digest the template DNA. The reaction will be purified by QIAquick kit (QIAGEN, Inc., Valencia, Calif.) and will be analysis by agarose gel electrophoresis to determine that the reaction produced full-length plasmid. The mutagenesis products will be transformed into chemically competent E. coli DH5α cells (Invitrogen, Inc, Carlsbad, Calif.) using a heat shock method, plated on 1.5% Luria-Bertani agar plates (pH 7.0) containing 100 μg/mL of Ampicillin, and will be placed in a 37° C. incubator for overnight growth. Candidate mutagenesis constructs will be isolated as Ampicillin resistant colonies and will be analyzed using an alkaline lysis plasmid mini-preparation procedure to isolate the expression construct and restriction endonuclease digests to determine the presence of the insert. The incorporation of the point mutation will be determined by sequence analysis of candidate plasmid constructs.

To test the binding activity of multivalent Clostridial neurotoxin derivatives comprising binding domains derived from BoNT/A, the soluble portion of FGFR3 will be expressed recombinantly for use in surface plasmon resonance (SPR) binding assays, e.g., Biacore® (Biacore Inc., Piscataway, N.J.) The soluble portion of FGFR3 will be expressed as a fusion to streptavidin and the receptor will then be immobilized on an appropriate sensor chip. Utilizing a Biacore® instrument, changes in local refractive index as a result of receptor binding will be measured as a change in the SPR angle. The rates of change in the SPR angle will then be analyzed to determine association rate ($K_{on}$), dissociation rate ($K_{off}$) and the dissociation equilibrium constant ($K_D=K_{off}/K_{on}$). Multivalent Clostridial neurotoxin derivatives comprising binding domains derived from BoNT/A exhibit either an increased association rate, a decreased dissociation rate, both an increased association rate and a decreased dissociation rate, or a decreased dissociation equilibrium constant relative to the measurements obtained from the naturally occurring BoNT/A from which the MCND is derived.

The same methods and rationale may be used to make and test the affinity of any multivalent Clostridial neurotoxin derivatives comprising binding domains derived from a Clostridial neurotoxin. Generally, but not exclusively, the MCND is tested relative to the Clostridial neurotoxin with which it shares the greatest homology, particularly in the binding domains.

Example 2

Construction of a Multivalent Clostridial Neurotoxin Derivative Comprising a Non-Toxin Associated Protein A polynucleotide molecule encoding BoNT/A-Nterm33/A is synthesized using standard procedures (BlueHeron® Biotechnology, Bothell, Wash.), as described in Example 1. BoNT/A-Nterm33/A is a BoNT/A modified to replace amino acids in the second binding domain (the N-terminal binding region of the MCND described in Example 1) corresponding to amino acids 1111-1296 of SEQ ID NO: 1, a BoNT/A β-trefoil domain, with amino acids 151 to 293 of SEQ ID NO: 9, a HA-33 β-trefoil domain from a Clostridial botulinum serotype A strain. If desired, an expression optimized polynucleotide molecule encoding BoNT/A-Nterm33/A can be synthesized in order to improve expression in to a different organism, such as, e.g., an Escherichia coli strain, a yeast strain, an insect cell-line or a mammalian cell line, can be done, see, e.g., Steward, supra, PCT Patent Serial No. 2005/020578 (Jun. 9, 2005); and Steward, supra, PCT Patent Serial No. 2005/027917 (Aug. 3, 2005). The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

A similar cloning strategy is used to make pUCBHB1 cloning constructs for MCND BoNT/B-Nterm33/A, a MCND based on BoNT/B where amino acids 1098-1291 of SEQ ID NO: 2 are replaced with amino acids 151 to 293 of SEQ ID NO: 9; MCND BoNT/C1-Nterm33/A, a MCND based on BoNT/C1 where amino acids 1112-1291 of SEQ ID NO: 3 are replaced with amino acids 151 to 293 of SEQ ID NO: 9; MCND BoNT/D-Nterm33/A, a MCND based on BoNT/D where amino acids 1099-1276 of SEQ ID NO: 4 are replaced with amino acids 151 to 293 of SEQ ID NO: 9; MCND BoNT/E-Nterm33/A, a MCND based on BoNT/E where amino acids 1086-1252 of SEQ ID NO: 5 are replaced with amino acids 151 to 293 of SEQ ID NO: 9; MCND BoNT/F-Nterm33/A, a MCND based on BoNT/F where amino acids 1106-1274 of SEQ ID NO: 6 are replaced with amino acids 151 to 293 of SEQ ID NO: 9; MCND BoNT/G-Nterm33/A, a MCND based on BoNT/G where amino acids 1106-1297 of SEQ ID NO: 7 are replaced with amino acids 151 to 293 of SEQ ID NO: 9; and MCND TeNT-Nterm33/A, a modified TeNT where amino acids 1128-1315 of SEQ ID NO: 8 are replaced with amino acids 151 to 293 of SEQ ID NO: 9.

Similarly, the β-trefoil domain from a *Clostridial* toxin indicated above can be replaced with a non-toxin associated protein β-trefoil domain comprising amino acids 10-144 of SEQ ID NO: 9; amino acids 10-144 of SEQ ID NO: 10; amino acids 10-144 of SEQ ID NO: 11; amino acids 10-146 of SEQ ID NO: 12; amino acids 10-144 of SEQ ID NO: 13; amino acids 10-144 of SEQ ID NO: 14; amino acids 10-146 of SEQ ID NO: 15; amino acids 10-141 of SEQ ID NO: 16; amino acids 10-141 of SEQ ID NO: 17; amino acids 10-141 of SEQ ID NO: 18; 151-293 of SEQ ID NO: 10; 151-293 of SEQ ID NO: 11; 153-294 of SEQ ID NO: 12; 151-279 of SEQ ID NO: 13; 151-292 of SEQ ID NO: 14; 153-291 of SEQ ID NO: 15; 148-285 of SEQ ID NO: 16; 148-286 of SEQ ID NO: 17; 148-286 of SEQ ID NO: 18; 9-146 of SEQ ID NO: 19; 9-146 of SEQ ID NO: 20; 9-146 of SEQ ID NO: 21; 9-146 of SEQ ID NO: 22; 1050-1194 of SEQ ID NO: 23; 1050-1199 of SEQ ID NO: 24; 1050-1194 of SEQ ID NO: 25; 1049-1198 of SEQ ID NO: 26; 1049-1197 of SEQ ID NO: 27; 1049-1197 of SEQ ID NO: 28; 1014-1163 of SEQ ID NO: 29; 1016-1160 of SEQ ID NO: 30; 1017-1166 of SEQ ID NO: 31; and 1050-1199 of SEQ ID NO: 32.

To construct pET29/MCND/BoNT/A-Nterm33/A, a pUCBHB1/BoNT/A-33/A construct is digested with restriction endonucleases that 1) excise the insert comprising the open reading frame encoding MCND/BoNT/A-Nterm33/A; and 2) enable this insert to be operably-linked to a pET29 vector (EMD Biosciences-Novagen, Madison, Wis.). This insert is subcloned using a T4 DNA ligase procedure into a pET29 vector that is digested with appropriate restriction endonucleases to yield pET29/MCND/BoNT/A-Nterm33/A. The ligation mixture is transformed into chemically competent *E. coli* DH5A cells (Invitrogen, Inc, Carlsbad, Calif.) using a heat shock method, plated on 1.5% Luria-Bertani agar plates (pH 7.0) containing 50 μg/mL of kanamycin, and placed in a 37° C. incubator for overnight growth. Bacteria containing expression constructs are identified as kanamycin resistant colonies. Candidate constructs are isolated using an alkaline lysis plasmid mini-preparation procedure and analyzed by restriction endonuclease digest mapping to determine the presence and orientation of the insert. This cloning strategy yielded a pET29 expression construct comprising the polynucleotide molecule encoding MCND/BoNT/A-Nterm33/A operably-linked to a carboxyl terminal polyhistidine affinity binding peptide.

A similar cloning strategy is used to make pET29 expression constructs comprising a polynucleotide molecule encoding for BoNT/B-33/A, BoNT/C1-33/A, BoNT/D-33/A, BoNT/E-33/A, BoNT/F-33/A, BoNT/G-33/A, TeNT-33/A, as well as the modified *Clostridial* toxin indicated above comprising amino acids 10-144 of SEQ ID NO: 9; amino acids 10-144 of SEQ ID NO: 10; amino acids 10-144 of SEQ ID NO: 11; amino acids 10-146 of SEQ ID NO: 12; amino acids 10-144 of SEQ ID NO: 13; amino acids 10-144 of SEQ ID NO: 14; amino acids 10-146 of SEQ ID NO: 15; amino acids 10-141 of SEQ ID NO: 16; amino acids 10-141 of SEQ ID NO: 17; amino acids 10-141 of SEQ ID NO: 18; 151-293 of SEQ ID NO: 10; 151-293 of SEQ ID NO: 11; 153-294 of SEQ ID NO: 12; 151-279 of SEQ ID NO: 13; 151-292 of SEQ ID NO: 14; 153-291 of SEQ ID NO: 15; 148-285 of SEQ ID NO: 16; 148-286 of SEQ ID NO: 17; 148-286 of SEQ ID NO: 18; 9-146 of SEQ ID NO: 19; 9-146 of SEQ ID NO: 20; 9-146 of SEQ ID NO: 21; 9-146 of SEQ ID NO: 22; 1050-1194 of SEQ ID NO: 23; 1050-1199 of SEQ ID NO: 24; 1050-1194 of SEQ ID NO: 25; 1049-1198 of SEQ ID NO: 26; 1049-1197 of SEQ ID NO: 27; 1049-1197 of SEQ ID NO: 28; 1014-1163 of SEQ ID NO: 29; 1016-1160 of SEQ ID NO: 30; 1017-1166 of SEQ ID NO: 31; and 1050-1199 of SEQ ID NO: 32.

Example 3

Construction of a Multivalent *Clostridial* Neurotoxin Derivative Comprising Three CCK-A Binding Sites The following example illustrates how to make a retargeted multivalent *Clostridial* neurotoxin derivative comprising three CCK-A binding sites.

A polynucleotide molecule is constructed as described in Example 1 above, encoding BoNT/A with the native binding site replaced with 10 repeats of the CCK 58 amino acid sequence (see U.S. Pat. No. 6,843,998, hereby incorporated by reference herein in its entirety) and with the same CCK 58 sequence repeated twice at the N-terminus of the single chain. The two N-terminal repeats are constructed to be separated by a short amino acid region comprising the loop region of BoNT/A, and two cysteine residues spanning the protease sensitive site. The MCND is termed MCND BoNT/A/C (CCK)N(CCKx2). The basic architecture of the amino acid construct is given in FIG. 2A.

If desired, an expression-optimized polynucleotide molecule encoding MCND BoNT/A/C(CCK)N(CCKx2) can be synthesized in order to improve expression in to a different organism, such as, e.g., an *Escherichia coli* strain, a yeast strain, an insect cell-line or a mammalian cell line, can be done, see, e.g., Steward, supra, PCT Patent Serial No. 2005/020578 (Jun. 9, 2005); and Steward, supra, PCT Patent Serial No. 2005/027917 (Aug. 3, 2005). The synthesized polynucleotide molecule is verified by sequencing using Big Dye Terminators™ Chemistry 3.1 (Applied Biosystems, Foster City, Calif.) and an ABI 3100 sequencer (Applied Biosystems, Foster City, Calif.).

A similar cloning strategy is used to make pUCBHB1 cloning constructs for C(CCK)N(CCKx2) MCND's in which the translocation and endopeptidase domains are independently selected from BoNT/B, C1, D, E, F, G, or TeNT.

To construct pET29/MCND BoNT/A/C(CCK)N (CCKx2), a pUCBHB1/MCND BoNT/A/C(CCK)N (CCKx2) construct is digested with restriction endonucleases that 1) excise the insert comprising the open reading frame encoding MCND BoNT/A/C(CCK)N(CCKx2); and 2) enable this insert to be operably-linked to a pET29 vector (EMD Biosciences-Novagen, Madison, Wis.). This insert is subcloned using a T4 DNA ligase procedure into a pET29 vector that is digested with appropriate restriction endonucleases to yield pET29/MCND BoNT/A/C(CCK)N (CCKx2). The ligation mixture is transformed into chemically competent *E. coli* DH5a cells (Invitrogen, Inc, Carlsbad, Calif.) using a heat shock method, plated on 1.5% Luria-Bertani agar plates (pH 7.0) containing 50 µg/mL of Kanamycin, and placed in a 37° C. incubator for overnight growth. Bacteria containing expression constructs are identified as Kanamycin resistant colonies. Candidate constructs are isolated using an alkaline lysis plasmid mini-preparation procedure and analyzed by restriction endonuclease digest mapping to determine the presence and orientation of the insert. This cloning strategy yielded a pET29 expression construct comprising the polynucleotide molecule encoding MCND BoNT/A/C(CCK)N(CCKx2), operably-linked to a carboxyl terminal polyhistidine affinity binding peptide.

A similar cloning strategy is used to make pET29 expression constructs comprising a polynucleotide molecule encoding any combination of translocation and endopeptidase domains derived from BoNT/A, B, C1, D, E, F, G or TeNT with CCK 58 domains similar positioned as in MCND BoNT/A/C(CCK)N(CCKx2).

Example 4

Purification and Quantification of Modified *Clostridial* Toxins

The following example illustrates methods useful for purification and quantification of any modified *Clostridial* toxins disclosed in the present specification.

For immobilized metal affinity chromatography (IMAC) protein purification, *E. coli* BL21 (DE3) cell pellets used to express a modified *Clostridial* toxin, as described in Example 7, are resuspended in Column Binding Buffer (25 mM N-(2-hydroxyethyl) piperazine-N'-(2-ethanesulfonic acid) (HEPES), pH 7.8; 500 mM sodium chloride; 10 mM imidazole; 2× Protease Inhibitor Cocktail Set III (EMD Biosciences-Calbiochem, San Diego Calif.); 5 units/mL of Benzonase (EMD Biosciences-Novagen, Madison, Wis.); 0.1% (v/v) Triton-X® 100, 4-octylphenol polyethoxylate; 10% (v/v) glycerol), and then are transferred to a cold Oakridge centrifuge tube. The cell suspension is sonicated on ice (10-12 pulses of 10 seconds at 40% amplitude with 60 seconds cooling intervals on a Branson Digital Sonifier) in order to lyse the cells and then is centrifuged (16,000 rpm at 4° C. for 20 minutes) to clarify the lysate. An immobilized metal affinity chromatography column is prepared using a 20 mL Econo-Pac column support (Bio-Rad Laboratories, Hercules, Calif.) packed with 2.5-5.0 mL of TALON® SuperFlow $Co^{2+}$ affinity resin (BD Biosciences-Clontech, Palo Alto, Calif.), which is then equilibrated by rinsing with 5 column volumes of deionized, distilled water, followed by 5 column volumes of Column Binding Buffer. The clarified lysate is applied slowly to the equilibrated column by gravity flow (approximately 0.25-0.3 mL/minute). The column is then washed with 5 column volumes of Column Wash Buffer (N-(2-hydroxyethyl) piperazine-N'-(2-ethanesulfonic acid) (HEPES), pH 7.8; 500 mM sodium chloride; 10 mM imidazole; 0.1% (v/v) Triton-X® 100, 4-octylphenol polyethoxylate; 10% (v/v) glycerol). The modified *Clostridial* toxin is eluted with 20-30 mL of Column Elution Buffer (25 mM N-(2-hydroxyethyl) piperazine-N'-(2-ethanesulfonic acid) (HEPES), pH 7.8; 500 mM sodium chloride; 500 mM imidazole; 0.1% (v/v) Triton-X® 100, 4-octylphenol polyethoxylate; 10% (v/v) glycerol) and is collected in approximately twelve 1 mL fractions. The amount of modified *Clostridial* toxin contained in each elution fraction is determined by a Bradford dye assay. In this procedure, 20 µL aliquots of each 1.0 mL fraction is combined with 200 µL of Bio-Rad Protein Reagent (Bio-Rad Laboratories, Hercules, Calif.), diluted 1 to 4 with deionized, distilled water, and then the intensity of the calorimetric signal is measured using a spectrophotometer. The five fractions with the strongest signal are considered the elution peak and are combined together. Total protein yield is determined by estimating the total protein concentration of the pooled peak elution fractions using bovine gamma globulin as a standard (Bio-Rad Laboratories, Hercules, Calif.).

For purification of a modified *Clostridial* toxin using a FPLC desalting column, a HiPrep™ 26/10 size exclusion column (Amersham Biosciences, Piscataway, N.J.) is pre-equilibrated with 80 mL of 4° C. Column Buffer (50 mM sodium phosphate, pH 6.5). After the column is equilibrated, a modified *Clostridial* toxin sample is applied to the size exclusion column with an isocratic mobile phase of 4° C. Column Buffer and at a flow rate of 10 mL/minute using a BioLogic DuoFlow chromatography system (Bio-Rad Laboratories, Hercules, Calif.). The desalted modified *Clostridial* toxin sample is collected as a single fraction of approximately 7-12 mL.

For purification of a modified *Clostridial* toxin using a FPLC ion exchange column, a modified *Clostridial* toxin sample that has been desalted following elution from an IMAC column is applied to a 1 mL Q1™ anion exchange column (Bio-Rad Laboratories, Hercules, Calif.) using a BioLogic DuoFlow chromatography system (Bio-Rad Laboratories, Hercules, Calif.). The sample is applied to the column in 4° C. Column Buffer (50 mM sodium phosphate, pH 6.5) and is eluted by linear gradient with 4° C. Elution Buffer (50 mM sodium phosphate, 1 M sodium chloride, pH 6.5) as follows: step 1, 5.0 mL of 5% Elution Buffer at a flow rate of 1 mL/minute; step 2, 20.0 mL of 5-30% Elution Buffer at a flow rate of 1 mL/minute; step 3, 2.0 mL of 50% Elution Buffer at a flow rate of 1.0 mL/minute; step 4, 4.0 mL of 100% Elution Buffer at a flow rate of 1.0 mL/minute; and step 5, 5.0 mL of 0% Elution Buffer at a flow rate of 1.0 mL/minute. Elution of modified *Clostridial* toxin from the column is monitored at 280, 260, and 214 nm, and peaks absorbing above a minimum threshold (0.01 au) at 280 nm are collected. Most of the modified *Clostridial* toxin will elute at a sodium chloride concentration of approximately 100 to 200 mM. Average total yields of modified *Clostridial* toxin will be determined by a Bradford assay.

Expression of a modified *Clostridial* toxin is analyzed by polyacrylamide gel electrophoresis. Samples purified using the procedure described above are added to 2×LDS Sample Buffer (Invitrogen, Inc, Carlsbad, Calif.) and are separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Gels are stained with SYPRO® Ruby (Bio-Rad Laboratories, Hercules, Calif.) and the separated polypeptides are imaged using a Fluor-S MAX MultiImager (Bio-Rad Laboratories, Hercules, Calif.) for quantification of modified *Clostridial* toxin expression levels. The size and amount of modified *Clostridial* toxin is determined by comparison to MagicMark™ protein molecular weight standards (Invitrogen, Inc, Carlsbad, Calif.).

Expression of modified *Clostridial* toxin is also analyzed by Western blot analysis. Protein samples purified using the procedure described above are added to 2×LDS Sample Buffer (Invitrogen, Inc, Carlsbad, Calif.) and are separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Separated polypeptides are transferred from the gel onto polyvinylidene fluoride (PVDF) membranes (Invitrogen, Inc, Carlsbad, Calif.) by Western blotting using a Trans-Blot® SD semi-dry electrophoretic transfer cell apparatus (Bio-Rad Laboratories, Hercules, Calif.). PVDF membranes are blocked by incubating at room temperature for 2 hours in a solution containing 25 mM Tris-Buffered Saline (25 mM 2-amino-2-hydroxymethyl-1,3-propanediol hydrochloric acid (Tris-HCl)(pH 7.4), 137 mM sodium chloride, 2.7 mM potassium chloride), 0.1% TWEEN-20®, polyoxyethylene (20) sorbitan monolaureate, 2% bovine serum albumin, 5% nonfat dry milk. Blocked membranes are incubated at 4° C. for overnight in Tris-Buffered Saline TWEEN-20® (25 mM Tris-Buffered Saline, 0.1% TWEEN-20®, polyoxyethylene (20) sorbitan monolaureate) containing appropriate primary antibodies as a probe. Primary antibody probed blots are washed three times for 15 minutes each time in Tris-Buffered Saline TWEEN-20®. Washed membranes are incubated at room temperature for 2 hours in Tris-Buffered Saline TWEEN-20® containing an appropriate immunoglobulin G antibody conjugated to horseradish peroxidase as a secondary antibody. Secondary antibody-probed blots are washed three times for 15 minutes each time in Tris-Buffered Saline TWEEN-20®. Signal detection of the labeled modified *Clostridial* toxin are visualized using the ECL Plus™ Western Blot Detection System (Amersham Biosciences, Piscataway, N.J.) and are imaged with a Typhoon 9410 Variable Mode Imager (Amersham Biosciences, Piscataway, N.J.) for quantification of modified *Clostridial* toxin expression levels.

Example 5

Treatment of Hyperhidrosis Using a Multivalent *Clostridial* Neurotoxin Derivative A 32-year-old woman presents complaining with chronic and excessive perspiring under the arms and in the palm of the hands. Clinical examination reveals a high degree of sweating under the arms, and stains on clothing in the same area.

The patient is injected in the eccrine glands under one arm with an approximately minimum effective dose (15 drops) of BOTOX®. The same patient is injected in the eccrine glands under the other arm with 7 drops of the Multivalent *Clostridial* Neurotoxin Derivative of Example 1.

The patient is observed one week later. Examination reveals that excessive sweating under the arms has been deceased by 85-95% in both cases, despite the fact that the MCND was administed at less than 50% of the BOTOX® dosage.

Example 6

Treatment of Acute Pancreatitis with a Multivalent *Clostridial* Neurotoxin Derivative A 55 year-old man with a history of alcoholism presents with nausea, loss of appetite and severe abdominal pain radiating to the back. Examination reveals that the patient suffers from acute pancreatitis with a Balthazar Score of Grade D (with fluid collection in a single pancreatic location). The acute and advancing pancreatic necrosis threatens the patient's life.

The patient is administered the multivalent *Clostridial* neurotoxin derivative of Example 3 in an effective dose by injection directly into the pancreatic acini. Within 48 hours, there is a halt in the progression of the patient's deterioration. Within two weeks the acute pain has been relieved and the patient is able to take oral nourishment.

Although aspects of the present invention have been described with reference to the disclosed embodiments, one skilled in the art will readily appreciate that the specific examples disclosed are only illustrative of these aspects and in no way limit the present invention. Various modifications can be made without departing from the spirit of the present invention.

Any and all patents, publications, patent applications, and nucleotide and/or amino acid sequences referred to by accession numbers cited in this specification are hereby incorporated by reference as part of this specification.

Each and every feature described herein, and each and every combination of two or more of such features, is included within the scope of the present invention provided that the features included in such a combination are not mutually inconsistent.

These and other aspects of the present invention are set forth in the following claims.

What is claimed is:

1. A polypeptide comprising:
   a) an endopeptidase domain;
   b) a translocation domain effective to facilitate the movement of said endopeptidase domain across an endosomal membrane; and
   c) at least two binding domains, wherein:
      i) a first binding domain comprises a first ligand binding, under physiological conditions, to a first cell surface receptor displayed by the target cell; and
      ii) a second binding domain comprises a second ligand binding, under physiological conditions, to a second cll surface receptor displayed by the target cell;
   wherein said target cell internalizes said polypeptide upon binding of said polypeptide to said target cell.

2. The polypeptide of claim 1 wherein said second cell surface receptor comprises a caveolin-binding domain.

3. The polypeptide of claim 1 wherein said second cell surface receptor comprises TNFR-1.

4. The polypeptide of claim 3 wherein said second ligand comprises TNF-α.

5. The polypeptide of claim 2 wherein said second ligand binds a glycosyl phosphatylinositol (GPI)-linked membrane protein.

6. The polypeptide of claim 1 wherein said second cell surface receptor comprises an antibody variable (V) domain region.

7. The polypeptide of claim 6 wherein said second ligand comprises an antigen that selectively binds the antibody variable domain region of said second cell surface receptor.

8. The polypeptide of claim 1 wherein said second cell surface receptor binds clatherin.

9. The polypeptide of claim 8 wherein the second cell surface receptor has the amino acid sequence tyrosine-X-arginine-phenylalanine near the carboxy terminus.

10. The polypeptide of claim 8 wherein the second cell surface receptor binds an adaptin.

11. The polypeptide of claim 10 wherein the second cell surface receptor binds Adaptor Protein-2.

12. The polypeptide of claim 1 wherein the first ligand selectively binds a *Clostridial* neurotoxin-binding cell surface receptor.

13. The polypeptide of claim 12 wherein the first ligand comprises a *Clostridial* neurotoxin binding domain.

14. The polypeptide of claim 13 wherein the first ligand comprises a *Clostridial* neurotoxin binding domain selected from the group consisting of
   a) a TeNT receptor binding domain;
   b) a BoNT-A receptor binding domain;
   c) a BoNT-B receptor binding domain;
   d) a BoNT-C receptor binding domain;
   e) a BoNT-C1 receptor binding domain;
   f) a BoNT-D receptor binding domain;
   g) a BoNT-E receptor binding domain;
   h) a BoNT-F receptor binding domain;
   i) a BoNT-G receptor binding domain HA or NTNH β trefoil domain of a neurotoxin associated protein (NAP) associated with any *Clostridial* neurotoxin, and
   j) variants and isoforms of any of the above.

15. The polypeptide of claim 1 wherein first or second ligand comprises a receptor-binding domain selected from the group consisting of: a nerve growth factor (NGF) receptor binding domain; a leukemia inhibitory factor (LIF) receptor binding domain; a basic fibroblast growth factor (bFGF) receptor binding domain; the brain-derived neurotrophic factor (BDNF) receptor binding domain; a neurotrophin-3 (NT-3) receptor binding domain; a hydra head activator peptide (HHAP) receptor binding domain; a transforming growth factor 1 (TGF-1) receptor binding domain; a transforming growth factor 2 (TGF-2) receptor binding domain; a transforming growth factor 3(TGF-3) receptor binding domain; an epidermal growth factor (EGF) receptor binding domain; a ciliary neurotrophic factor (CNTF) receptor binding domain; a tumor necrosis factor (TNF-) receptor binding domain; an interleukin-1 (IL-1) receptor binding domain; an interleukin-1 (IL-1) receptor binding domain; an interleukin-8 (IL-8) receptor binding domain; a bradykinin receptor binding domain; a dynorphin receptor binding domain; a β-endorphin receptor binding domain; an etorphine receptor binding domain; an endomorphin-1 receptor binding domain; an endomorphin-2 receptor binding domain; a leu-enkephalin receptor binding domain; a met-enkephalin receptor binding domain; a galanin receptor binding domain; a lofentanil receptor binding domain; a nociceptin receptor binding domain; an antigen-binding variable region of an antibody against the lactoseries carbohydrate epitopes found on the surface of dorsal root ganglion neurons; an antigen-binding variable region of an antibody binding any of the receptors for the binding domains given above and an antibody against the surface expressed antigen Thyl.

16. The polypeptide of claim 15 wherein said first and second ligands are different.

17. The polypeptide of claim 14 wherein said second ligand comprises a receptor-binding domain selected from the group consisting of: a nerve growth factor (NGF) receptor binding domain; a leukemia inhibitory factor (LIF) receptor binding domain; a basic fibroblast growth factor (bFGF) receptor binding domain; the brain-derived neurotrophic factor (BDNF) receptor binding domain; a neurotrophin-3 (NT-3) receptor binding domain; a hydra head activator peptide (HHAP) receptor binding domain; a transforming growth factor 1 (TGF-1) receptor binding domain; a transforming growth factor 2 (TGF-2) receptor binding domain; a transforming growth factor 3(TGF-3) receptor binding domain; an epidermal growth factor (EGF) receptor binding domain; a ciliary neurotrophic factor (CNTF) receptor binding domain; a tumor necrosis factor (TNF-) receptor binding domain; an interleukin-1 (IL-1) receptor binding domain; an interleukin-1 (IL-1) receptor binding domain; an interleukin-8 (IL-8) receptor binding domain; a bradykinin receptor binding domain; a dynorphin receptor binding domain; a β-endorphin receptor binding domain; an etorphine receptor binding domain; an endomorphin-1 receptor binding domain; an endomorphin-2 receptor binding domain; a leu-enkephalin receptor binding domain; a met-enkephalin receptor binding domain; a galanin receptor binding domain; a lofentanil receptor binding domain; a nociceptin receptor binding domain; an antigen-binding variable region of an antibody against the lactoseries carbohydrate epitopes found on the surface of dorsal root ganglion neurons; an antigen-binding variable region of an antibody binding any of the receptors for the binding domains given above and an antibody against the surface expressed antigen Thyl.

18. The polypeptide of claim 15 wherein said second cell surface receptor comprises a caveolin-binding domain.

19. The polypeptide of claim 15 wherein said second cell surface receptor comprises TNFR-1.

20. The polypeptide of claim 19 wherein said second ligand comprises TNF-α.

21. The polypeptide of claim 18 wherein said second ligand binds a glycosyl phosphatylinositol (GPI)-linked membrane protein.

22. The polypeptide of claim 15 wherein said second cell surface receptor comprises an antibody variable (V) domain region.

23. The polypeptide of claim 22 wherein said second ligand comprises an antigen that selectively binds the antibody variable domain region of said second cell surface receptor.

24. The polypeptide of claim 15 wherein said second cell surface receptor binds clatherin.

25. The polypeptide of claim 24 wherein the second cell surface receptor has the amino acid sequence tyrosine-X-arginine-phenylalanine near the carboxy terminus.

26. The polypeptide of claim 24 wherein the second cell surface receptor binds an adaptin.

27. The polypeptide of claim 26 wherein the second cell surface receptor binds Adaptor Protein-2.

* * * * *

UNITED STATES PATENT AND TRADEMARK OFFICE
CERTIFICATE OF CORRECTION

| | |
|---|---|
| PATENT NO. | : 7,514,088 B2 |
| APPLICATION NO. | : 11/376696 |
| DATED | : April 7, 2009 |
| INVENTOR(S) | : Lance E. Steward et al. |

It is certified that error appears in the above-identified patent and that said Letters Patent is hereby corrected as shown below:

On the Title page, in field (56), in "Other Publications" column 2, line 4, delete "telani" and insert -- tetani --, therefor.

On the Title page, in field (56), in "Other Publications" column 2, line 10, delete "Associated" and insert -- associated --, therefor.

On the Title page, in field (56), in "Other Publications" column 2, line 11, delete "Clostridial" and insert -- Clostridium --, therefor.

On the Title page, in field (56), in "Other Publications" column 2, line(s) 11–12, delete "trefoil" and insert -- Trefoil --, therefor.

On the Title page, in field (56), in "Other Publications" column 2, line 12, delete "346 J. Mol. Biol.," and insert -- Journal of Molecular Biology, Vol. 346, No. 4, --, therefor.

On the Title page, in field (56), in "Other Publications" column 2, line 13, delete "(2005)." and insert -- March 4, 2005. --, therefor.

On the Title page, in field (57), in "Abstract" column 2, line 6, delete "man" and insert -- may --, therefor.

On Title page 2, in field (56), in "Other Publications" column 2, line 18, delete "Trasnsporters" and insert -- Transporters --, therefor.

In column 8, lines 26, 44 and 66, delete "Haemagglutinin" and insert -- Hemagglutinin --, therefor.

In column 8, line 31, delete "2005)." and insert -- (2005). --, therefor.

UNITED STATES PATENT AND TRADEMARK OFFICE
CERTIFICATE OF CORRECTION

| | |
|---|---|
| PATENT NO. | : 7,514,088 B2 |
| APPLICATION NO. | : 11/376696 |
| DATED | : April 7, 2009 |
| INVENTOR(S) | : Lance E. Steward et al. |

It is certified that error appears in the above-identified patent and that said Letters Patent is hereby corrected as shown below:

In column 8, line 32, delete "Clostridum" and insert -- Clostridium --, therefor.

In column 8, line 64, delete "an" and insert -- can --, therefor.

In column 12, line 23, delete "algorithims;" and insert -- algorithms; --, therefor.

In column 12, line 62, delete "Occurring" and insert -- occurring --, therefor.

In column 14, line 30, delete "BONT" and insert -- BoNT --, therefor.

In column 16, line 52, delete "plasminigen" and insert -- plasminogen --, therefor.

In column 16, line 65, delete "Thus" and insert -- Thus, --, therefor.

In column 17, line 42, after "using" delete "S".

In column 22, line 11, delete "BONRT" and insert -- BoNRT --, therefor.

In column 22, line 50, delete "BONT" and insert -- BoNT --, therefor.

In column 23, line 11, delete "salvation," and insert -- solvation, --, therefor.

In column 24, line 24, after "N.J.)" insert -- . -- .

In column 25, line 61, delete "DHSA" and insert -- DH5α --, therefor.

In column 27, line 12, delete "DH5a" and insert -- DH5α --, therefor.

In column 28, line 14, delete "calorimetric" and insert -- colorimetric --, therefor.

UNITED STATES PATENT AND TRADEMARK OFFICE
CERTIFICATE OF CORRECTION

PATENT NO. : 7,514,088 B2
APPLICATION NO. : 11/376696
DATED : April 7, 2009
INVENTOR(S) : Lance E. Steward et al.

It is certified that error appears in the above-identified patent and that said Letters Patent is hereby corrected as shown below:

In column 30, line 9, delete "administed" and insert -- administered --, therefor.

In column 169, line 13, in Claim 1, delete "cll" and insert -- cell --, therefor.

In column 170, line 4, in Claim 15, delete "3(TGF-3)" and insert -- 3 (TGF-3) --, therefor.

In column 170, line(s) 8–9, in Claim 15, after "domain;" delete "an interleukin-1 (IL-1) receptor binding domain;". (Second Occurrence)

In column 170, line 38, in Claim 17, delete "3(TGF-3)" and insert -- 3 (TGF-3) --, therefor.

In column 170, line(s) 42-43, In Claim 17, after "domain;" delete "an interleukin-1 (IL-1) receptor binding domain;". (Second Occurrence)

Signed and Sealed this

Thirtieth Day of June, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,514,088 B2
APPLICATION NO. : 11/376696
DATED : April 7, 2009
INVENTOR(S) : Lance E. Steward et al.

It is certified that error appears in the above-identified patent and that said Letters Patent is hereby corrected as shown below:

Title Page item (75)

Delete "Fernandez-Salas Ester" and insert in place thereof --Ester Fernandez-Salas--

Delete "Shengwin Li" and insert in place thereof --Shengwen Li--

Signed and Sealed this

Twenty-seventh Day of October, 2009

David J. Kappos
*Director of the United States Patent and Trademark Office*